US012564631B2

(12) United States Patent
Mendez-Gomez et al.

(10) Patent No.: US 12,564,631 B2

(45) Date of Patent: Mar. 3, 2026

(54) PHYTOSPHINGOSINE DERIVATIVES AS ADJUVANTS IN IMMUNE STIMULATION

(71) Applicants: Helmholtz-Zentrum für Infektionsforschung GmbH, Braunschweig (DE); Leibniz-Institut für Pflanzenbiochemie, Halle (DE)

(72) Inventors: Yanira Mendez-Gomez, Halle (DE); Bernhard Westermann, Halle (DE); Daniel Garcia-Rivera, Halle (DE); Aldrin Vasco-Vidal, Halle (DE); Ludger Wessjohann, Halle (DE); Carlos A. Guzmán, Wolfenbüttel (DE); Thomas Ebensen, Langenhagen (DE); Kai Schulze, Wolfsburg (DE); Peggy Riese, Braunschweig (DE); Stephanie Trittel, Hannover (DE)

(73) Assignees: Helmholtz-Zentrum für Infektionsforschung GmbH, Braunschweig (DE); Leibniz-Institut für Pflanzenbiochemie, Halle (DE)

( * ) Notice: Subject to any disclaimer, the term of this patent is extended or adjusted under 35 U.S.C. 154(b) by 701 days.

(21) Appl. No.: 18/002,120

(22) PCT Filed: Jun. 18, 2021

(86) PCT No.: PCT/EP2021/066715

§ 371 (c)(1),
(2) Date: Dec. 16, 2022

(87) PCT Pub. No.: WO2021/255287

PCT Pub. Date: Dec. 23, 2021

(65) Prior Publication Data

US 2023/0129118 A1 Apr. 27, 2023

(30) Foreign Application Priority Data

Jun. 18, 2020 (EP) .................................... 20180842

(51) Int. Cl.

| | |
|---|---|
| ***A61K 39/39*** | (2006.01) |
| ***A61K 47/55*** | (2017.01) |
| ***A61P 37/04*** | (2006.01) |
| ***C07H 15/04*** | (2006.01) |
| ***C07H 15/08*** | (2006.01) |
| ***C07H 15/22*** | (2006.01) |
| ***C07H 15/26*** | (2006.01) |

(52) U.S. Cl.

CPC .............. *A61K 39/39* (2013.01); *A61K 47/55* (2017.08); *A61P 37/04* (2018.01); *C07H 15/04* (2013.01); *C07H 15/08* (2013.01); *C07H 15/22* (2013.01)

(58) Field of Classification Search

None

See application file for complete search history.

(56) References Cited

U.S. PATENT DOCUMENTS

| | | | | |
|---|---|---|---|---|
| 8,053,417 B2 * | 11/2011 | Ebensen | A61P 37/04 514/23 |
| 2005/0192248 A1 | 9/2005 | Tsuji et al. | |
| 2008/0206319 A1 * | 8/2008 | Ebensen | A61K 39/39 424/277.1 |
| 2010/0222548 A1 * | 9/2010 | Wessjohann | A61P 31/00 530/328 |
| 2013/0217639 A1 | 8/2013 | Yu et al. | |
| 2015/0071960 A1 * | 3/2015 | Wong | A61P 1/16 424/193.1 |

FOREIGN PATENT DOCUMENTS

| | | | |
|---|---|---|---|
| EP | 2058011 A1 * | 5/2009 | A61K 47/646 |
| WO | WO 2007/045469 A1 | 4/2007 | |
| WO | WO-2008005824 A1 * | 1/2008 | A61K 47/543 |

OTHER PUBLICATIONS

Morita, Masahiro, et al. "Structure-activity relationship of alpha-Galactosylceramides against B16-bearing mice." Journal of medicinal chemistry 38.12 (1995): 2176-2187. (Year: 1995).*

Pérez-Labrada, Karell, et al. "Multicomponent synthesis of Ugi-type ceramide analogues and neoglycolipids from lipidic isocyanides." The Journal of Organic Chemistry 77.10 (2012): 4660-4670. (Year: 2012).*

Jervis, Peter J., et al. "Towards multivalent CD1d ligands: synthesis and biological activity of homodimeric α-galactosyl ceramide analogues." Carbohydrate research 356 (2012): 152-162. (Year: 2012).*

Huang, Yin-Cheng, et al. "Synthesis of Amino Core Compounds of Galactosyl Phytosyl Ceramide Analogs for Developing iNKT-Cell Inducers." Molecules 17.3 (2012): 3058-3081. (Year: 2012).*

Suzuki, Masahiro, Haruka Uematsu, and Kenji Hanabusa. "Novel organogelators based on phytosphingosine." Tetrahedron Letters 57.25 (2016): 2807-2810. (Year: 2016).*

(Continued)

*Primary Examiner* — Bethany P Barham

*Assistant Examiner* — Peter Anthopolos

(74) *Attorney, Agent, or Firm* — Knobbe, Martens, Olson & Bear, LLP

(57) ABSTRACT

Phytosphingosine derivatives suitable as adjuvants in immune stimulation, pharmaceutical compositions comprising such compounds and the medical use of the compounds and/or compositions in therapeutic or prophylactic methods of immune stimulation in a subject, and for use in the treatment of a disease, for which stimulation of an immune response in a subject produces a therapeutic benefit. The phytosphingosine derivative may also be used as adjuvants in vaccinating a subject. The phytosphingosine derivative may also be used in stimulating antibody production, stimulating an immune response against infection, stimulating an immune response against a cancer, or preventing and/or treating septic shock. Methods for the manufacture of the derivatives comprising an Ugi-4-component reaction (Ugi-4CR) is also disclosed.

20 Claims, 17 Drawing Sheets

(56) References Cited

OTHER PUBLICATIONS

Kahraman, Emine, et al. "Recent advances on topical application of ceramides to restore barrier function of skin." Cosmetics 6.3 (Aug. 20, 2019): 52. (Year: 2019).*
International Search Report and Written Opinion in PCT/EP2021/066715 dated Jul. 12, 2021.

* cited by examiner

Fig. 1
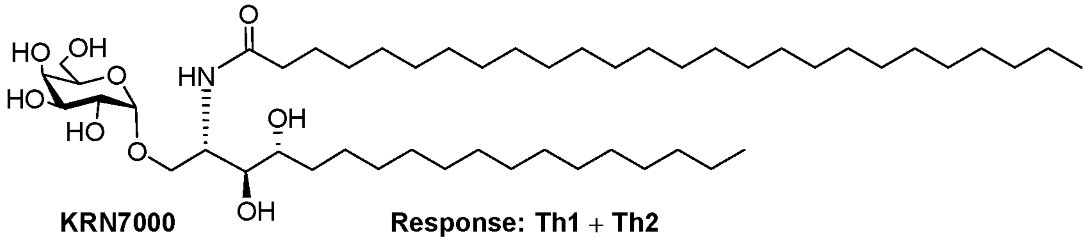
KRN7000 Response: Th1 + Th2
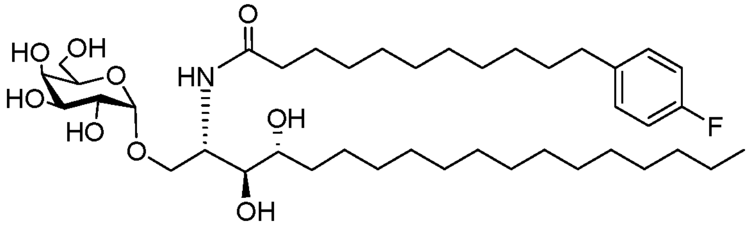
7DW8-5 Response: Th1
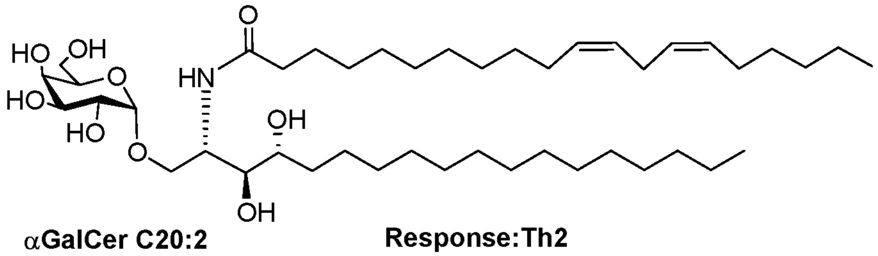
αGalCer C20:2 Response:Th2
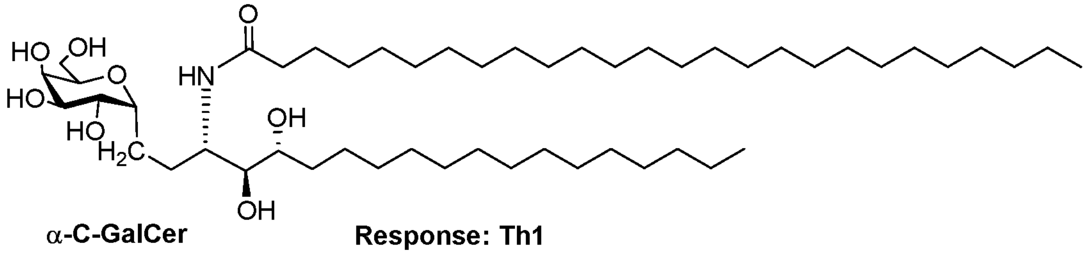
α-C-GalCer Response: Th1
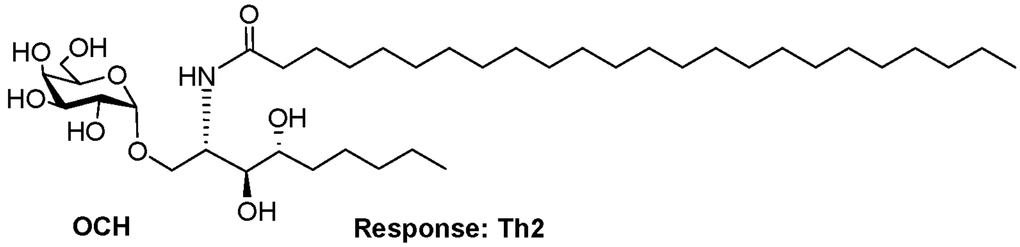
OCH Response: Th2

Fig. 2
A
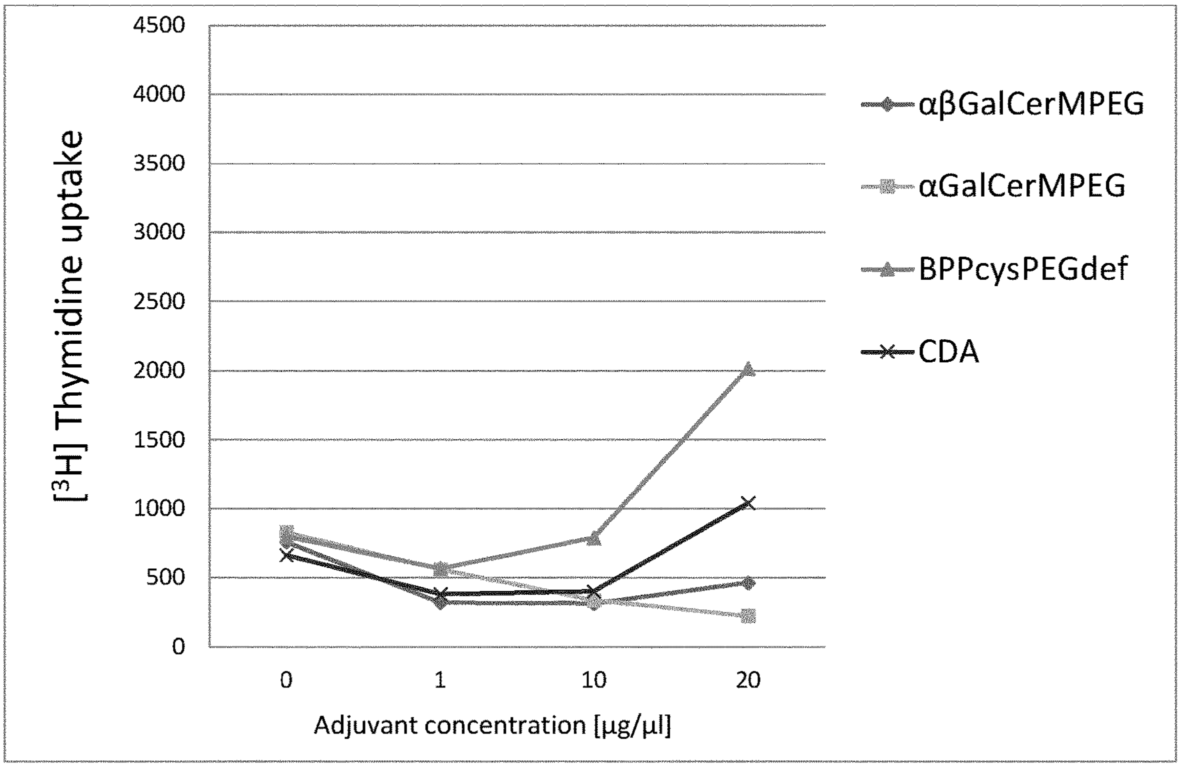
B
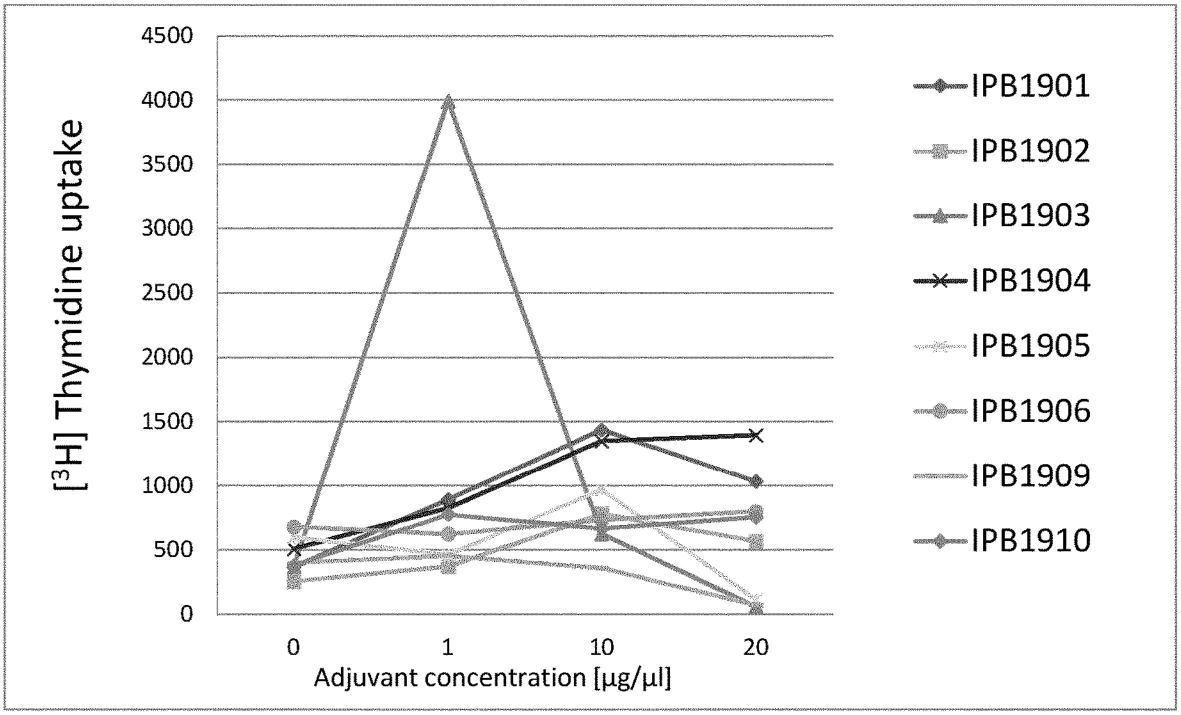

Fig. 2 (cont.)
C
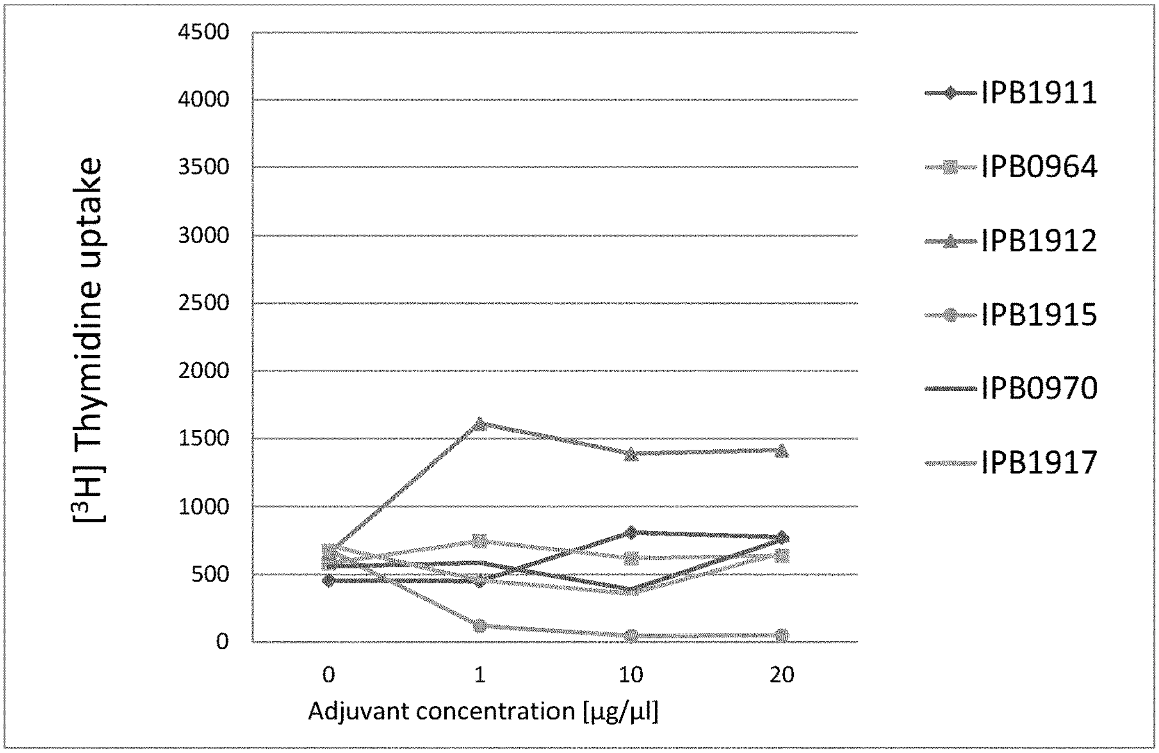
D
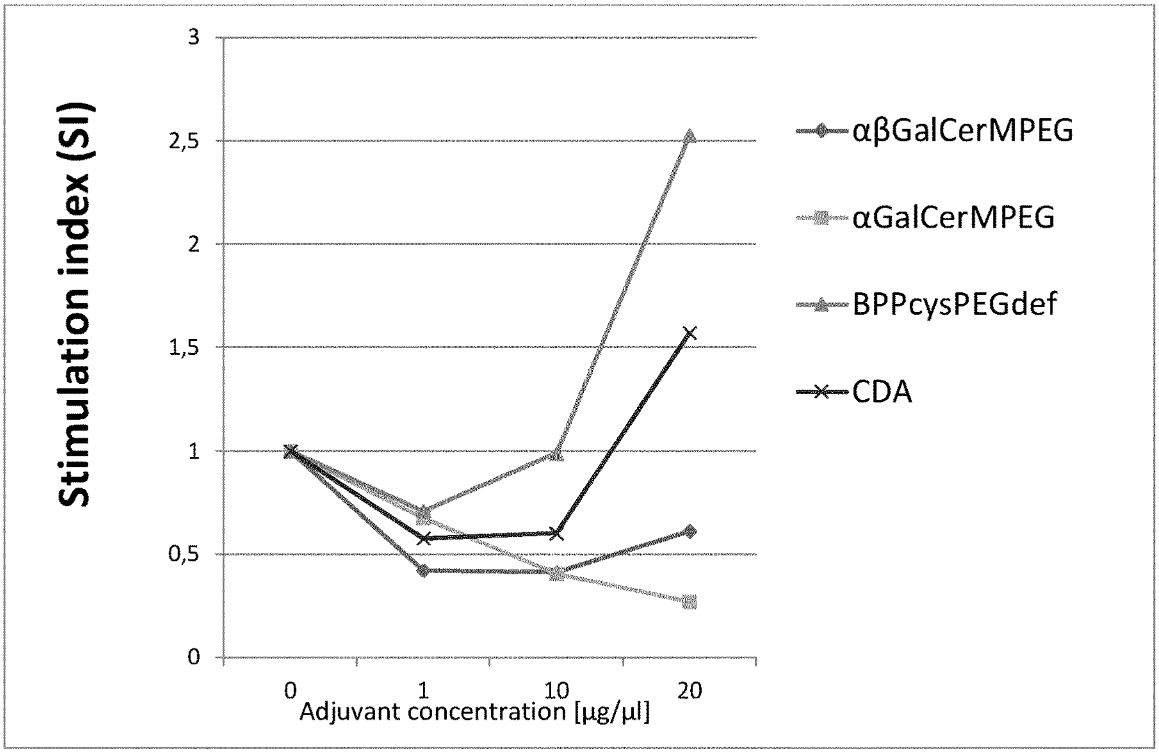

Fig. 2 (cont.)
E
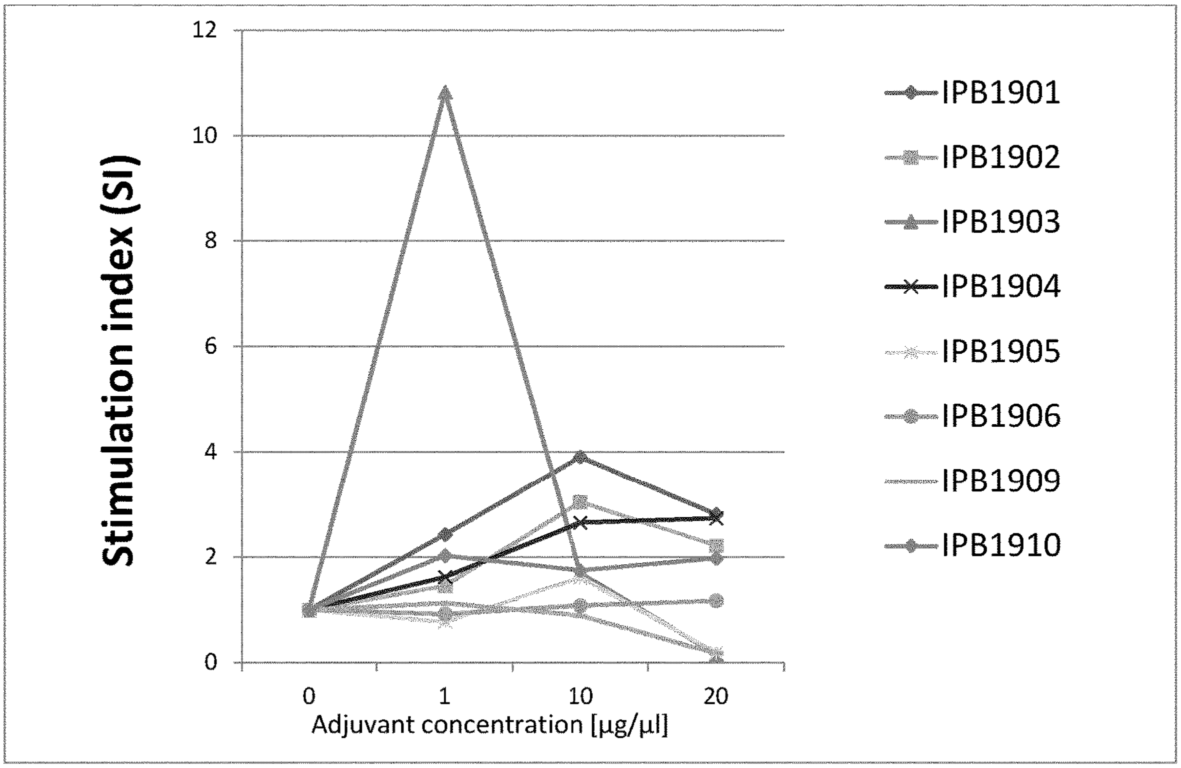
F
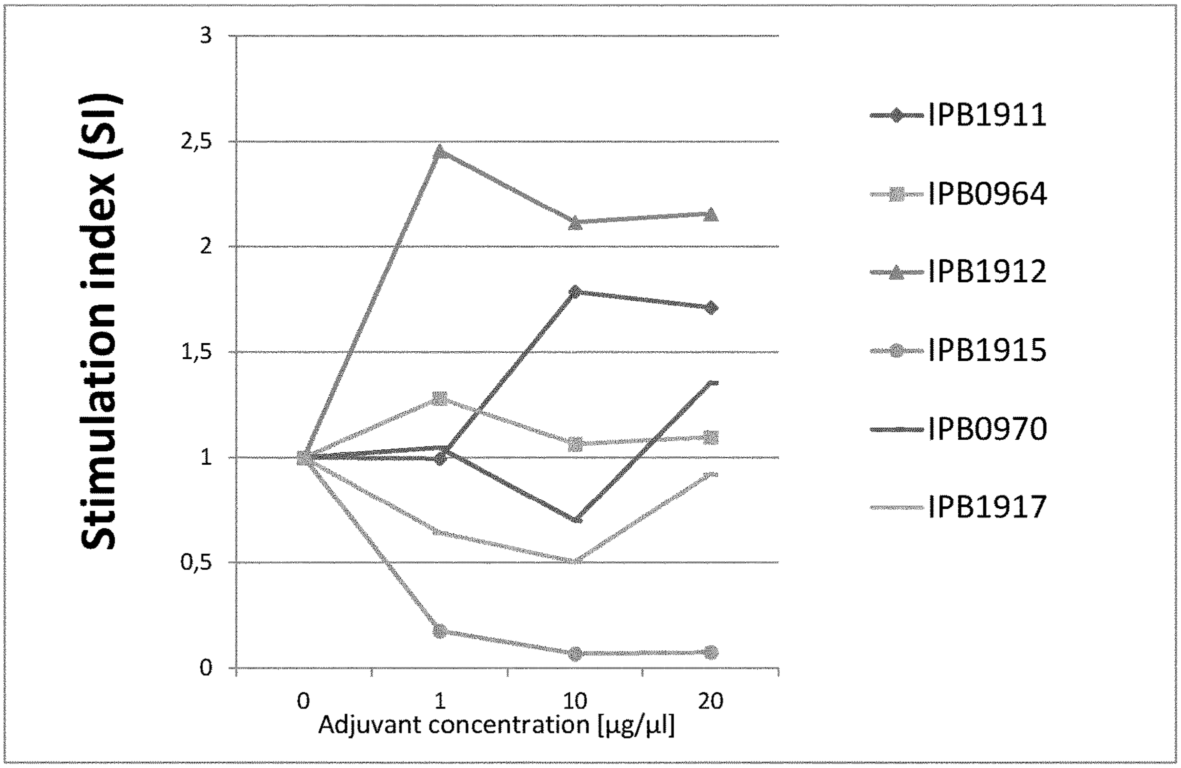

Fig. 4
A
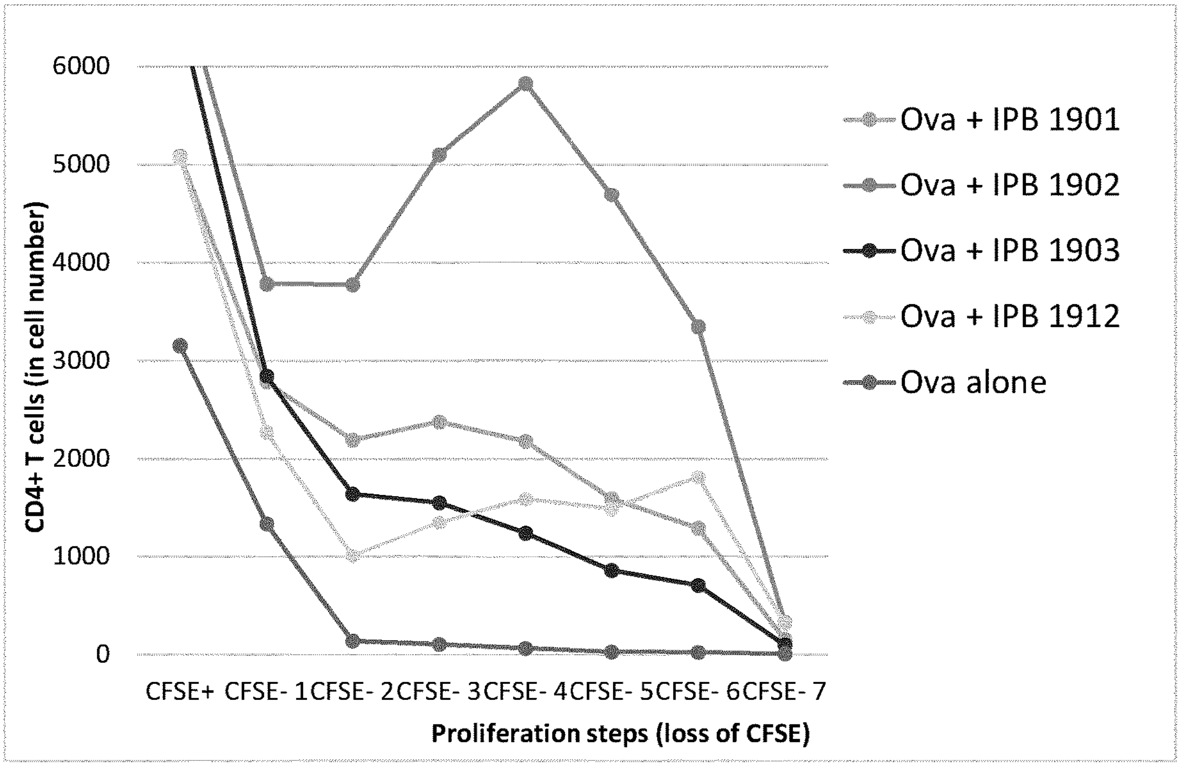
B
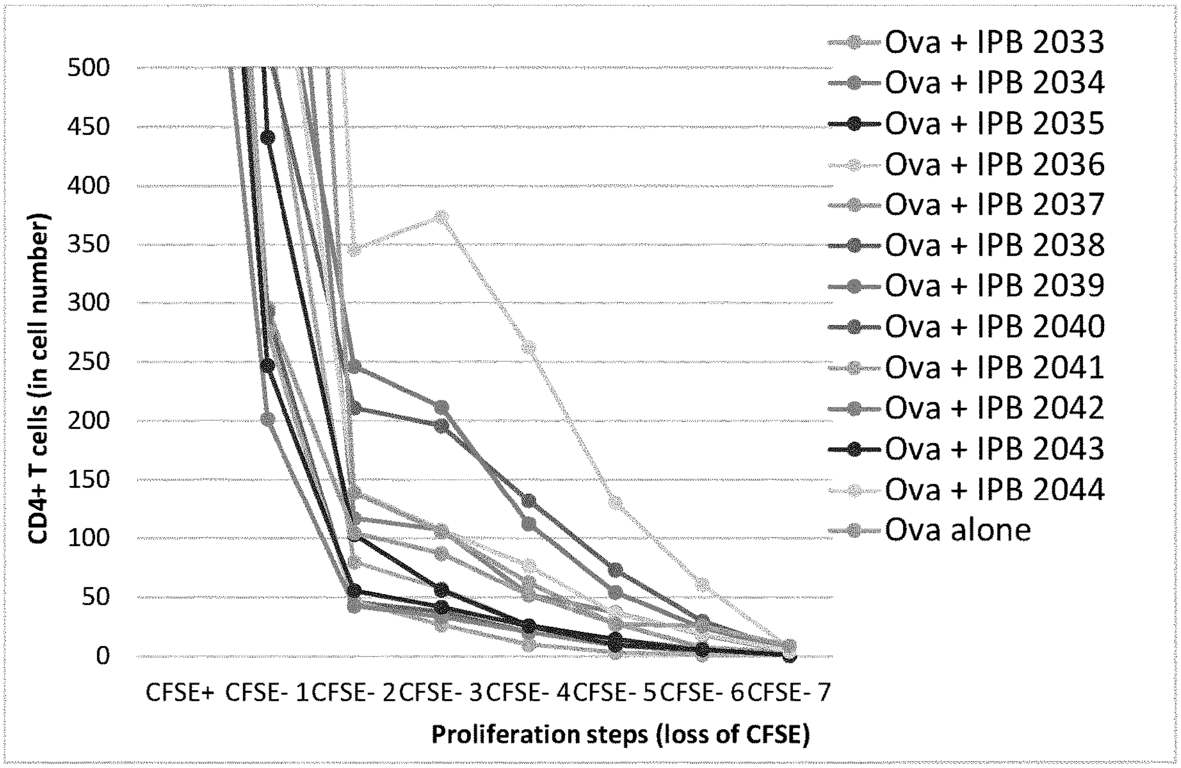

Fig. 4 (cont.)
C
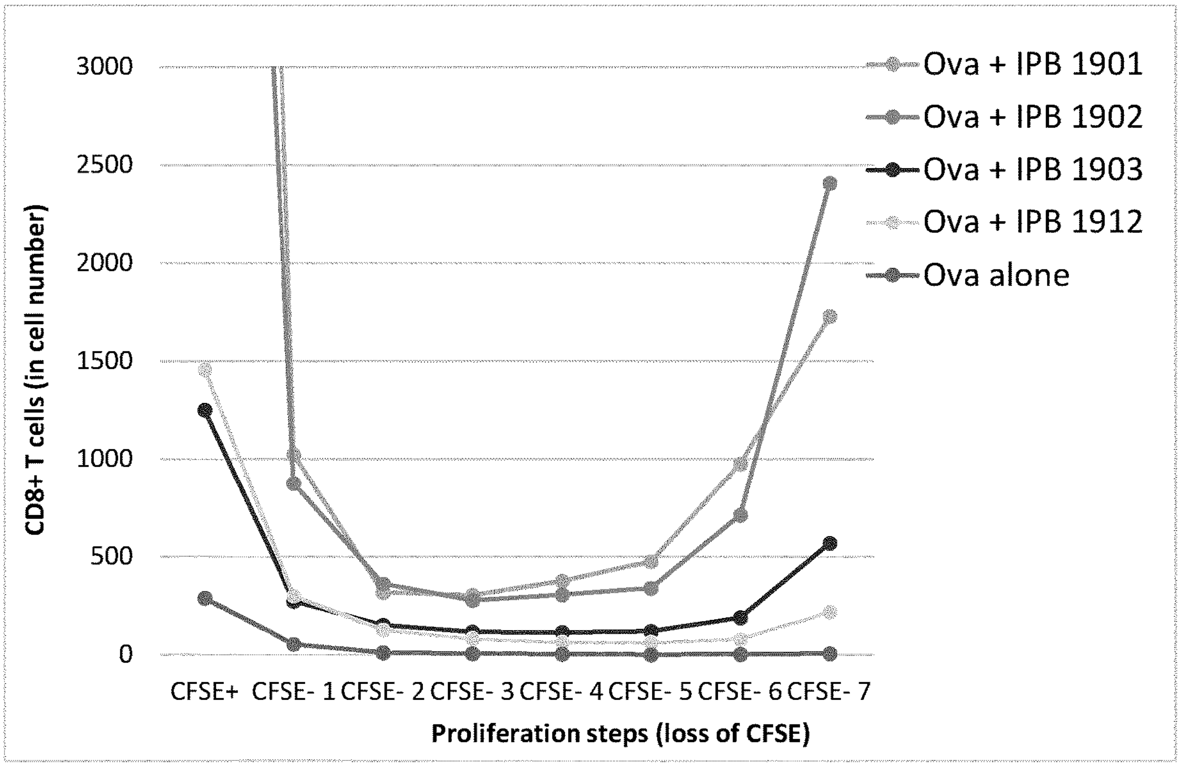
D
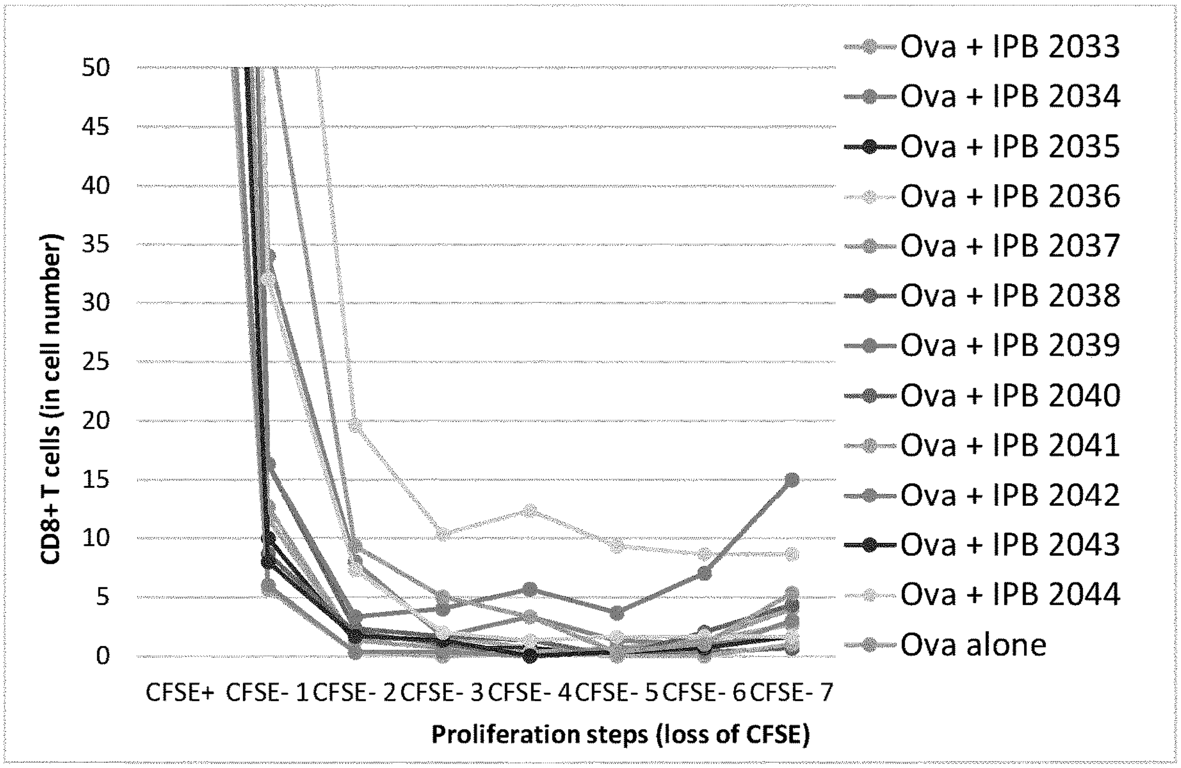

Fig. 5

| Group | Immunization ("dose escalation strategy") | Route | Mice BALB/c | Antigen µg/dose /total | Adjuvant 15 µg/dose |
|---|---|---|---|---|---|
| 1 | Control | i.m. | 3 | - | |
| 2 | Ova alone | i.m. | 3 | 30 µg | |
| 3 | Ova + c-di-AMP | i.m. | 3 | 30 µg | |
| 4 | Ova + aßGalCerMPEG | i.m. | 3 | 30 µg | |
| 5 | Ova + IPB 2033 | i.m. | 3 | 30 µg | |
| 6 | Ova + IPB 2034 | i.m. | 3 | 30 µg | |
| 7 | Ova + IPB 2035 | i.m. | 3 | 30 µg | |
| 8 | Ova + IPB 2036 | i.m. | 3 | 30 µg | |
| 9 | Ova + IPB 2037 | i.m. | 3 | 30 µg | |
| 10 | Ova + IPB 2038 | i.m. | 3 | 30 µg | |
| 11 | Ova + IPB 2039 | i.m. | 3 | 30 µg | |
| 12 | Ova + IPB 2040 | i.m. | 3 | 30 µg | |
| 13 | Ova + IPB 2041 | i.m. | 3 | 30 µg | |
| 14 | Ova + IPB 2042 | i.m. | 3 | 30 µg | |
| 15 | Ova + IPB 2043 | i.m. | 3 | 30 µg | |
| 16 | Ova + IPB 2044 | i.m. | 3 | 30 µg | |
| *total* | | | *48* | | |

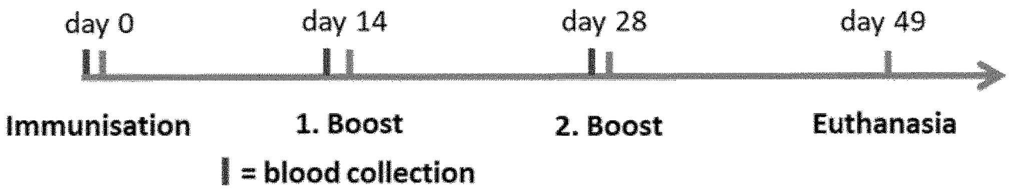

Antigen per dose: 30 µg for Ova

Adjuvant per dose: 15 µg c-di-AMP/aGalCerMPEG/IPB2033-2044

Route: i.m. (50 µl)

Dosages: 3 (on days 0, 14 and 28)

Fig. 6
A
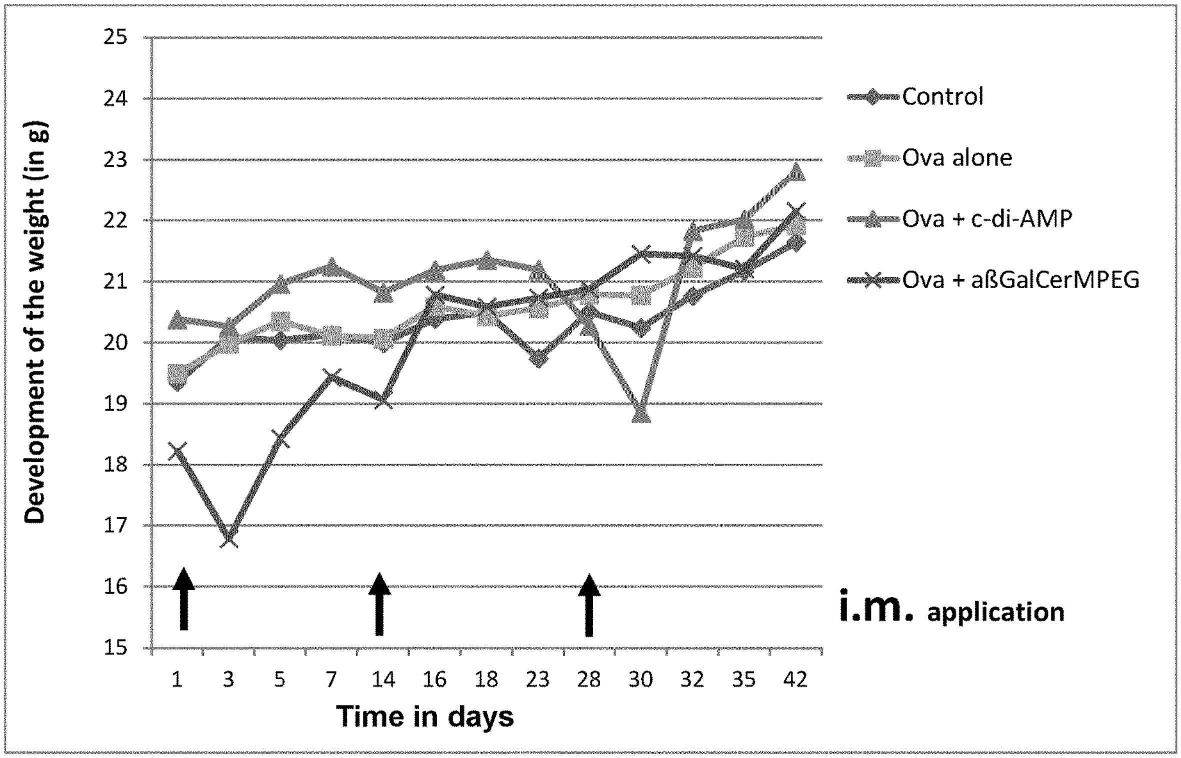
B
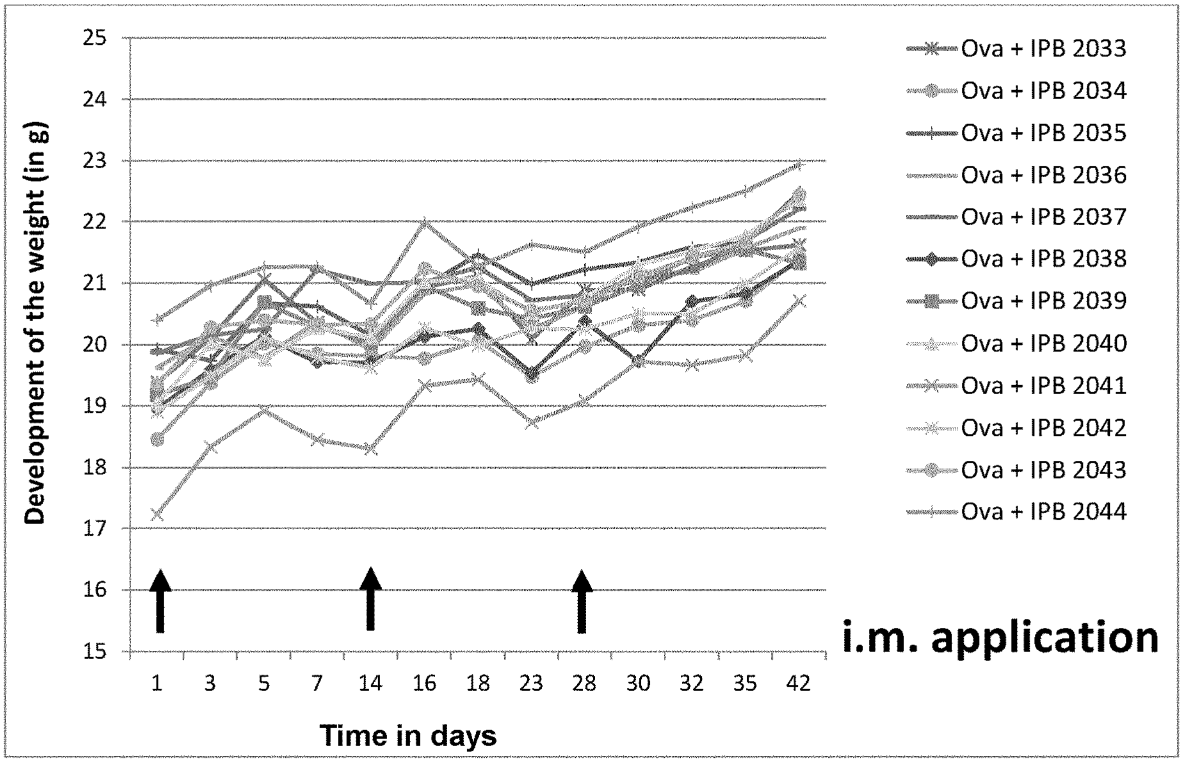

Fig. 8
A
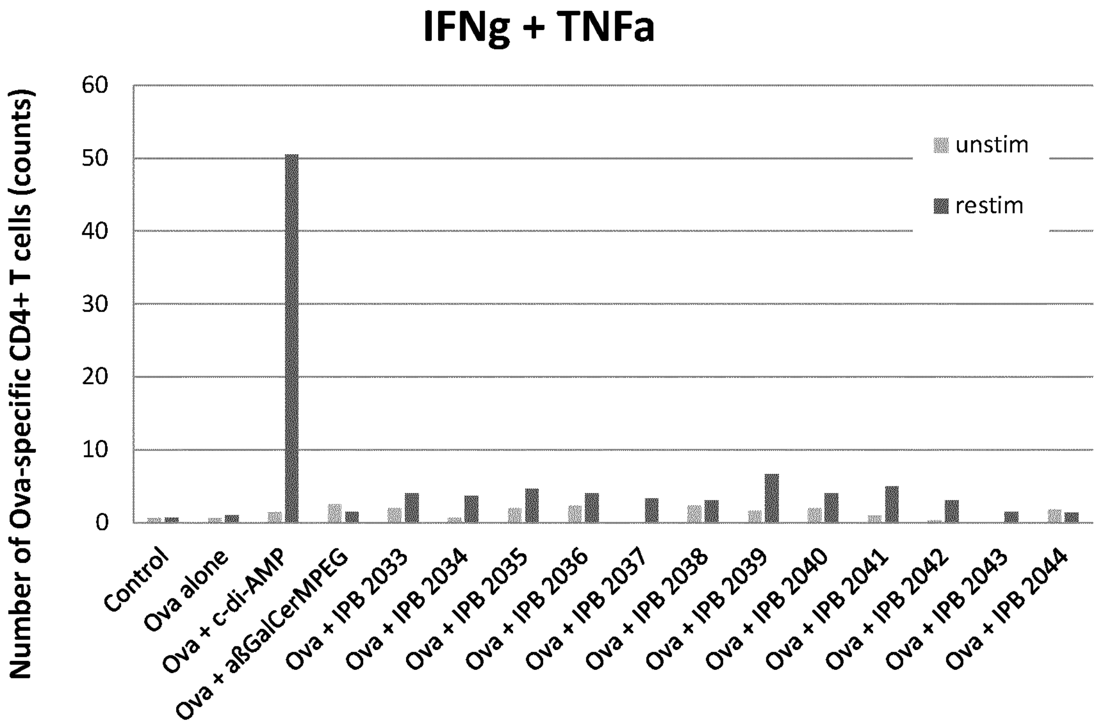
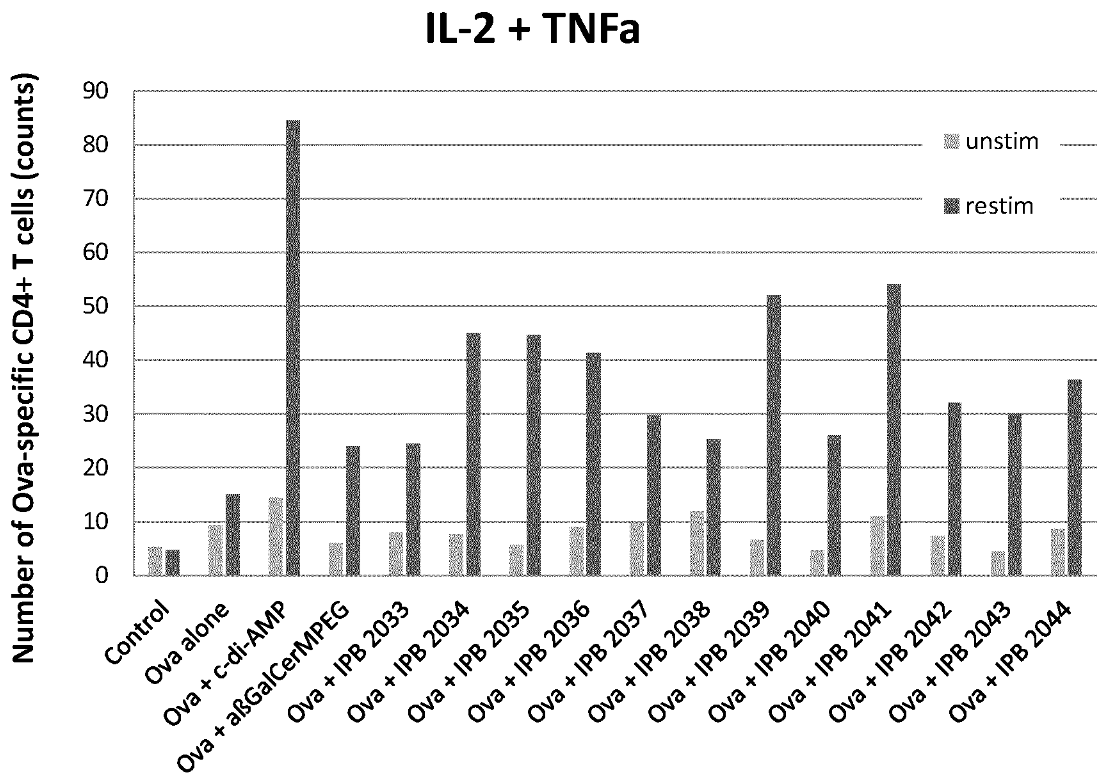

Fig. 8 (cont.)
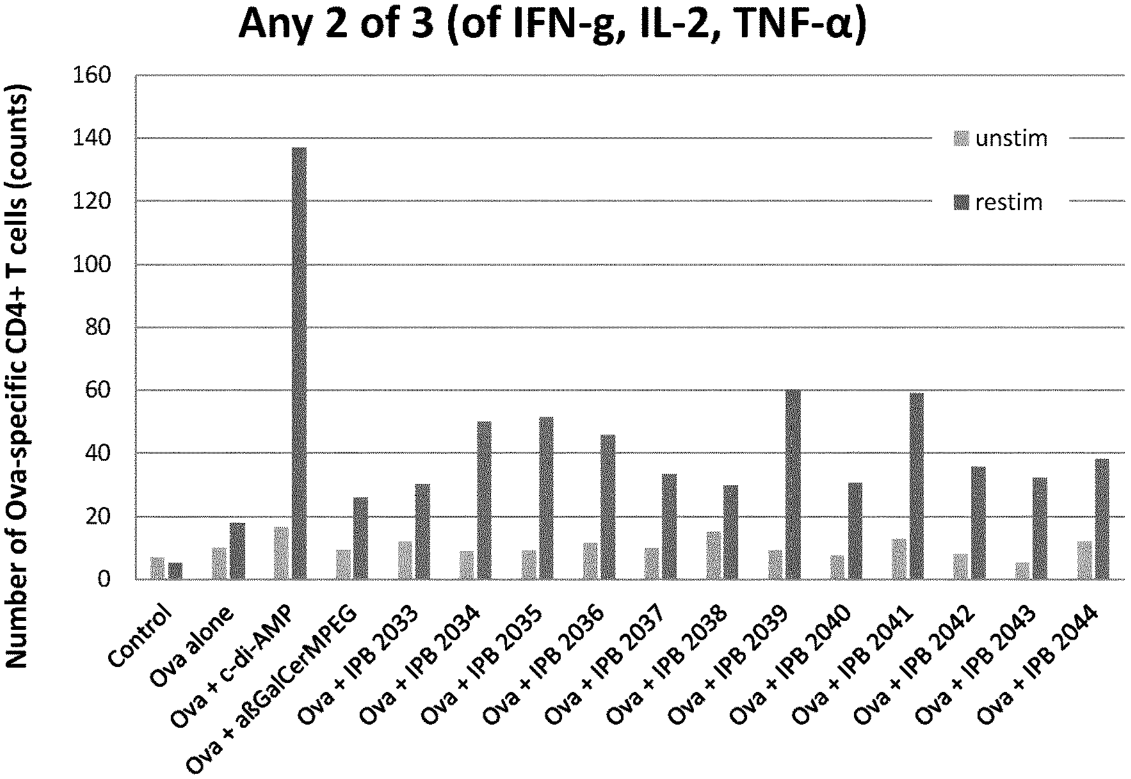
B
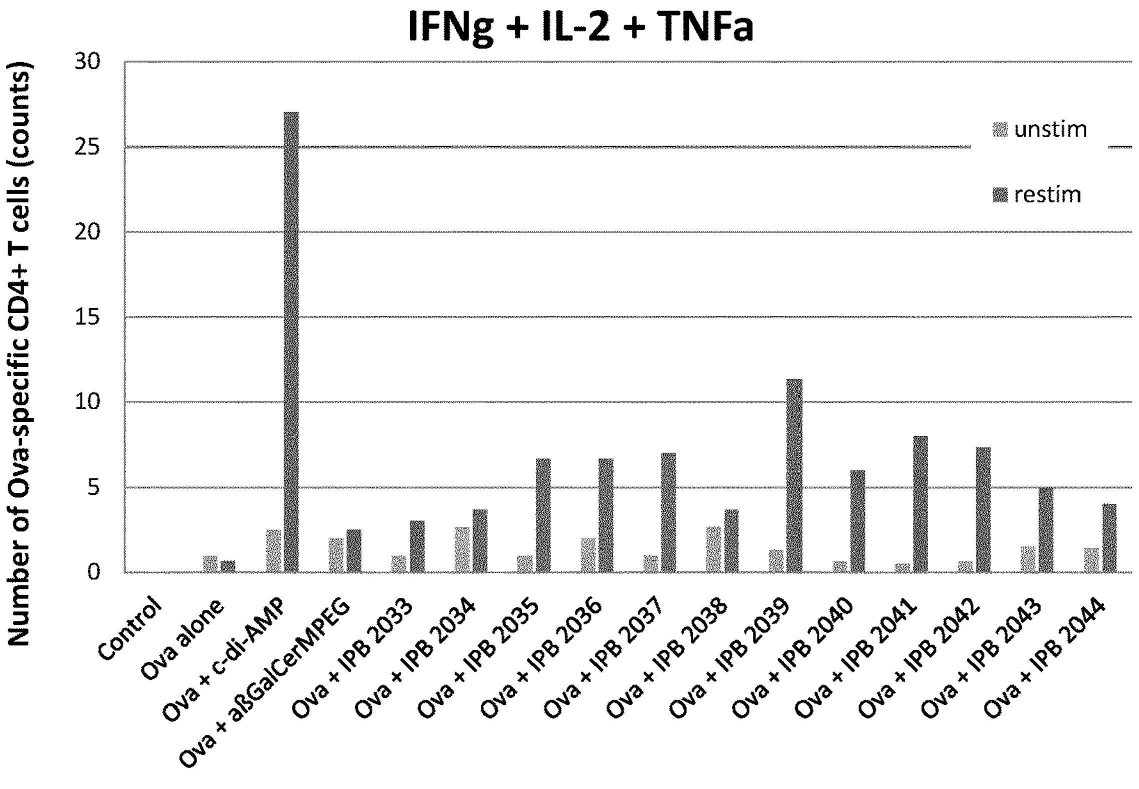

Fig. 9

| Group | Immunization ("dose escalation strategy") | Route | Mice BALB/c | Antigen µg/dose /total | Adjuvant 15 µg/dose |
|---|---|---|---|---|---|
| 1 | Control | i.n. | 3 | - | |
| 2 | Ova alone | i.n. | 3 | 30 µg | |
| 3 | Ova + c-di-AMP | i.n. | 3 | 30 µg | |
| 4 | Ova + aßGalCerMPEG | i.n. | 3 | 30 µg | |
| 5 | Ova + IPB 2033 | i.n. | 3 | 30 µg | |
| 6 | Ova + IPB 2034 | i.n. | 3 | 30 µg | |
| 7 | Ova + IPB 2035 | i.n. | 3 | 30 µg | |
| 8 | Ova + IPB 2036 | i.n. | 3 | 30 µg | |
| 9 | Ova + IPB 2037 | i.n. | 3 | 30 µg | |
| 10 | Ova + IPB 2038 | i.n. | 3 | 30 µg | |
| 11 | Ova + IPB 2039 | i.n. | 3 | 30 µg | |
| 12 | Ova + IPB 2040 | i.n. | 3 | 30 µg | |
| 13 | Ova + IPB 2041 | i.n. | 3 | 30 µg | |
| 14 | Ova + IPB 2042 | i.n. | 3 | 30 µg | |
| 15 | Ova + IPB 2043 | i.n. | 3 | 30 µg | |
| 16 | Ova + IPB 2044 | i.n. | 3 | 30 µg | |
| *total* | | | *48* | | |

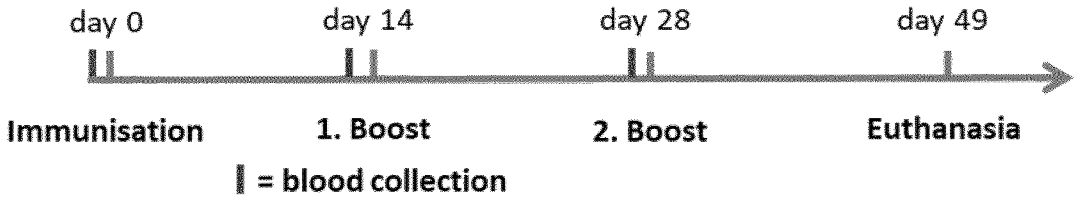

Antigen per dose: 30 µg for Ova

Adjuvant per dose: 15 µg c-di-AMP/aGalCerMPEG/IPB2033-2044

Route: i.n. as mucosal route (20 µl)

Dosages: 3 (on days 0, 14 and 28)

Sampling: 42 / 49

Fig. 10
A
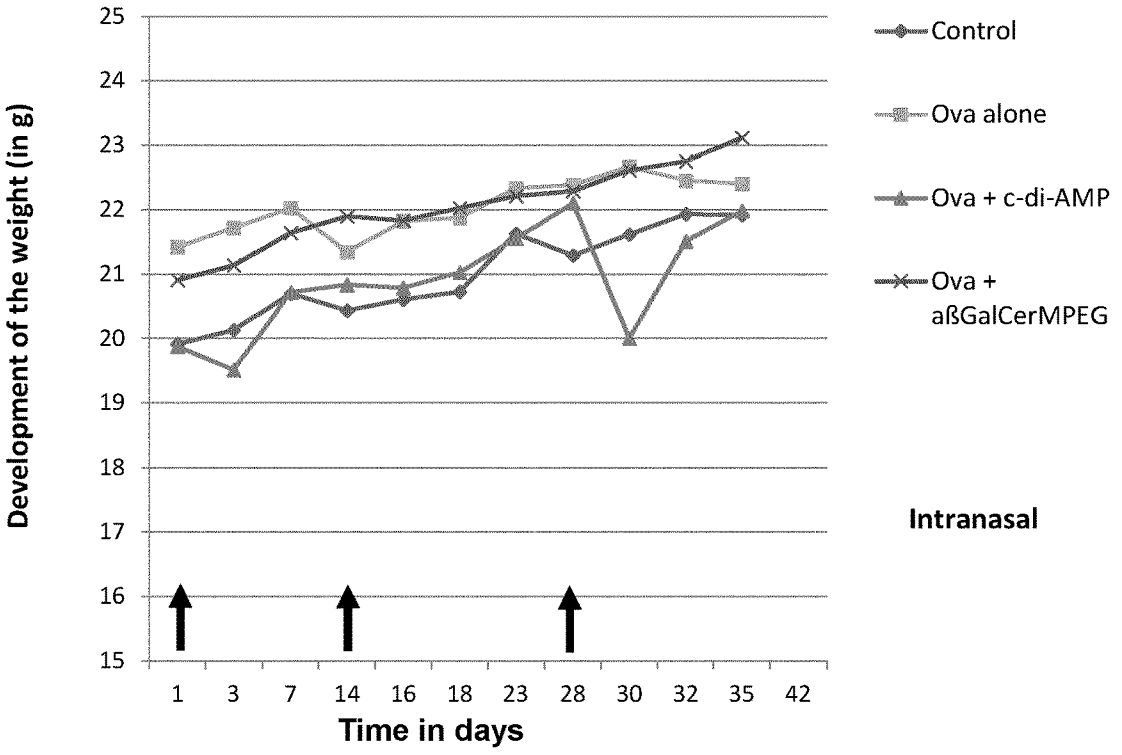
B
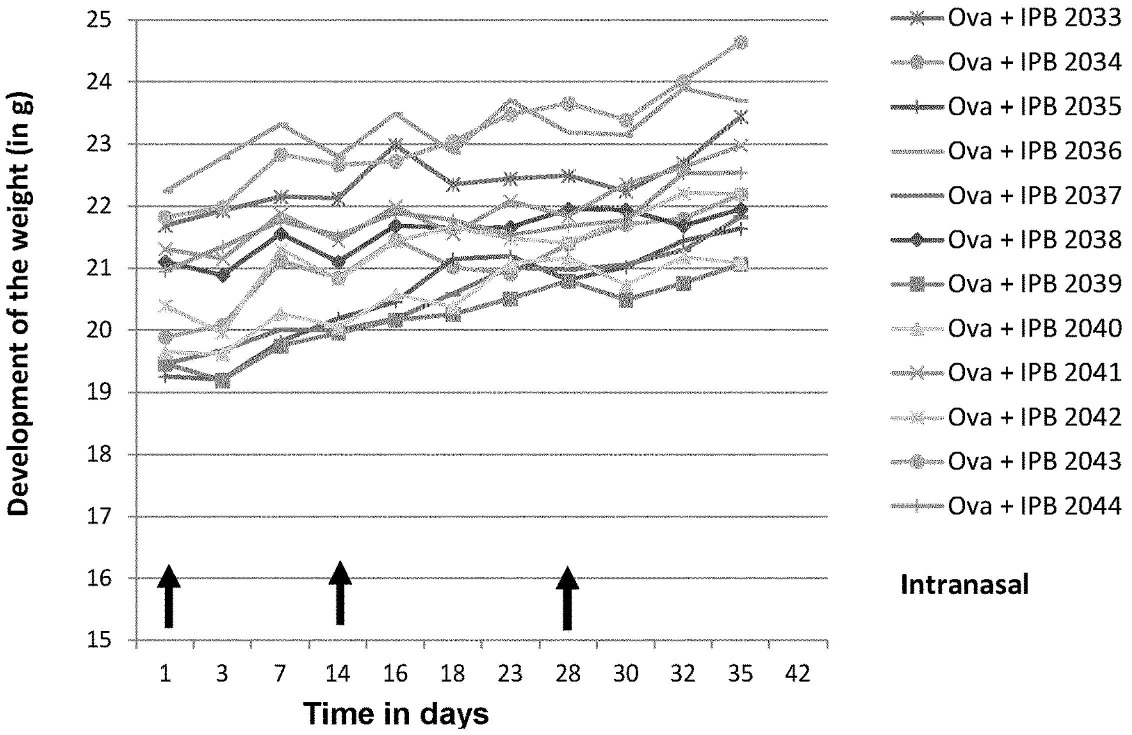

PHYTOSPHINGOSINE DERIVATIVES AS ADJUVANTS IN IMMUNE STIMULATION

The invention relates to the field of phytosphingosine derivatives, corresponding medical uses thereof and methods for their synthesis.

The invention relates therefore to phytosphingosine derivatives, suitable as adjuvants in immune stimulation. The invention further relates to pharmaceutical compositions comprising such compounds and the medical use of said compounds and/or compositions in therapeutic or prophylactic methods of immune stimulation in a subject, and for use in the treatment of a disease, for which stimulation of an immune response in a subject produces a therapeutic benefit.

The invention further relates to the phytosphingosine derivative as described herein for use as an adjuvant in a method of vaccinating a subject. The invention further relates to the phytosphingosine derivative as described herein for use in stimulating antibody production, stimulating an immune response against infection, stimulating an immune response against a cancer, or preventing and/or treating septic shock. The invention further relates to a method for the manufacture of a compound as described herein comprising an Ugi-4-component reaction (Ugi-4CR).

BACKGROUND OF THE INVENTION

The need for more homogeneous and less toxic vaccine formulations has been addressed with the introduction of synthetic and semisynthetic antigens. Nevertheless, as these components fail to induce the necessary immune signals induced by whole-cell vaccines, generally attributed to the stimulation of the innate immune system, they are weak at generating strong immune responses and effective protection. In this context, immune stimulants that trigger different mechanisms of the innate immune system are needed for enhancing the efficacy of vaccines in order to prevent infectious diseases or to enhance immunotherapies directed to tumour-associated processes.

One of the most attractive mechanisms is the activation of a subset of lymphocytes known as invariant natural killer T cells (iNKTs), which provokes the liberation of a plethora of cytokines and the subsequent down-stream activation of dendritic cells (DCs), natural killer (NK) cells, B and T cells. This subset of lymphocytes is usually referred to as a bridge between the innate and the adaptive immune responses and different glycolipids (mainly exogenous) have been described as iNKT activators through their presentation by the non-polymorphic molecule CD1d on different antigen presenting cells (APCs). An overview of natural killer T (NKT) cells is provided in Macho-Fernandez et al, Front. Immunol. 6 (2015) 1.

In 1994, a research group at the Kirin Brewery Co. in Japan discovered that extracts from the marine sponge Age/as mauritanius presented anti-tumour properties in murine models. Later, the glyco sphingolipids responsible of this activity and the structurally optimized analogue KRN7000 were described as potent activators of iNKTs (Morita et al. J. Med. Chem. 38 (1995) 2176; and Natori et al, Tetrahedron. 50 (1994) 2771; see FIG. 1). KRN7000 and derivatives thereof are also described in Chennamadhavuni et al, Cell Chemical Biology 25, 571-584, May 17, 2018.

The activation of iNKTs by this glycolipid is rapidly followed by the simultaneous generation of pro-inflammatory cytokines associated with a Th1-type response (i.e. IFN-γ and TNF) and immunomodulatory cytokines associated with a Th2-type response (i.e. IL-4, IL-5 and IL-13) (refer Guo J, Liu Z. Carbohyd. Res. 452 (2017) 78). KRN7000 has demonstrated a strong adjuvant capability in different antiparasitic (Gonzalez-Aseguinolaza et al. J. Exp. Med. 195 (2002) 617), antiviral (Huang et al. Vaccine 26, (2008) 1807) and anticancer (Kobayashi et al Oncol. Res. 7(1995) 529) formulations under investigation, nevertheless its effectiveness has been limited in phase I trials of several anticancer immunotherapies.

The stimulation of both types of cytokines by KRN7000 may lead to conflicting effects and be detrimental for targeted immunotherapy. Other drawbacks associated to this glycolipid are its low solubility (Ebensen et al J. Immunol. 179 (2007); 2065) and the promotion of T-cell anergy. In this context, the search for new galactosyl ceramide analogues is therefore of significant importance. It would be highly valuable to identify compounds biasing one specific response, e.g. a Th1-type response that can be translated in the treatment of cancer, virus, parasite and bacterial infections or a Th2-type response that can be used for ameliorating certain autoimmune diseases.

Several studies demonstrate that the internalization of glycosphingolipids in APCs as well as their further presentation by CD1d on lipid rafts is one of the major factors influencing a Th1-type response and this fact is structurally related to a higher lipophilicity of the analogues. Thus, compounds having a phenyl ring or other hydrophobic groups at the end of one of the lipid chains such as 7DW8-5 (Padte et al, Clin. Immunol. 140 (2011) 142) elicit a Th1 response. On the other hand, compounds bearing truncated or unsaturated lipid chains such as the OCH (Miyamoto et al, Nature 413 (2001) 531) or the α-GalCer C20:2 (Yu et al. Proc. Natl Acad. Sci. USA 102 (2005) 3383), respectively, elicit a Th2-type response owing to their lower lipophilicity. Other compounds such as the α-C-GalCer (Schmieg et al, J Exp Med. 198 (2003) 1631), that is highly stable owed to the C-glycosidic linkage, elicit a Th1-response.

WO 2007/007946 discloses a vaccine composition comprising an antigen and an effective dose of α-galactosylceramide (α-GalCer) as an adjuvant for the intranasal administration.

US 2005/0192248 discloses methods and compositions for augmenting the immunogenicity of an antigen in a mammal, comprising administering said antigen together with an adjuvant composition that includes a synthetic glycolipid compound. Disclosed therein is KRN7000 and chemical compounds related to KRN7000.

WO 2007/045469 discloses hexosylceramides useful as adjuvants for prophylactic and/or therapeutic vaccination in the treatment of infectious diseases, inflammatory diseases, autoimmune diseases, tumours, allergies as well as for the control of fertility in human or animal populations.

US 2013/217639 discloses phytosphingosine analog compounds that are immunostimulating and activate natural killer T cells, and methods for their preparation.

Known compounds biasing one type of response and the number of modifications performed on the glycosyl ceramide scaffold are however, until the present time, rather limited and identifying novel compounds eliciting dissimilar modes of immune activation would be of great value.

SUMMARY OF THE INVENTION

In light of the prior art, the technical problem underlying the present invention is to provide alternative or improved means for immunostimulation, or adjuvants to immune therapies. A further object of the invention is to provide immunostimulants that enable cross-activation of different immune cells, such as dendritic cells (DCs), natural killer (NK) cells, B and T cells. A further object of the invention is to provide agents for immune stimulation that bias one specific response, e.g. a Th1-type or a Th2-type response. A further object of the invention is to provide novel phytosphingosine derivatives. A further object of the invention is to provide alternative or improved means for synthesizing phytosphingosine derivatives that enable control of the compound properties with respect to a biased immune response, for example a Th1-type or a Th2-type response.

This problem is solved by the features of the independent claims. Preferred embodiments of the present invention are provided by the dependent claims.

The present invention therefore relates to a compound according to formula (I):

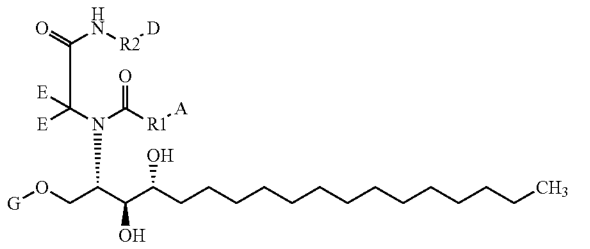

wherein

R1 is a (preferably $C_1$-$C_{30}$, more preferably $C_6$-$C_{25}$) linear or branched alkyl, alkenyl, or alkoxy (preferably an oligomeric- or polymeric-ethylene glycol chain) group, wherein R1 is optionally substituted with -halogen (preferably —F, —Cl), —OH, —$NH_2$, —NHR10, —$N_3$, —C═O; acetal, —$CO_2$H, —$CO_2$R11, —$SO_3$H, —$SO_3$R11, —SH; —SR12, maleimide, —$OPO_3$R13, or wherein R1 is absent, wherein R10, R11 and R12 are, independently, a (preferably $C_1$-$C_{30}$, more preferably $C_6$-$C_{20}$) linear or branched alkyl or alkenyl group, cycloalkyl (preferably cyclohexyl) or an aromatic (or heteroaromatic) group (preferably phenyl), or protecting groups, and R13 is H or a (preferably $C_1$-$C_{30}$, more preferably $C_6$-$C_{20}$) linear or branched alkyl or alkenyl group;

A is H, cycloalkyl (preferably cyclohexyl), an aromatic (or heteroaromatic) group (preferably phenyl), a (preferably $C_1$-$C_{20}$, more preferably $C_1$-$C_{12}$) linear or branched alkyl, alkenyl, or alkoxy, wherein A is optionally substituted with: —OH, —$NH_2$, —NHR10, —$N_3$, —C═O; acetal, —$CO_2$H, —$CO_2$R11, —$SO_3$H, $SO_3$R11, —SH; —SR12, maleimide, —$OPO_3$R13, wherein preferably R1 is absent when A is a cycloalkyl group, or wherein A is an amino acid or a polypeptide, preferably wherein A is a residue with the following formula:

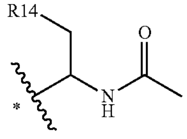

wherein R14 is a side chain of a naturally occurring amino acid;

R2 is a (preferably $C_1$-$C_{30}$, more preferably $C_6$-$C_{25}$) linear or branched alkyl, alkenyl, or alkoxy (preferably an oligomeric- or polymeric-ethylene glycol chain) group, wherein R2 is optionally substituted with -halogen (preferably —F, —Cl), —OH, —$NH_2$, —NHR10, —$N_3$, —C═O; acetal, —$CO_2$H, —$CO_2$R11, —$SO_3$H, —$SO_3$R11, —SH; —SR12, maleimide, —$OPO_3$R13, or wherein R2 is absent, D is H, cycloalkyl (preferably cyclohexyl), an aromatic (or heteroaromatic) group (preferably phenyl), a (preferably $C_1$-$C_{20}$, more preferably $C_1$-$C_{12}$) linear or branched alkyl, alkenyl, or alkoxy, wherein D is optionally substituted with: —OH, —$NH_2$, —NHR10, —$N_3$, —C═O; ═O, $NR10_2$, acetal, —$CO_2$H, —$CO_2$R11, —$SO_3$H, $SO_3$R11, —SH; —SR12, maleimide, —$OPO_3$R13, wherein preferably R2 is absent when D is a cycloalkyl group, or wherein D is an amino acid or a polypeptide, preferably wherein D is a residue with the following formula:

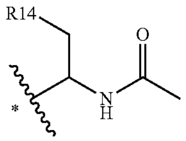

wherein R14 is a side chain of a naturally occurring amino acid;

E is, independently, —H, alkyl (preferably $C_1$-$C_{12}$), -halogen (preferably —F, —Cl), —OH, —$NH_2$, —NHR10, —$N_3$, —C═O; acetal, —$CO_2$H, —$CO_2$R11, —$SO_3$H, —$SO_3$R11, —SH; —SR12, maleimide, or —$OPO_3$R13, wherein E is preferably H;

G is a saccharide, preferably a monosaccharide, such as galactose, glucose, fructose, ribose or xylose, or a disaccharide, such as sucrose, lactose, lactulose, maltose or trehalose, wherein the saccharide is optionally substituted with -halogen (preferably —F, —Cl), —OH, —$NH_2$, —NHR10, —$N_3$, —C═O; acetal, —$CO_2$H, —$CO_2$R11, —$SO_3$H, —$SO_3$R11, —SH; —SR12, maleimide, —$OPO_3$R13, alkyl (preferably $C_1$-$C_{30}$), or ester-, alkyl- or amide-aromatic or heteroaromatic substituents;

wherein optionally two compounds according to formula (I) are covalently bonded to each other at their respective R2 groups, thereby forming R15, wherein R15 is a (preferably $C_1$-$C_{30}$, $C_2$-$C_{30}$, more preferably $C_2$-$C_{20}$) linear or branched alkyl, alkenyl or alkoxy (preferably an oligomeric- or polymeric-ethylene glycol chain) group, and wherein D is absent, or wherein optionally two compounds according to formula (I) are covalently bonded to each other at their respective R1 groups, thereby forming R18, wherein R18 is a (preferably $C_1$-$C_{30}$, $C_2$-$C_{30}$, more preferably $C_2$-$C_{20}$) linear or branched alkyl, alkenyl or alkoxy (preferably an oligomeric- or polymeric-ethylene glycol chain) group, and wherein A is absent.

The present invention therefore relates to pharmaceutically acceptable salts and/or solvates thereof.

The present invention therefore describes the first utilization of isocyanide-based multicomponent reactions for the synthesis of novel α-galactosyl ceramides.

Starting from 1-α-galactosyl phytosphingosine, a variety of phytosphingosine derivatives were synthesized and described herein, which show efficient and superior immunostimulation in the cross-activation of different immune cells. The present invention therefore relates to novel α-galactosyl ceramides obtained by isocyanide-based multicomponent reactions such as the Ugi 4-component reaction (Ugi-4CR). The novel phytosphingosine derivatives of the invention are also referred to as α-GalCer analogues.

According to the present invention, the synthesis of the novel phytosphingosine derivatives described herein preferably utilizes the amino-group of 1-α-galactosyl phytosphingosine as a starting material in isonitrile-mediated multi-component reactions.

Thus, the Ugi 4-component reaction allows the synthesis of galactosyl ceramides containing up to three chains in the ceramide core, preferably three lipid chains, two lipid chains and a third lipophilic or hydrophilic chain (i.e. bearing a PEG/fluorescent tag/different functional groups or being truncated with phenyl/cyclohexyl groups, etc.)

The presence of a third lipophilic chain (such as a lipid chain or cyclohexyl-/phenyl-truncated chain) increases the lipophilicity of the molecules, thus potentially favouring their internalization in the APCs and biasing a Th1-type response.

The presence of one or two hydrophilic chains (such as an ethylene glycol-containing chain) increases the hydrophilicity of the molecules, potentially favouring their direct uptake in the CD1d on APCs and biasing a Th2-type response. These molecules can be further improved to be water soluble and applied as part of intranasal formulations.

Furthermore, the Ugi 4-component reaction allows the synthesis of complex scaffolds such as galactosyl ceramide dimers using bi-functional isocyanides or carboxylic acids. These molecules bear up to four lipophilic chains distributed in two ceramide cores while also containing two carbohydrate cores. On the other hand, this method also allows the synthesis of dimers bearing two lipophilic and two hydrophilic chains.

As can be observed from the disclosure herein, the compounds of the present invention can be tailored in order to induce a particular type (or biased) immune response, depending on the need for a particular kind of response in any given medical setting. The present invention therefore provides agents for immune stimulation that bias towards a specific response, e.g. a Th1-type or a Th2-type response. In this context, the induced immune response is not necessarily completely either a Th1- or Th2-type response, rather the molecule can be tailored to exhibit one type of immune response compared to the other. In some embodiments, the unwanted immune response is at low or negligible levels. In some embodiments, the immune response exhibit both Th1- and Th2-type responses, although one response type is stronger than the other.

In some embodiments, the linkage of two "monomers" leads to a removal of A or D, and a removal of R1 or R2, and introduction of a "linker" as R15 or R18, respectively. In some embodiments, these "linked" compounds are defined by the feature: wherein optionally two compounds according to formula (I) are covalently bonded to each other at their respective R2 groups, thereby forming R15, or wherein optionally two compounds according to formula (I) are covalently bonded to each other at their respective R1 groups, thereby forming R18. In some embodiments, in the "linked" compounds, R1 or R2 of each "Monomer" are removed and replaced by a linker, R15 or R18, as shown in further embodiments and example compounds below.

In some embodiments of formula (I) or other formula described herein, R1 and/or R2 may be alkenyl. In some embodiments, R1 and/or R2 may be substituted with $NH_2$.

In some embodiments A and/or D are a heteroaromatic group, such as biotin. In some embodiments, A and/or D are an aromatic group, such as phenyl. In some embodiments A and/or D are an amino acid or comprise an amino acid or are coupled to an amino acid or peptide group. In some embodiments R1 and/or R2 are an amino acid or comprise an amino acid or are coupled to an amino acid or peptide group.

In some embodiments of formula (I) or other formula described herein, A and/or D are optionally substituted with halogen (preferably —Cl or —F) or alkyl halogen (preferably $CF_3$). For example, R1 and/or R2 may be absent, and A and/or D may be a cyclic group, such as an aromatic group, e.g. phenyl, or a heteroaromatic or a cycloalkyl group, and said cyclic group is substituted with -halogen (preferably —Cl or —F) or alkyl halogen (preferably $CF_3$).

In some embodiments of formula (I) or other formula described herein, the two E groups form a cyclic structure, such as a cycloalkyl or heterocyclic ring structure, including the C atom to which E is attached. In some embodiments the heterocyclic ring structure comprises one or more heteroatoms in the ring, such as N, O and/or S, preferably N and/or O, wherein said N may be optionally substituted, for example the N in the cyclic structure is NH or NR10.

In some embodiments of formula (I) or other formula described herein, G is a monosaccharide, such as galactose, glucose, fructose, ribose or xylose, optionally substituted as disclosed herein. In some embodiments, both E groups are H.

In some embodiments, the invention therefore relates to a compound according to formula (I), or to other formulae as described herein, wherein the relevant groups are defined as follows:

R1 is a (preferably $C_1$-$C_{30}$, more preferably $C_6$-$C_{25}$) linear or branched alkyl, alkenyl, or alkoxy (preferably an oligomeric- or polymeric-ethylene glycol chain) group, wherein R1 is optionally substituted with -halogen (preferably —F, —Cl), alkyl halogen (preferably $CF_3$), —OH, —$NH_2$, —NHR10, —$N_3$, —C═O; acetal, —$CO_2$H, —$CO_2$R11, —$SO_3$H, —$SO_3$R11, —SH; —SR12, maleimide, —$OPO_3$R13, or wherein R1 is absent, wherein R10, R11 and R12 are, independently, a (preferably $C_1$-$C_{30}$, more preferably $C_6$-$C_{20}$) linear or branched alkyl or alkenyl group, cycloalkyl (preferably cyclohexyl) or an aromatic (or heteroaromatic) group (preferably phenyl), or protecting groups, and R13 is H or a (preferably $C_1$-$C_{30}$, more preferably $C_6$-$C_{20}$) linear or branched alkyl or alkenyl group;

A is H, cycloalkyl (preferably cyclohexyl), an aromatic (or heteroaromatic) group (preferably phenyl), a (preferably $C_1$-$C_{20}$, more preferably $C_1$-$C_{12}$) linear or branched alkyl, alkenyl, or alkoxy, wherein A is optionally substituted with: -halogen (preferably —F, —Cl), alkyl halogen (preferably $CF_3$), —OH, —$NH_2$, —NHR10, —$N_3$, —C═O; acetal, —$CO_2$H, —$CO_2$R11, —$SO_3$H, $SO_3$R11, —SH; —SR12, maleimide, —$OPO_3$R13, wherein preferably R1 is absent when A is a cycloalkyl group, or wherein A is an amino acid or a polypeptide, preferably wherein A is a residue with the following formula:

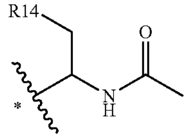

wherein R14 is a side chain of a naturally occurring amino acid;

R2 is a (preferably $C_1$-$C_{30}$, more preferably $C_6$-$C_{25}$) linear or branched alkyl, alkenyl, or alkoxy (preferably an oligomeric- or polymeric-ethylene glycol chain) group, wherein R2 is optionally substituted with -halogen (preferably —F, —Cl), alkyl halogen (preferably $CF_3$), —OH, —$NH_2$, —NHR10, —$N_3$, —C═O; acetal, —$CO_2H$, —$CO_2R11$, —$SO_3H$, —$SO_3R11$, —SH; —SR12, maleimide, —$OPO_3R13$, or wherein R2 is absent, D is H, cycloalkyl (preferably cyclohexyl), an aromatic (or heteroaromatic) group (preferably phenyl), a (preferably $C_1$-$C_{20}$, more preferably $C_1$-$C_{12}$) linear or branched alkyl, alkenyl, or alkoxy, wherein D is optionally substituted with: -halogen (preferably —F, —Cl), alkyl halogen (preferably $CF_3$), —OH, —$NH_2$, —NHR10, —$N_3$, —C═O; ═O, $NR10_2$, acetal, —$CO_2H$, —$CO_2R11$, —$SO_3H$, $SO_3R11$, —SH; —SR12, maleimide, —$OPO_3R13$, wherein preferably R2 is absent when D is a cycloalkyl group, or wherein D is an amino acid or a polypeptide, preferably wherein D is a residue with the following formula:

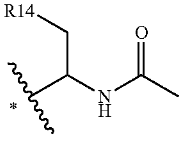

wherein R14 is a side chain of a naturally occurring amino acid;

E is, independently, —H, alkyl (preferably $C_1$-$C_{12}$), -halogen (preferably —F, —Cl), -alkyl halogen (preferably $CF_3$), —OH, —$NH_2$, —NHR10, —$N_3$, —C═O; acetal, —$CO_2H$, —$CO_2R11$, —$SO_3H$, —$SO_3R11$, —SH; —SR12, maleimide, or —$OPO_3R13$, wherein E is preferably H, or wherein the two E groups form a cyclic structure, such as a cycloalkyl or heterocyclic ring structure, including the C atom to which E is attached, and/or wherein when E is a heterocyclic ring structure, said ring comprises one or more of N, O and/or S, preferably N and/or O, wherein if N is present it is optionally present as NR10;

G is a saccharide, preferably a monosaccharide, such as galactose, glucose, fructose, ribose or xylose, or a disaccharide, such as sucrose, lactose, lactulose, maltose or trehalose, wherein the saccharide is optionally substituted with -halogen (preferably —F, —Cl), —OH, —$NH_2$, —NHR10, —$N_3$, —C═O; acetal, —$CO_2H$, —$CO_2R11$, —$SO_3H$, —$SO_3R11$, —SH; —SR12, maleimide, —$OPO_3R13$, alkyl (preferably $C_1$-$C_{30}$), or ester-, alkyl- or amide-aromatic or heteroaromatic substituents;

wherein optionally two compounds according to formula (I) are covalently bonded to each other at their respective R2 groups, thereby forming R15 in place of the R2 groups, wherein R15 is a (preferably $C_1$-$C_{30}$, $C_2$-$C_{30}$, more preferably $C_2$-$C_{20}$) linear or branched alkyl, alkenyl or alkoxy (preferably an oligomeric- or polymeric-ethylene glycol chain) group, and wherein D is absent, or wherein optionally two compounds according to formula (I) are covalently bonded to each other at their respective R1 groups, thereby forming R18 in place of the R1 groups, wherein R18 is a (preferably $C_1$-$C_{30}$, $C_2$-$C_{30}$, more preferably $C_2$-$C_{20}$) linear or branched alkyl, alkenyl or alkoxy (preferably an oligomeric- or polymeric-ethylene glycol chain) group, and wherein A is absent.

In one embodiment, the compound has a structure according to formula (II):

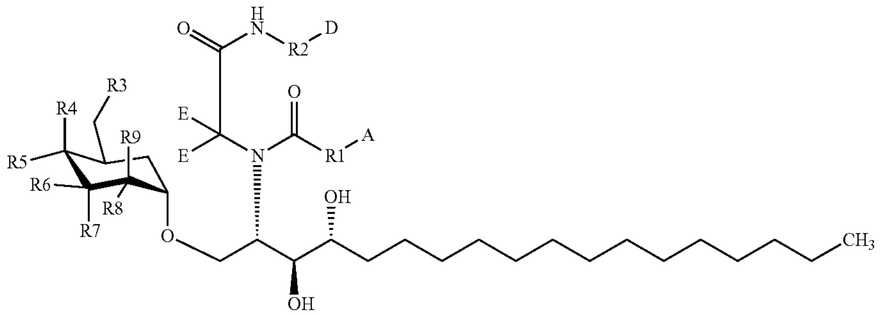

wherein

A, D, R1, R2 and E are as defined above for formula (I), and

R3 is —OH, $OC_1$-$C_{12}$ alkyl, —$CO_2H$, or R19, wherein R19 is —NHCONH—R20, —OCONH—R20, —$OCOC_1$-$C_{12}$ alkyl- or —$NHCOC_1$-$C_{12}$ alkyl-, optionally bound to R20, wherein R20 is an aromatic group, wherein the aromatic group comprises or consists of 1-2 aromatic or heteroaromatic 5- or 6-membered ring structures (more preferably the aromatic group is phenyl);

R4 and R5 are either:

R4 is —H and R5 is —H, —OH, —$OC_1$-$C_{12}$ alkyl, —$NH_2$, or R19, or

R5 is —H and R4 is —H, —OH, —$OC_1$-$C_{12}$ alkyl, —$NH_2$, or R19;

R6 and R7 are either:

R6 is —H and R7 is —H, —OH, —$OC_1$-$C_{12}$ alkyl, —$NH_2$, or R19, or

R7 is —H and R6 is —H, —OH, —$OC_1$-$C_{12}$ alkyl, —$NH_2$, or R19;

R8 and R9 are either:

R8 is —H and R9 is —H, —OH, —$OC_1$-$C_{12}$ alkyl, —$NH_2$, or R19, or

R9 is —H and R8 is —H, —OH, —$OC_1$-$C_{12}$ alkyl, —$NH_2$, or R19.

In one embodiment, R3 to R9 are selected to form galactosyl or glucosyl, GalNAc, or a deoxy sugar group, such as fucosyl, wherein R3 to R9 are preferably selected to form D-galactosyl.

In one embodiment, at least one of R1 and/or R2 is a $C_6$-$C_{30}$ (preferably $C_6$-$C_{25}$) linear or branched alkyl or alkenyl group, or an oligomeric- or polymeric-ethylene glycol chain, optionally substituted with —OH, —$NH_2$, —NHR10, —$N_3$, —C═O; acetal, —$CO_2H$, —$CO_2R11$, —$SO_3H$, —$SO_3R11$, —SH; —SR12, maleimide, —$OPO_3R13$.

In one embodiment, the compound comprises at least 3, preferably 4, $C_6$-$C_{30}$ (preferably $C_6$-$C_{20}$) linear or branched alkyl, alkenyl, or alkoxy (preferably an oligomeric- or polymeric-ethylene glycol chain) groups, optionally substituted as for R1 or R2, as described above.

In one embodiment of formula (I) or (II), applicable to any of the embodiments presented herein, A is H and R1 is $C_{20}$-$C_{30}$ alkyl, preferably $C_{23}$-$C_{25}$, more preferably $C_{25}$.

In one embodiment of formula (I) or (II), applicable to any of the embodiments presented herein, A is H and R1 is $C_5$-$C_{20}$ alkyl, preferably $C_7$-$C_{17}$, more preferably $C_{11}$, $C_{13}$, $C_{15}$ or $C_{17}$.

In one embodiment of formula (I) or (II), applicable to any of the embodiments presented herein, D is H and R2 is alkoxy (preferably $(—CH_2—CH_2—O—)_4$ or $(—CH_2—CH_2—O—)_5$), In one embodiment of formula (I) or (II), applicable to any of the embodiments presented herein, R2 is $C_1$-$C_{10}$ alkyl, preferably $C_2$-$C_5$ alkyl, and D is —$CO_2tBu$, —COOH, Phenyl, —CH—$(OMe)_2$, C═O (or ═O), cyclohexanyl or —$NH_2$.

In one embodiment of formula (I) or (II), applicable to any of the embodiments presented herein, D is an optionally substituted aromatic or heteroaromatic group, comprising one or more optionally conjugated ring structures, for example 2, 3, or 4 (optionally conjugated) 6-membered aromatic, heteroaromatic, cycloalkyl or non-aromatic heterocyclic ring structures.

In some embodiments of formula (I), (II), (Ill) or (IV), applicable to any of the embodiments presented herein, one or more of the following features may be used to define the compounds of the invention. The following features may be combined with the existing substituents disclosed in the context of the formulae presented, or in any given combination of one or more of the following features:

In some embodiments, R1 and/or R2 may be alkenyl.

In some embodiments, R1 and/or R2 may be substituted with $NH_2$.

In some embodiments, A and/or D are a heteroaromatic group, such as biotin.

In some embodiments, A and/or D are an aromatic group, such as phenyl.

In some embodiments, A and/or D are an amino acid or comprise an amino acid or are coupled to an amino acid or peptide group.

In some embodiments, R1 and/or R2 are an amino acid or comprise an amino acid or are coupled to an amino acid or peptide group.

In some embodiments, A and/or D are optionally substituted with halogen (preferably —Cl or —F) or alkyl halogen (preferably $CF_3$). For example, R1 and/or R2 may be absent, and A and/or D may be a cyclic group, such as an aromatic group, e.g. phenyl, or a heteroaromatic or a cycloalkyl group, and said cyclic group is substituted with -halogen (preferably —Cl or —F) or alkyl halogen (preferably $CF_3$).

In some embodiments, the two E groups form a cyclic structure, such as a cycloalkyl or heterocyclic ring structure, including the C atom to which E is attached.

In some embodiments, when the two E groups form a heterocyclic structure, the heterocyclic ring structure comprises one or more heteroatoms in the ring, such as N, O and/or S, preferably N and/or O, wherein said N may be optionally substituted, for example the N in the cyclic structure is NH or NR10.

In some embodiments, G is a monosaccharide, such as galactose, glucose, fructose, ribose or xylose, optionally substituted as disclosed herein.

In some embodiments, both E groups are H.

In one embodiment, the invention relates to a compound with a structure according to formula (III):

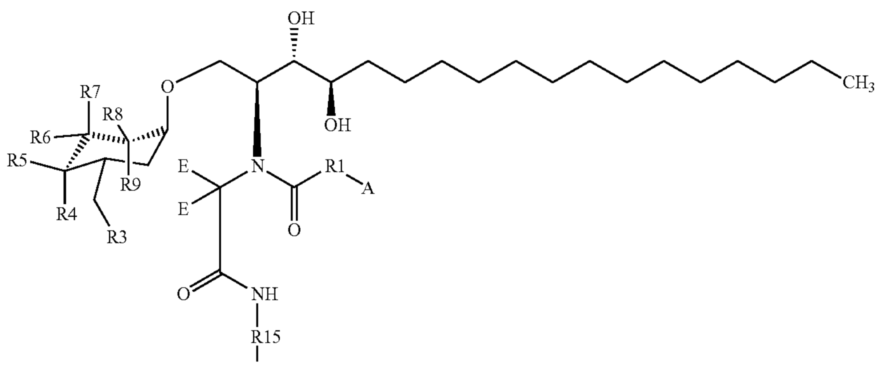

-continued

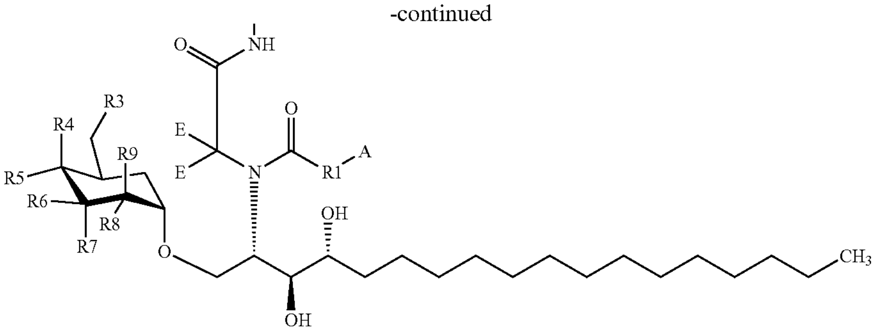

wherein

A, E and R1 are as defined above in formula (I), and R3-R9 are as defined above formula (II), and R15 is a (preferably $C_1$-$C_{30}$, $C_2$-$C_{30}$, more preferably $C_2$-$C_{20}$) linear or branched alkyl, alkenyl or alkoxy (preferably an oligomeric- or polymeric-ethylene glycol chain) group, optionally substituted with —OH, —$NH_2$, —NHR10, —$N_3$, —C═O; acetal, —$CO_2H$, —$CO_2R11$, —$SO_3H$, —$SO_3R11$, —SH; —SR12, maleimide, —$OPO_3R13$, or R15 is —R16PhR17-, wherein Ph is phenyl, or a para/meta di-substituted phenyl ring and R16 and R17 are, independently, a (preferably $C_1$-$C_{30}$, $C_2$-$C_{30}$, more preferably $C_2$-$C_{20}$) linear or branched alkyl or alkenyl group.

In one embodiment, the invention relates to a compound with a structure according to formula (IV):

or R18 is —R16PhR17-, wherein Ph is phenyl, or a para/meta di-substituted phenyl ring and R16 and R17 are, independently, a (preferably $C_1$-$C_{30}$, $C_2$-$C_{30}$, more preferably $C_2$-$C_{20}$) linear or branched alkyl or alkenyl group.

In one embodiment, at least two lipophilic groups are present at R1 and/or R2, wherein said lipophilic groups are $C_6$-$C_{30}$ linear or branched alkyl or alkenyl groups, optionally substituted with —OH, —$NH_2$, —NHR10, —$N_3$, —C═O; acetal, —$CO_2H$, —$CO_2R11$, —$SO_3H$, —$SO_3R11$, —SH; —SR12, maleimide, —$OPO_3R13$.

In one embodiment, at least two hydrophilic groups are present at R1 and/or R2, wherein said hydrophilic groups are an oligomeric- or polymeric-ethylene glycol chain, optionally substituted with —OH, —$NH_2$, —NHR10, —$N_3$,

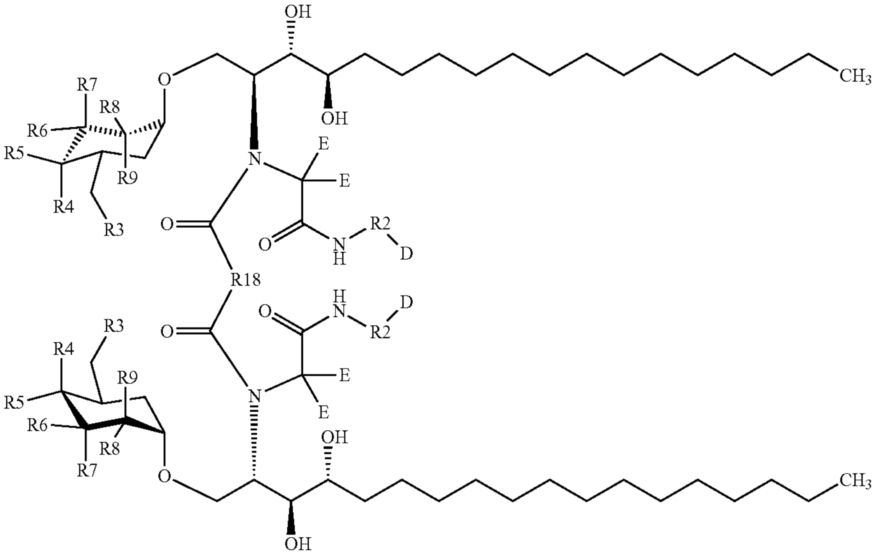

wherein

D, E and R2 are as defined above in formula (I), and R3-R9 are as defined above in formula (II), and R18 is a (preferably $C_1$-$C_{30}$, $C_2$-$C_{30}$, more preferably $C_2$-$C_{20}$) linear or branched alkyl, alkenyl or alkoxy (preferably an oligomeric- or polymeric-ethylene glycol chain) group, optionally substituted with —OH, —$NH_2$, —NHR10, —$N_3$, —C═O; acetal, —$CO_2H$, —$CO_2R11$, —$SO_3H$, —$SO_3R11$, —SH; —SR12, maleimide, —$OPO_3R13$, —C═O; acetal, —$CO_2H$, —$CO_2R11$, —$SO_3H$, —$SO_3R11$, —SH; —SR12, maleimide, —$OPO_3R13$.

In one embodiment of formula (III) or (IV), applicable to any of the embodiments presented herein, A is H and R1 is $C_{20}$-$C_{30}$ alkyl, preferably $C_{23}$-$C_{25}$, more preferably $C_{25}$.

In one embodiment of formula (III) or (IV), applicable to any of the embodiments presented herein, A is H and R1 is $C_5$-$C_{20}$ alkyl, preferably $C_7$-$C_{17}$, more preferably $C_{11}$, $C_{13}$, $C_{15}$ or $C_{17}$.

In one embodiment of formula (III) or (IV), applicable to any of the embodiments presented herein, D is H and R2 is alkoxy (preferably $(-CH_2-CH_2-O-)_4$ or $(-CH_2-CH_2-O-)_5$), In one embodiment of formula (III) or (IV), applicable to any of the embodiments presented herein, R2 is $C_1$-$C_{10}$ alkyl, preferably $C_2$-$C_5$ alkyl, and D is $-CO_2tBu$, $-COOH$, Phenyl, $-CH-(OMe)_2$, C═O (or ═O), cyclohexanyl or $-NH_2$.

In further embodiments, the compound is selected from (compound names are presented below each structure):

IPB002044

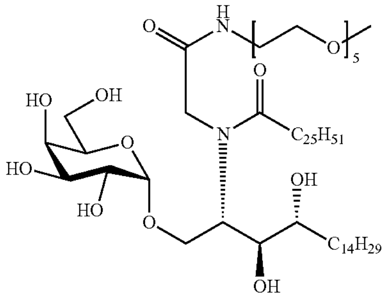

IPB002041

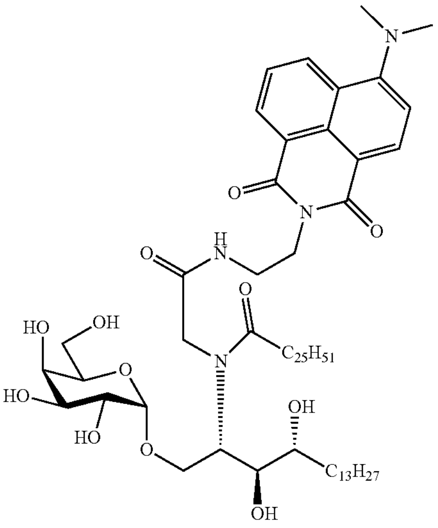

IPB002043

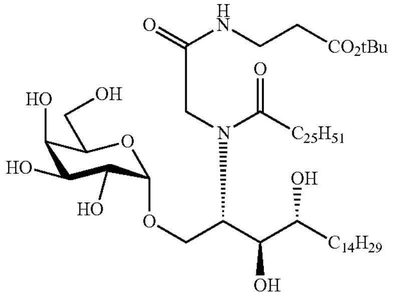

IPB002040

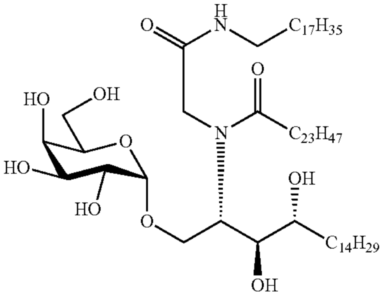

IPB002042

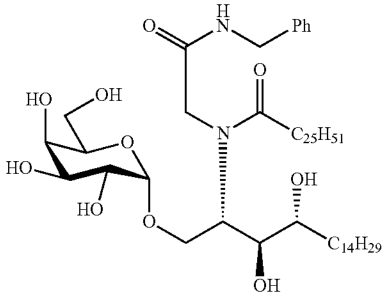

IPB002039

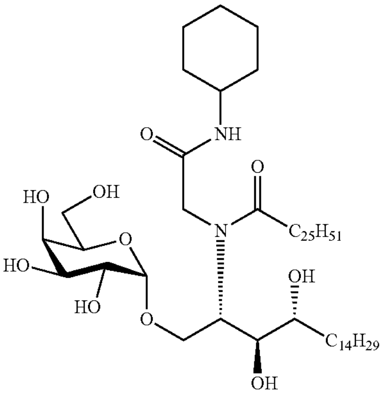

-continued
IPB002035
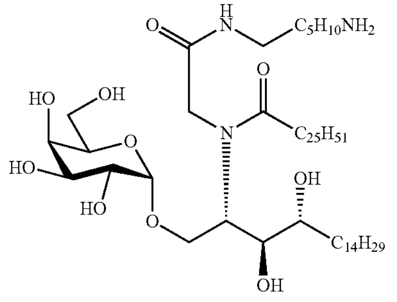
IPB002034
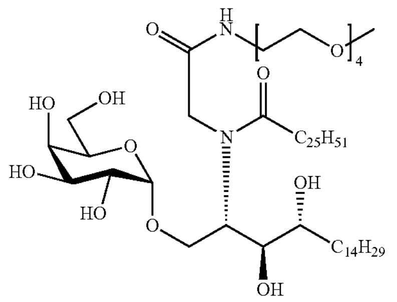
IPB002033
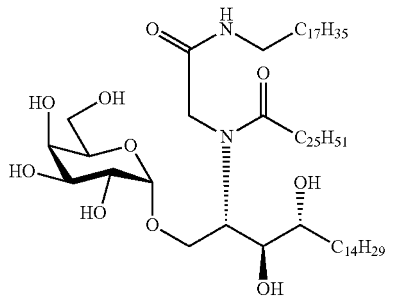
IPB000970
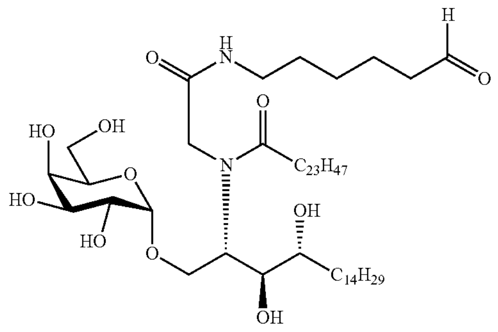
IPB002038
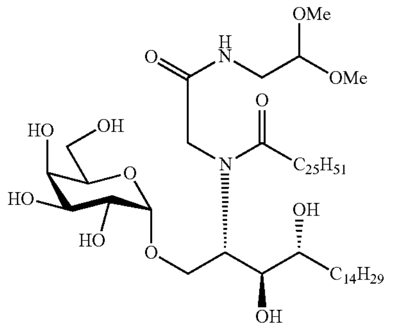
IPB002037
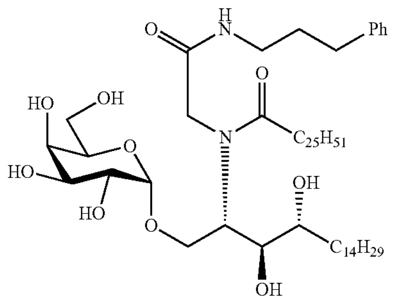
IPB002036
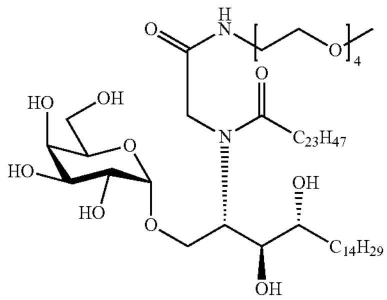
IPB001917
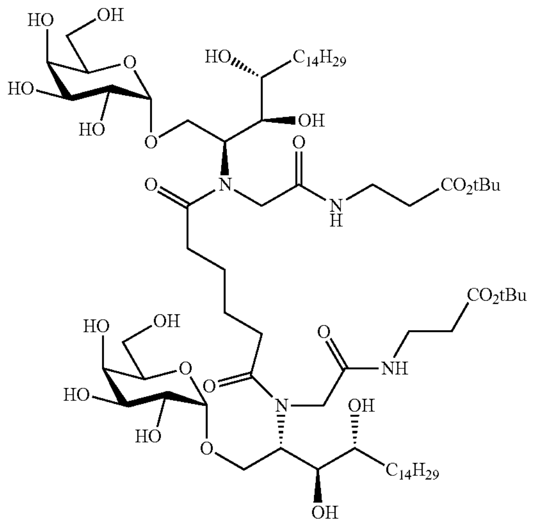

-continued
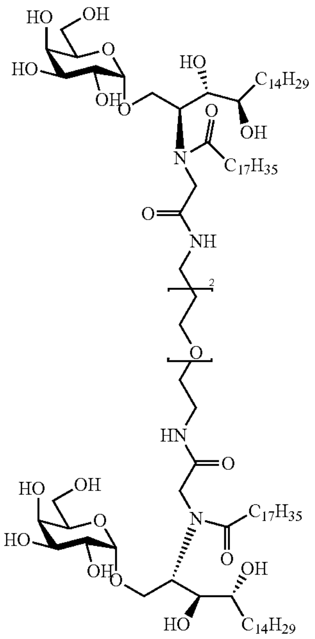
IPB001912
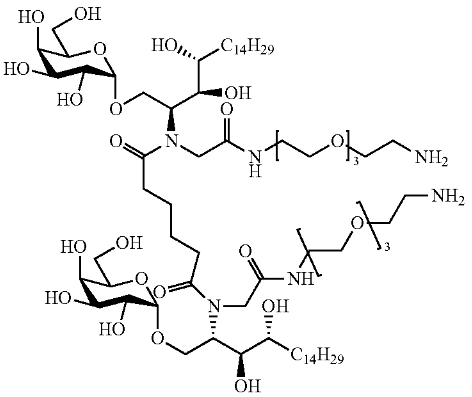
IPB001915
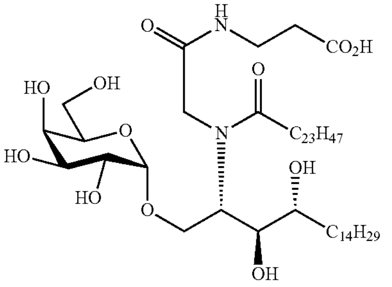
IPB000964
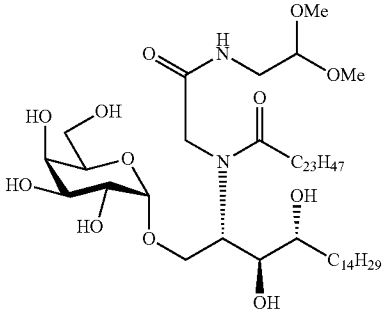
IPB001911
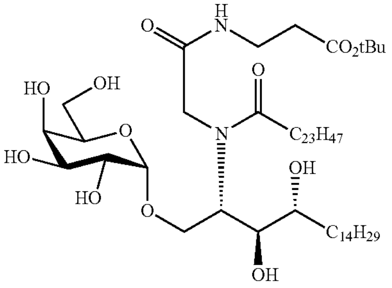
IPB001910
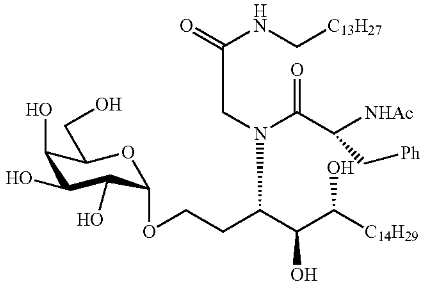
IPB001904
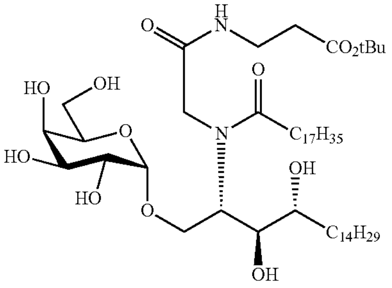
IPB001909
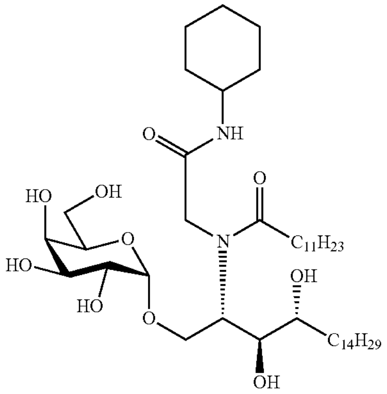
IPB001903

-continued
IPB001906
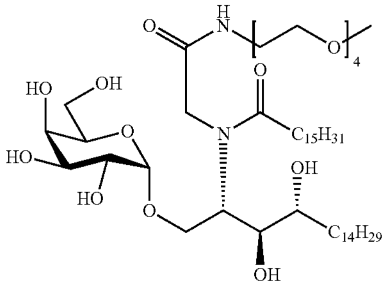
IPB001902
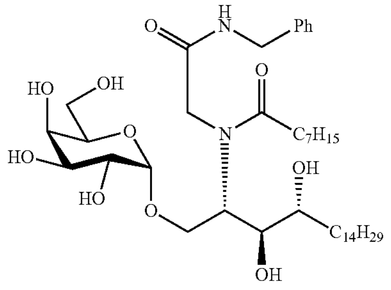
IPB001905
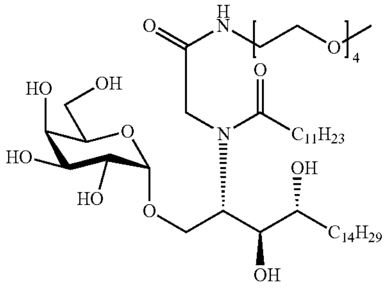
IPB001901
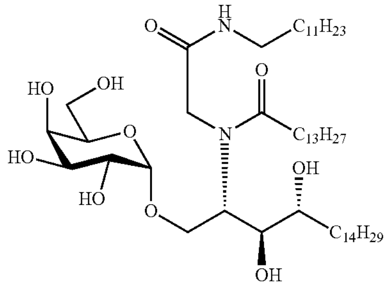
IPB002611
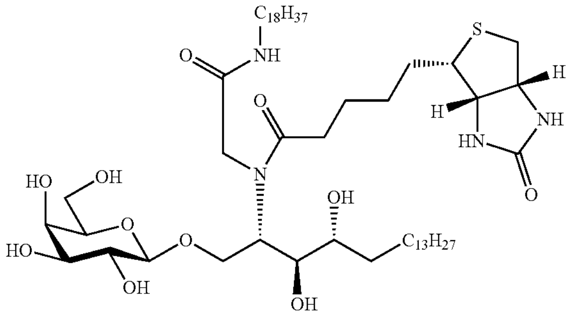
IPB002613
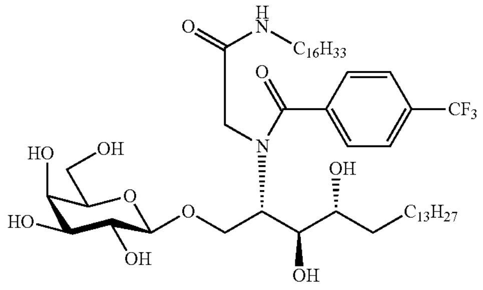
IPB002612
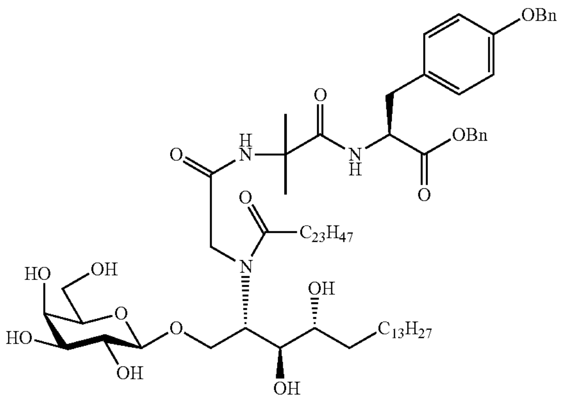
IPB002614
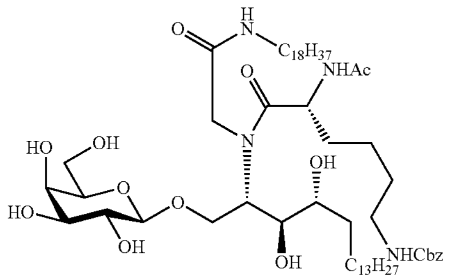

-continued

IPB002615

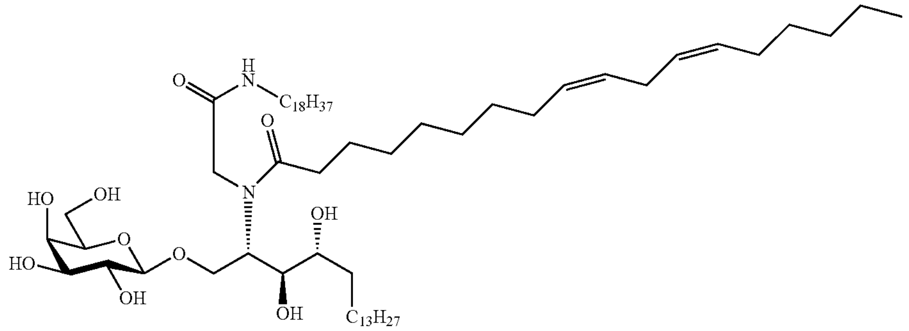

In some embodiments, the chemical compounds are disclosed with or without protecting groups, as may have been employed during synthesis. The invention therefore encompasses the compounds of the chemical formulae disclosed herein, including but not limited to the specific compounds and structures disclosed herein, both with and without the corresponding protecting groups employed and/or demonstrated, independent of the representation of any structure with of without a protecting group.

In one embodiment, the compounds IPB 1901, IPB 1902, IPB 1903, IPB 1904, IPB 1910, IPB 1911, IPB 1913, IPB 1912 show beneficial induction of unspecific proliferation in splenocytes. The substituents of these compounds corresponding to positions A, D, G, R1, R2, E of Formula (I)-(IV) may therefore be used to specify, either individually or in combination, the compounds according to Formula (I)-(IV).

In one embodiment, the compounds IPB 1909, IPB 1905, IPB 1906, IPB 1904 and IPB 1912 show a beneficial capacity to induce antigen specific CD19+ B cell proliferation after interaction with matured Antigen Presenting Cells (APC). The substituents of these compounds corresponding to positions A, D, G, R1, R2, E of Formula (I)-(IV) may therefore be used to specify, either individually or in combination, the compounds according to Formula (I)-(IV).

The compounds IPB 1909, IPB 1903, IPB 1911 and IPB 1910 show a beneficial capacity to induce antigen specific CD4+ T cell proliferation after interaction with matured Antigen Presenting Cells (APC). The substituents of these compounds corresponding to positions A, D, G, R1, R2, E of Formula (I)-(IV) may therefore be used to specify, either individually or in combination, the compounds according to Formula (I)-(IV).

The compounds IPB 1909, IPB 0964, IPB 1911, IPB 1912, IPB 1913 and IPB 1910 show a beneficial effect to induce antigen specific CD8+ T cell proliferation after interaction with matured Antigen Presenting Cells. The substituents of these compounds corresponding to positions A, D, G, R1, R2, E of Formula (I)-(IV) may therefore be used to specify, either individually or in combination, the compounds according to Formula (I)-(IV).

In a further aspect, the invention relates to a pharmaceutical composition comprising a compound as described herein, with a pharmaceutically acceptable carrier. Further examples and details regarding suitable composition components, excipients, forms and the like, are provided below.

In a further aspect, the invention relates to a compound as described herein for use in a therapeutic or prophylactic method of immune stimulation in a subject, preferably for use in the treatment of a disease, for which stimulation of an immune response in a subject produces a therapeutic benefit.

In one embodiment, the invention relates to a compound as described herein for use as an adjuvant in a method of vaccinating a subject.

In one embodiment, the invention relates to a compound as described herein for use in a method of stimulating dendritic cell (DC), natural killer (NK) cell, B cell, T cell or macrophage activity, stimulating antibody production, stimulating an immune response against infection, for example stimulating an immune response against a cancer, or preventing and/or treating septic shock.

The invention therefore relates to a method of inducing an immune response in a subject. In one embodiment, the method relates to treating and/or preventing a medical condition for which stimulation of an immune response in a subject produces a therapeutic benefit. The method preferably comprises the administration of one or more of the compounds described herein to a subject in need thereof, in particular the compounds of Formula (I)-(IV), or the specific compounds listed herein.

In a further aspect, the invention relates to a method for the manufacture of a compound as described herein, comprising an Ugi-4-component reaction (Ugi-4CR) followed by deprotection, said reaction comprising:

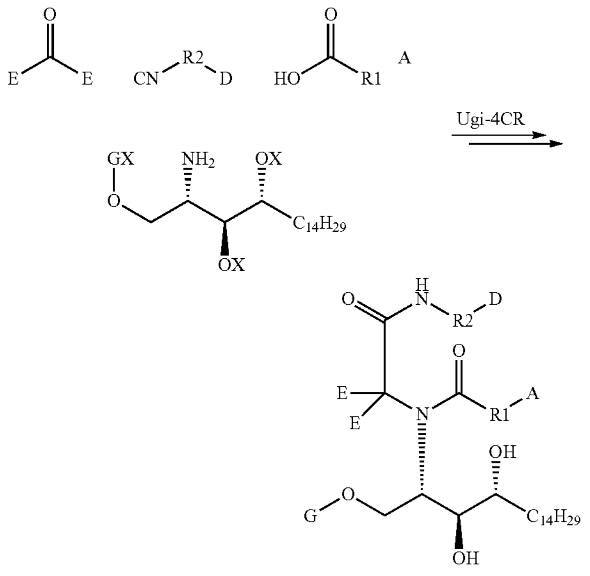

wherein A, D, G, R1, R2, E are as defined above for formula (I) or (II) or (Ill) or (IV), and reactive groups of A, D, G, R1, R2 are protected prior to and during the Ugi-4CR, and X is a protecting group.

In some embodiments, the substituents and/or chemical groups of A, D, G, R1, R2, E are those according to the formulae presented above. The dependent embodiments of the compound descriptions, for example for formula (I) or (II) or (III) or (IV), as presented herein, may also be applied to characterization of the method. A skilled person is aware of how the chemical groups as described herein may be incorporated into the reaction scheme in order to obtain the compounds of the present invention.

The features of the compounds as described herein may therefore be applied to the method of the invention, and vice versa.

Ugi-4CRs are as such known in prior art methods of synthesis and may be applied by a skilled person to the methods of the present invention. According to The Logic of Chemical Synthesis (Corey et al, Wiley NY 2005) and Dömling et al (Bioorg. Med. Chem. Lett. 2000, 10, 1701-1705), various advantages are obtained through the synthesis of the compounds, using a 4CR. By avoiding multiple steps in the synthesis reaction, higher yields are obtained, and more complex synthetic modifications are possible in fewer steps. Using multiple step reactions, for example an about 80% yield may be obtained from each step, i.e. over 4 steps a final yield of about 41% may be obtained. Over 4 steps, the yield is therefore significantly reduced. In contrast, a 4CR enables in one reaction an e.g. about 80% yield, therefore increasing total yield in the chemical synthesis.

To the knowledge of the inventors, no prior disclosure has been suggested applying 4CR methods, such as Ugi-4CR, in preparing phytosphingosine derivatives. In addition to the novelty of the structures described herein, the method represents an advantageous novel approach towards synthesis of phytosphingosine derivatives.

In some embodiments, the Ugi 4-component reaction follows the basic scheme of:

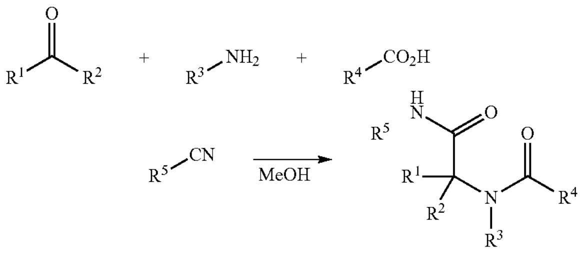

In some embodiments, the synthesis of the compounds described herein follows the generalized scheme of:

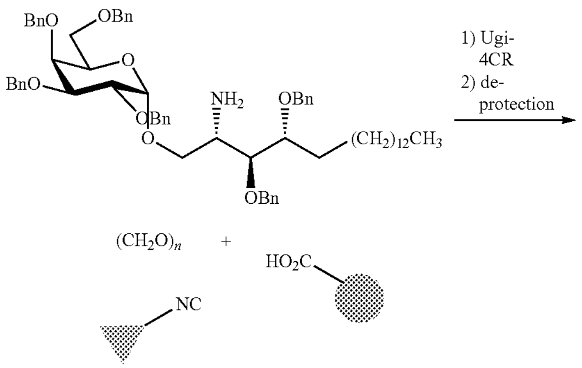

-continued

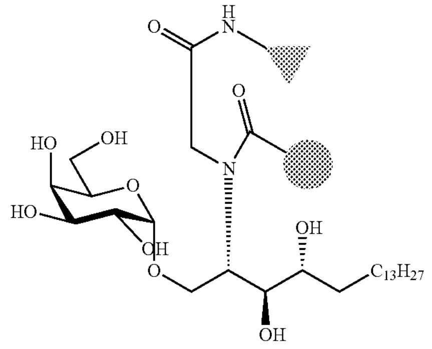

deprotection: 10% Pd/C, 10% $HCO_2H$/THF

In some embodiments, the general scheme employed in the synthesis is as follows:

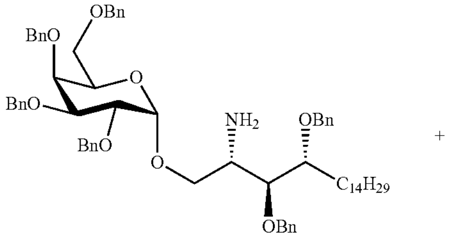

1

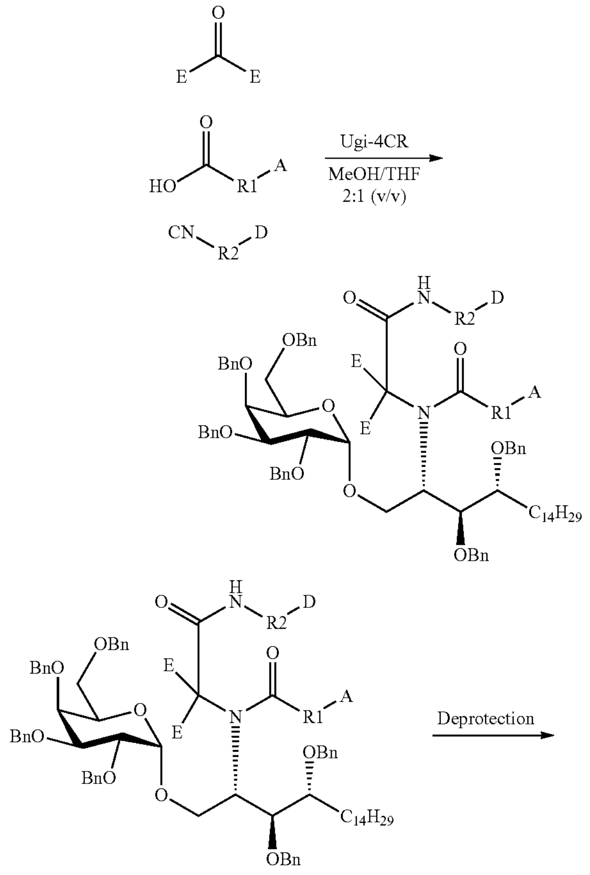

-continued

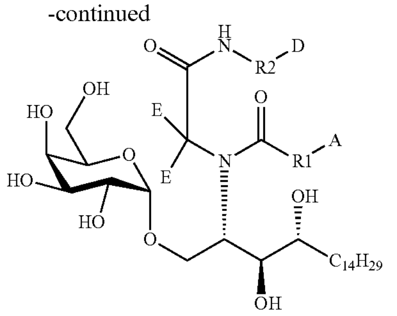

In some embodiments, the substituents and/or chemical groups of A, D, R1, R2, E are those according to the formulae presented above. The dependent embodiments of the compound descriptions, for example for formula (I) or (II) or (III) or (IV), as presented herein, may also be applied to characterization of the method.

Further details, examples and preferred method steps of the synthesis method are presented in detail below.

DETAILED DESCRIPTION OF THE INVENTION

Medical Use:

The present invention is generally concerned with the provision of new compounds as depicted in formula (I)-(IV) or salts or solvates thereof, useful as adjuvants. Furthermore, the present invention relates to new pharmaceuticals comprising at least one of the compounds according to formula (I)-(IV) as described herein with pharmaceutically acceptable carrier(s), optionally together with additional active ingredients. One additional active ingredient is an antigen, to which it is intended that an immune response is generated and enhanced by the compounds of the present invention.

That is, the present invention relates to the provision of the use of specific compounds useful as adjuvants in therapeutic or prophylactic vaccination. Said compounds are useful as systemic and are particularly useful as mucosal adjuvants being applied via the mucosa of the individual.

As used herein, the term "adjuvant" means substances which are added and/or co-formulated in an immunization to the active antigen, i.e. the substance which provokes the desired immune response, in order to enhance or elicit or modulate the humoral and/or cell-mediated (cellular) immune response against the active antigen. Preferably, the adjuvant according to the present invention is also able to enhance or to elicit the innate immune response.

In some embodiments, the compounds as described herein are administered, for example with an antigen, together with a delivery system. As used herein, the term "delivery system" refers to a system that is more inert and has less immunomodulatory effects than adjuvants and which can protect and deliver the vaccine to the site of interest through the site of administration. In particular, the delivery system allows for more efficient presentation of the antigen to the immune system. Examples of delivery systems are virus or virus-like particle, ISCOM, nanoparticles, microparticles, liposomes, virosomes and virus-like particles.

In some embodiments, the compounds as described herein are pegylated. As used herein, the term "pegylated" refers to the conjugation of a compound moiety with conjugate moiety(ies) containing at least one polyalkylene unit. In particular, the term pegylated refers to the conjugation of the compound moiety with a conjugate moiety having at least one polyethylene glycol unit.

In some embodiments, the adjuvant can be administered to a mucosal surface. As used herein, the term "mucosal" refers to mucosal surface from the body such as the nasal, oral, gastro-enteric, rectal, urinary, conjunctival, glandular, e.g. mammary gland, epithelial mucous.

In some embodiments, the compounds as described herein are administered in combination with an antigen, for example an antigen to which an immune response should be stimulated. As used herein, the term "antigenic structure" or "antigen" refers to a structure capable of causing a cellular or humoral immune response. The antigenic structure, also known as epitope is the part of the antigen, which is presented by the MHC or MHC like molecules. Further, the epitope or antigenic structure represents the part of an antigen recognized by antibodies directed against said antigen.

In some embodiments, the compounds described herein modulate the immune response. As used herein, the term "modulate an immune response" refers to any change of the present state of the immune response. Preferably, the modulation relates to a stimulation or enhancement of an immune response.

The immune response may be modulated insofar that the response is elicited or a pre-existing immune response is enhanced which may include decreasing specific aspects of the immune response, e.g. the immune response may be modulated by shifting the immune response from a more humoral to a more cellular immune response or vice versa. Further, the immune response may be modulated by switching or redirecting the response from a Th-1 to Th-2 or Th-3 response or vice versa. In addition, the modulation of the immune response may encompass the activation or enhancement of the innate immune response.

The compound(s) according to the formula (I)-(IV) or salts or solvates thereof is/are preferably present in a preparation with the active vaccination component (e.g. the antigen) which is suitable and provided for intranasal, intra-NALT (nasal associated lymphoid tissue), aerosolized, oral, intrarectal, conjunctival, intravaginal, intraurethral administration or for administration into the milk ducts of the breast. Particularly, the preparation is provided in formulation suitable to be taken up via the respiratory tract or the gastrointestinal tract. Alternatively, the mucosal adjuvant of the invention can be present in a kit for co-administration with a vaccine by one of the aforementioned routes and be adapted therefore where appropriate. That is the vaccine may be administered simultaneously, sequentially or separately with the active vaccination component.

In another embodiment, the present invention relates to methods of treating individuals afflicted with a disease or condition that can be treated by modulating the immune response comprising administering to said individual an effective amount of a pharmaceutical comprising the compounds according to formula (I)-(IV), salts and solvates thereof as defined herein as an adjuvant, preferably as a mucosal adjuvant, together with an active vaccination component, and, optionally, a pharmaceutically acceptable carrier.

Preferably, the method relates to the treatment of individuals afflicted with an infectious disease wherein the infectious disease is produced by an infectious agent selected among those causing human or animal disease at the level of the respiratory tract, gastrointestinal tract, genitourinary tract, osteoarticular system, skin or mucosa.

The compounds or salts or solvates thereof as defined herein are particular useful as mucosal adjuvants for activating or enhancing in vitro and/or in vivo the antigen presenting function of antigen presenting cells for a therapeutic or prophylactic intervention. That means, the adjuvants can stimulate macrophages, can stimulate or enhance the humoral immune response, e.g. enhancing or stimulating the production of antibodies. In addition, the adjuvants can also enhance or stimulate the cellular immune response, e.g. increasing the proliferation of T-cells. Further the compounds of formula (I)-(IV) can not only activate or stimulate components of the adaptive immune system but also of the innate immune system, like activating NK-cells or NKT-cells.

In addition, it is possible to use the adjuvant(s) for ex vivo stimulation in cell culture, e.g. for the production of dendritic cells, etc. These cells obtained by ex vivo stimulation may be used for autologous cell transfer in transplantation or as a cell based vaccine against diseases or conditions, like the diseases and conditions mentioned above, including cancer, autoimmune disease or allergies.

Thus, in case of the use of the compounds or salts or solvates thereof as defined herein as an adjuvant, the pharmaceutical composition according to the present invention is preferably a vaccine, comprising said compounds or salts or solvates thereof as pharmaceutically acceptable adjuvant(s) together with the active vaccination component (e.g. the antigen) and, optionally, a pharmaceutically acceptable carrier, diluent, preservative, adjuvant other than the adjuvant according to the present invention, immunomodulator or excipient. The active vaccination component may be any component suitable to elicit, enhance or modulate an immune response in an individual.

For example, the active vaccination component, the active ingredient of the pharmaceutical composition, comprises at least one or more different antigens in the form of peptides, proteins, polysaccharides, glycolipids or DNA encoding them or bacterial ghost, virosomes, or attenuated vaccines.

Preferentially, the antigen(s) are tumor antigen(s) or antigen(s) derived from infectious agents. The infectious agents include those agents which normally enters individual's organism by crossing the mucous membrane.

The pharmaceutical composition comprising adjuvant(s) according to the present invention, an active vaccination component, optionally additional carrier, diluent, preservative, adjuvant other than the adjuvant according to the present invention, immunomodulator or excipient may additionally contain components, like one or more anti-inflammatory molecules, anti-angiogenic molecules, cytotoxic molecules, immunomodulatory molecules, preferably chemokines, cytokines, CD40 ligand, costimulatory molecules or antibodies or mixtures thereof.

Further, the compounds according to the present invention are useful in tumor therapy including the in vitro generation or in vitro priming of autologous cells for adoptive cell transfer in tumour therapy and transplantation. Moreover, the adjuvants are useful for the induction of cross-tolerance against microbial components, like endotoxins, to protect against septic shock or other severe forms of diseases induced by microbial components.

In addition, the compounds themselves as defined herein may display a pharmaceutical activity, e.g. are to be useful in the prophylaxis and treatment of various diseases and conditions, like cancer, infectious diseases, septic shock, chronic and inflammatory processes, autoimmune diseases, allergies, etc. Hence, the compounds according to formula (I)-(IV) or salts or solvates thereof are also useful for the preparation of a pharmaceutical to prevent or treat infectious diseases, septic shock, cancer, tumours, autoimmune diseases, allergies, or chronic or acute inflammatory processes.

The compounds according to the present invention and salts or solvates thereof, particularly pegylated conjugates, can be used as active ingredients in pharmaceuticals useful for the prevention or treatment of infectious diseases, septic shock, tumours, autoimmune diseases, allergies, or chronic or acute inflammatory processes. In particular, the compounds or salts or solvates thereof are contained in pharmaceuticals useful for preventing or treating cancer and/or tumours, such as melanoma, prostate, breast, colorectal, stomach, throat and neck, pancreatic, cervical, ovarian, bone, leukemia and lung cancer; viral infections, such as, hepatitis B, hepatitis C, human immunodeficiency virus, *Helicobacter pylori*, herpes virus, etc.; bacterial infections, such as tuberculosis, leprosy and listeriosis, and parasitic infections such as malaria.

Various vaccinations are known in the art and typically rely on a sufficient immune response to the antigen. The disease to be vaccinated, the vaccine of which the compounds of the present invention could be co-administered, can in some embodiments, be selected from the non-limiting list of COVID-19 or other SARS-associated disease, Cholera, Dengue, Diphtheria, Hepatitis A, Hepatitis B, Hepatitis E, *Haemophilus influenzae* type b (Hib), Human papillomavirus (HPV), Influenza, Japanese encephalitis, Malaria, Measles, Meningococcal meningitis, Mumps, Pertussis, Pneumococcal disease, Poliomyelitis, Rabies, Rotavirus, Rubella, Tetanus, Tick-borne encephalitis, Tuberculosis, Typhoid, Varicella, Yellow Fever, *Campylobacter jejuni*, Chagas Disease, Chikungunya, Dengue, Enterotoxigenic *Escherichia coli*, Enterovirus 71 (EV71), Group B *Streptococcus* (GBS), Herpes Simplex Virus, HIV-1, Human Hookworm Disease, Leishmaniasis Disease, Malaria, Nipah Virus, Nontyphoidal *Salmonella* Disease, Norovirus, Paratyphoid fever, Respiratory Syncytial Virus (RSV), Schistosomiasis Disease, *Shigella, Staphylococcus aureus, Streptococcus pneumoniae, Streptococcus* pyrogenes, Tuberculosis or a Universal Influenza Vaccine.

Septic shock (namely, infection throughout the body) is a potentially fatal medical condition that occurs when sepsis, which is organ injury or damage in response to infection, leads to dangerously low blood pressure and abnormalities in cellular metabolism. The primary infection is most commonly caused by bacteria, but also may be by fungi, viruses or parasites. It may be located in any part of the body, but most commonly in the lungs, brain, urinary tract, skin or abdominal organs. It can cause multiple organ dysfunction syndrome (formerly known as multiple organ failure) and death. In some embodiments, the adjuvants may be employed in order to prevent septic shock, by preventing sepsis due to vaccination against an infectious human pathogen, or the adjuvant may be employed to enhance the immune system of the patient in order to prevent septic shock occurring, by preventing such serious effects of infection with a human pathogen.

In a preferred embodiment, the present invention relates to a compound for use as an adjuvant in stimulating an immune response against a cancer cell, for example by stimulating an immune response against a cancer antigen. Cancer, according to the present invention, refers to all types of cancer or neoplasm or malignant tumours found in mammals, including leukemias, lymphomas, sarcomas, melanomas and carcinomas. Examples of cancers are cancer of the breast, pancreas, colon, lung, non-small cell lung, ovary, and prostate. Additional cancers according to the present invention include, but are not limited to multiple myeloma, neuroblastoma, breast cancer, ovarian cancer, lung cancer, rhabdomyosarcoma, primary thrombocytosis, primary macroglobulinemia, small-cell lung tumours, primary brain tumours, stomach cancer, colon cancer, malignant pancreatic insulanoma, malignant carcinoid, urinary bladder cancer, premalignant skin lesions, testicular cancer, lymphomas, thyroid cancer, esophageal cancer, genitourinary tract cancer, malignant hypercalcemia, cervical cancer, endometrial cancer, adrenal cortical cancer, and prostate cancer.

Chemical Compounds

With respect to the chemical compounds described herein, the term "alkyl" refers to a branched or unbranched saturated hydrocarbon group of preferably 1 to 30 carbon atoms, such as methyl, ethyl, n-propyl, isopropyl, n-butyl, isobutyl, sec-butyl, pentyl, hexyl, heptyl, and the like. Preferred alkyl groups have 6-25 carbon atoms. Contemplated are 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 carbon atoms, for any given one or more alkyl groups described herein. Any one or more of the alkyl groups described herein may be "substituted alkyls", wherein one or more hydrogen atoms are substituted with a substituent such as halogen, cycloalkyl, alkoxy, hydroxyl, aryl, or carboxyl.

The term "alkenyl" refers to a straight, branched or cyclic hydrocarbon configuration and combinations thereof, including preferably $C_1$-$C_{30}$, more preferably $C_6$-$C_{25}$, that would form if a hydrogen atom is removed from an alkene, for example resulting in ethenyl, or the like.

The term "cycloalkyl" refers to a configuration derived from a cycloalkane by removal of an atom of hydrogen, thereby forming preferably cyclopropyl, cyclobutyl, cyclopentyl, cyclohexyl or cycloheptyl, or the like.

The term "alkoxy" refers to a straight, branched or cyclic hydrocarbon configuration and combinations thereof, including preferably $C_1$-$C_{30}$, more preferably $C_6$-$C_{25}$. Contemplated are 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 carbon atoms, that include an oxygen atom at the point of attachment (such as O-alkyl). An example of an "alkoxy group" is represented by the formula —OR, or —ROR, where R can be an alkyl group, optionally substituted with halogen, aryl, cycloalkyl, halogenated alkyl. Suitable alkoxy groups include methoxy, ethoxy, n-propoxy, i-propoxy, n-butoxy, i-butoxy, sec-butoxy, cyclohexyloxy, and the like.

The term "aryl" refers to any carbon-based aromatic group including, but not limited to, benzene, naphthalene, and the like. The term "aromatic" also includes "heteroaryl group," which is defined as an aromatic group that has at least one heteroatom incorporated within the ring of the aromatic group. Examples of heteroatoms include, but are not limited to, nitrogen, oxygen, sulfur. The aryl group can be substituted with one or more groups including, but not limited to, alkyl, aryl, halogen, nitro, hydroxy, carboxylic acid, or alkoxy, or the aryl group can be unsubstituted.

The term "heteroaryl" is understood to mean saturated (heterocycloalkyl), partly unsaturated (heterocycloalkenyl) or unsaturated (heteroaryl) hydrocarbon rings containing from 3 to 15 carbon atoms in a mono- or bicyclic, fused, bridged or spirocyclic ring in which 1 to 5 carbon atoms of the 3 to 15 ring carbon atoms are replaced by heteroatoms such as nitrogen, oxygen or sulfur in which further the heteroatoms can be oxidized, for example N═O, S═O, $SO_2$.

Non-limiting examples of heterocycles are acridinyl, azaindole (1H-pyrrolopyridinyl), azabenzimidazolyl, azaspirodecanyl, azepinyl, azetidinyl, aziridinyl, benzimidazolyl, benzofuranyl, dihydrobenzofuranyl, benzothiofuranyl, benzothiophenyl, benzoxazolyl, benzthiazolyl, benztriazolyl, benztetrazolyl, benzisoxazolyl, benzisothiazolyl, carbazolyl, 4aH-carbazolyl, carbolinyl, chromanyl, chromenyl, cinnolinyl, decahydrochinolinyl, 4,5-dihydrooxazolinyl, dioxazolyl, dioxazinyl, 1,3-dioxolanyl, 1,3-dioxolenyl, 3,3-dioxo[1,3,4]oxathiazinyl, 6H-1,5,2-dithiazinyl, dihydrofuro[2,3-b]-tetrahydrofuranyl, furanyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl (benzimidazolyl), isothiazolyl, isothiazolidinyl, isothiazolinyl, isoxazolyl, isoxazolinyl, isoxazolidinyl, 2-isoxazolinyl, ketopiperazinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2-oxa-thiepanyl, 1,2-oxathiolanyl, 1,4-oxazepanyl, 1,4-oxazepinyl, 1,2-oxazinyl, 1,3-oxazinyl, 1,4-oxazinyl, oxazolidinyl, oxazolinyl, oxazolyl, oxetanyl, oxocanyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazolyl, pyridoimidazolyl, pyridothiazolyl, pyridinyl, pyridyl, pyrimidinyl, pyrrolidinyl, pyrrolidinonyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrahydrofuranyl, tetrahydropyranyl, tetrahydropyridinyl, tetrahydrothiophenyl, tetrazinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, 1,2-thiazinyl, 1,3-thiazinyl, 1,4-thiazinyl, 1,3-thiazolyl, thiazolyl, thiazolidinyl, thiazolinyl, thienyl, thietanyl, thienothiazolyl, thienooxazolyl, thienoimidazolyl, thiomorpholinyl, thiophenolyl, thiophenyl, thiopyranyl, 1,2,3-triazinyl, 1,2,4-triazinyl, 1,3,5-triazinyl, 1,2,3-triazolyl, 1,2,3-triazolyl, 1,2,4-triazolyl, 1,2,5-triazolyl, 1,3,4-triazolyl and xanthenyl.

The term "amine" refers to a group of the formula —NRR', where R and R' can be, independently, hydrogen or an alkyl, alkenyl, alkynyl, aryl, aralkyl, cycloalkyl, halogenated alkyl, or heterocycloalkyl group described above.

"Carbonyl" refers to a radical of the formula —C(O)—. Carbonyl-containing groups include any substituent containing a carbon-oxygen double bond (C═O), including acyl groups, amides, carboxy groups, esters, ureas, carbamates, carbonates and ketones and aldehydes, such as substituents based on —COR or —RCHO where R is an aliphatic, heteroaliphatic, alkyl, heteroalkyl, hydroxyl, or a secondary, tertiary, or quaternary amine, phenyl, a substituted phenyl (substituted with, for example, halogen, $C_1$-$C_3$ alkyl, alkoxy, amine), carboxyl, alkoxycarbonyl, amine, aryl. "Aminocarbonyl" alone or in combination, means an amino substituted carbonyl (carbamoyl) radical, wherein the amino radical may optionally be mono- or di-substituted, such as with alkyl, aryl, aralkyl, cycloalkyl, cycloalkylalkyl, alkanoyl, alkoxycarbonyl, aralkoxycarbonyl and the like. An aminocarbonyl group may be —N(R)—C(O)—R (wherein R is a substituted group or H) or —C(O)—N(R).

"Carboxyl" refers to a —COOH radical. Substituted carboxyl refers to —COOR where R is aliphatic, heteroaliphatic, alkyl, heteroalkyl, or a carboxylic acid or ester.

The term "hydroxyl" is represented by the formula —OH.

The term "hydroxyalkyl" refers to an alkyl group that has at least one hydrogen atom substituted with a hydroxyl group. The term "alkoxyalkyl group" is defined as an alkyl group that has at least one hydrogen atom substituted with an alkoxy group described above.

Optionally substituted groups, such as "optionally substituted alkyl," refers to groups, such as an alkyl group, that when substituted, have from 1-5 substituents, typically 1, 2 or 3 substituents, selected from alkoxy, optionally substituted alkoxy, acyl, acylamino, acyloxy, amino, aminoacyl, aminoacyloxy, aryl, carboxyalkyl, optionally substituted cycloalkyl, optionally substituted cycloalkenyl, halogen, optionally substituted heteroaryl, optionally substituted heterocyclyl, hydroxy, sulfonyl, thiol and thioalkoxy.

In particular, optionally substituted alkyl groups include, by way of example, haloalkyl groups, such as fluoroalkyl groups, including, without limitation, trifluoromethyl groups. These potential optional substituents apply to any group of the formula disclosed herein where an optional substituent is recited. Preferable optional substituents are hydroxyl, alkyl, alkoxy, carbonyl, alkoxycarbonyl, —$NO_2$, amine.

The term "carboxyester" is represented by the formula —C(O)—O—R. The term "carboxamide" is represented by the formula —C(O)—N(R)—R. The term "primary, secondary or tertiary amine" is represented by the formula —N(R)—R. The term "carbamate" is represented by the formula —NR—C(O)—O—R. The term "amide amine" is represented by the formula —NH—C(O)—NH—R. The term "sulfide" is represented by the formula —S—R. For the definitions above, preferably the terms R, R' are independently selected from the group of H, alkyl, alkylhalo, alkoxy, or amine, and wherein X is halogen. The terms R, R' also comprise the possibility of any given group being appended to R. The term "nitro" refers to an —$NO_2$ group.

Optionally substituted groups, such as "optionally substituted" refers to groups, such as an alkyl group, that when substituted, have from 1-5 substituents, typically 1, 2 or 3 substituents.

The term heteroaromatic group refers to a configuration comprising one or more heterocyclic optionally aromatic ring structures, for example comprising a heteroaromatic ring structure conjugated with aromatic ring structures, i.e. a ring comprising preferably C and one or more of N, O and/or S. A heteroaromatic group also comprises a 6-membered heterocycle, and relates preferably to a cycloalkyl, cycloalkane non-aromatic cyclic structures, such as cyclohexyl, or to aromatic cyclic structures, such as phenyl, and the like. A 6-membered aromatic heterocycle, comprising one or more of N, O and/or S is also comprised under an aromatic or heteroaromatic group, as described herein, and refers to a configuration comprising one or more 6-membered ring structures comprising C and one or more of N, O and/or S, preferably selected from a configuration if a hydrogen atom is removed from pyridine, pyridazine, pyrimidine, pyrazine, pyran, triazine, thiazine, thiopyran, oxazine, and the like.

Protected derivatives of the disclosed compound also are contemplated, for example for use in the synthesis of the disclosed compounds. A variety of suitable protecting groups for use with the disclosed compounds are disclosed in Greene and Wuts Protective Groups in Organic Synthesis; 3rd Ed.; John Wiley & Sons, New York, 1999. In general, protecting groups are removed under conditions which will not affect the remaining portion of the molecule. These methods are well known in the art and include acid hydrolysis, hydrogenolysis and the like.

Particular examples of the presently disclosed compounds include one or more asymmetric centers; thus these compounds can exist in different stereoisomeric forms. Accordingly, compounds and compositions may be provided as individual pure enantiomers or as stereoisomeric mixtures, including racemic mixtures.

The compounds of the invention may also exist in various polymorphous forms, for example as amorphous and crystalline polymorphous forms. All polymorphous forms of the compounds of the invention belong within the framework of the invention and are a further aspect of the invention.

The compound of the invention may also comprise deuterium replacing hydrogen. This replacement may in some circumstances lead to improved metabolic stability (Nature Reviews Drug Discovery 15, 219-221 (2016)).

It is understood that substituents and substitution patterns of the compounds described herein can be selected by one of ordinary skill in the art to provide compounds that are chemically stable and that can be readily synthesized by techniques known in the art and further by the methods set forth in this disclosure.

The present invention relates further to pharmaceutically acceptable salts of the compounds described herein. The term "pharmaceutically acceptable salt" refers to salts or esters of the compounds described herein prepared by conventional means that include basic salts of inorganic and organic acids. "Pharmaceutically acceptable salts" are also inclusive of the free acid, base, and zwitterionic forms. Descriptions of suitable pharmaceutically acceptable salts can be found in Handbook of Pharmaceutical Salts, Properties, Selection and Use, Wiley VCH (2002). For therapeutic use, salts of the compounds are those wherein the counter-ion is pharmaceutically acceptable. However, salts of acids and bases which are non-pharmaceutically acceptable may also find use, for example, in the preparation or purification of a pharmaceutically acceptable compound.

Compositions and Modes of Treatment:

Another aspect of the disclosure includes pharmaceutical compositions prepared for administration to a subject and which include a therapeutically effective amount of one or more of the compounds disclosed herein. The therapeutically effective amount of a disclosed compound will depend on the route of administration, the species of subject and the physical characteristics of the subject being treated. Specific factors that can be taken into account include disease severity and stage, weight, diet and concurrent medications. The relationship of these factors to determining a therapeutically effective amount of the disclosed compounds is understood by those of skill in the art.

Pharmaceutical compositions for administration to a subject can include at least one further pharmaceutically acceptable additive such as carriers, thickeners, diluents, buffers, preservatives, surface active agents and the like in addition to the molecule of choice. Pharmaceutical compositions can also include one or more additional active ingredients such as antimicrobial agents, anti-inflammatory agents, anesthetics, and the like. The pharmaceutically acceptable carriers useful for these formulations are conventional. Remington's Pharmaceutical Sciences, by E. W. Martin, Mack Publishing Co., Easton, Pa., 19th Edition (1995), describes compositions and formulations suitable for pharmaceutical delivery of the compounds herein disclosed.

In general, the nature of the carrier will depend on the particular mode of administration being employed. For instance, parenteral formulations usually contain injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

The pharmaceutical compositions can be administered to subjects by a variety of mucosal administration modes, including by oral, rectal, intraocular, intranasal, intrapulmonary, or transdermal delivery, or by topical delivery to other surfaces. Optionally, the compositions can be administered by non-mucosal routes, including by intramuscular, intraocular, subcutaneous, intravenous, intra-arterial, intra-articular, intraperitoneal, intrathecal, intracerebroventricular, or parenteral routes.

The compositions of the disclosure can alternatively contain as pharmaceutically acceptable carrier substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, and triethanolamine oleate. For solid compositions, conventional nontoxic pharmaceutically acceptable vehicles can be used which include, for example, pharmaceutical grades of mannitol, lactose, starch, magnesium stearate, sodium saccharin, talcum, cellulose, glucose, sucrose, magnesium carbonate, and the like.

In a preferred embodiment, the invention comprises the topical and/or local administration of a compound as described herein and/or a composition comprising a compound as described herein to a subject. The term "topical administration" refers to the delivery of a pharmacologically active agent to the skin or mucosa of a patient. Topical administration can provide a local rather than a systemic effect. The terms "topical administration" and "transdermal administration" are used interchangeably to mean administration of a pharmacologically active agent to the skin or mucosa of a patient to achieve a therapeutic effect in treating or preventing a medical disorder of the invention or discomfort at the site of topical or transdermal administration. Preferred administration modes relate to a topical solution, lotion, shake lotion, cream, ointment, gel, foam, transdermal patch, powder, solid form, sponge, tape, paste or tincture. Preferred embodiments relate to creams, foams, gels, lotions, and ointments.

Various additives, known to those skilled in the art, may be included in topical compositions of the present disclosure. For example, solvents, including relatively small amounts of alcohol, may be used to solubilize a compound of the invention. Other optional additives include antioxidants, fragrances, colorant, gelling agents, emulsifiers, thickening agents, stabilizers, surfactants, buffers, cooling agents (e.g., menthol) and the like. Other agents may also be added, such as antimicrobial agents, to prevent spoilage upon storage, i.e., to inhibit growth of microbes such as yeasts and molds. Examples of suitable antimicrobial agents include methyl and propyl esters of p-hydroxybenzoic acid (i.e., methyl and propyl paraben), sodium benzoate, sorbic acid, imidurea, and the like. When applied to skin, a topical composition of the present disclosure can be covered with an occlusive or non-occlusive dressing, which may be porous or non-porous, so as to protect the composition from mechanical removal during the period of treatment, e.g. a plastic film food wrap or other non-absorbent film. Various inert coverings may be employed. Non-woven or woven coverings may be employed, particularly elastomeric coverings, which allow for heat and vapor transport. These coverings can allow for cooling of the diseased site, which can provide for greater comfort, while protecting the composition from mechanical removal.

In accordance with the various treatment methods of the disclosure, the compound can be delivered to a subject in a manner consistent with conventional methodologies associated with management of the disorder for which treatment or prevention is sought. In accordance with the disclosure herein, a prophylactically or therapeutically effective amount of the compound and/or other biologically active agent is administered to a subject in need of such treatment for a time and under conditions sufficient to prevent, inhibit, and/or ameliorate a selected disease or condition or one or more symptom(s) thereof.

Further, the pharmaceutical composition may contain additionally components, e.g. compounds like one or more anti-inflammatory molecules, anti-angiogenic molecules, cytotoxic molecules, immunomodulatory molecules, preferably chemokines, cytokines, CD40 ligand, costimulatory molecules or antibodies or mixtures thereof.

"Administration of" and "administering a" compound should be understood to mean providing a compound, a prodrug of a compound, or a pharmaceutical composition as described herein. The compound or composition can be administered by another person to the subject (e.g., intravenously, gel, cream, spray) or it can be self-administered by the subject (e.g., tablets, gel, cream, spray).

Dosage can be varied by the attending clinician to maintain a desired concentration at a target site (for example, the lungs or systemic circulation). Higher or lower concentrations can be selected based on the mode of delivery, for example, trans-epidermal, rectal, oral, pulmonary, or intranasal delivery versus intravenous or subcutaneous delivery. Dosage can also be adjusted based on the release rate of the administered formulation, for example, of an intrapulmonary spray versus powder, sustained release oral versus injected particulate or transdermal delivery formulations, and so forth.

The compounds described herein having the desired therapeutic or adjuvant activity may be administered in a physiologically acceptable carrier to a patient, as described herein. Depending upon the manner of introduction, the compounds may be formulated in a variety of ways as discussed herein. The concentration of therapeutically active compound in the formulation may vary from about 0.1-100 wt %. The agents may be administered alone or in combination with other treatments.

The administration of the pharmaceutical composition can be done in a variety of ways as discussed above, including, but not limited to, orally, subcutaneously, intravenously, intra-arterial, intranodal, intramedullary, intrathecal, intraventricular, intranasally, conjunctival, intrabronchial, transdermally, intrarectally, intraperitoneally, intramuscularly, intrapulmonary, vaginally, rectally, or intraocularly.

The attending physician and clinical factors will determine the dosage regimen. A typical dose can be, for example, in the range of 0.001 to 1000 pg per kg body weight; however, doses below or above this exemplary range are envisioned, especially considering the aforementioned factors.

The term "subject" includes both human and veterinary subjects. The term "treatment" refers to a therapeutic intervention that ameliorates a sign or symptom of a disease or pathological condition after it has begun to develop.

As used herein, the term "treating" may include "ameliorating", with reference to a disease or pathological condition, and refers to any given beneficial effect of the treatment. The beneficial effect can be evidenced, for example, by a delayed onset of clinical symptoms of the disease in a subject, a reduction in severity of some or all clinical symptoms of the disease, a slower progression of the disease, an improvement in the overall health or well-being of the subject, or by other parameters well known in the art that are specific to the particular disease.

The present invention encompasses both therapeutic treatment and prophylactic treatment of a subject. A "prophylactic" treatment is a treatment administered to a subject, who does not exhibit signs of the medical condition or who preferably exhibits indications of developing or developing further any given medical condition, for the purpose of decreasing the risk of developing pathology or clinical symptoms. A prophylactic administration may comprise the administration of the compounds in advance of developing symptoms, thereby avoiding or reducing the subsequent occurrence of a disease. The present invention also relates to a method of treatment of subjects suffering from the various medical conditions disclosed herein. The method of treatment comprises preferably the administration of a therapeutically effective amount of a compound disclosed herein to a subject in need thereof.

A "therapeutically effective amount" refers to a quantity of a specified agent sufficient to achieve a desired effect in a subject being treated with that agent. For example, this may be the amount of a compound disclosed herein useful in alleviating the symptoms of one or more of the medical conditions described herein in a subject. The therapeutically effective amount or diagnostically effective amount of an agent will be dependent on the subject being treated, the severity of illness, and the manner of administration of the therapeutic composition. Dosage regimens can be adjusted to provide an optimum prophylactic or therapeutic response. A therapeutically effective amount is also one in which any toxic or detrimental side effects of the compound and/or other biologically active agent is outweighed in clinical terms by therapeutically beneficial effects. A non-limiting range for a therapeutically effective amount of a compound and/or other biologically active agent within the methods and formulations of the disclosure is about 0.001 mg/kg body weight to 50 mg/kg body weight, 0.01 mg/kg body weight to about 20 mg/kg body weight, such as about 0.05 mg/kg to about 5 mg/kg body weight, or about 0.2 mg/kg to about 2 mg/kg body weight.

The instant disclosure also includes kits, packages and multi-container units containing the herein described pharmaceutical compositions, active ingredients, and/or means for administering the same for use in the prevention and treatment of diseases and other conditions in mammalian subjects.

FIGURES

The invention is further described by the following figures. These are not intended to limit the scope of the invention but represent preferred embodiments of aspects of the invention provided for greater illustration.

BRIEF DESCRIPTION OF THE FIGURES

FIG. 1: Potent activators of iNKTs.

FIG. 2: Analysis of unspecific proliferative responses of murine cells stimulated without or with enhanced concentrations of the (B/C/E/F) Phytosphingosine-compounds or (A/D) controls shown by thymidine uptake (count per minute, cpm) and Stimulation index (SI).

FIG. 4: Effect after treatment with IPB 0964-1917—Cell proliferation tracked by CFSE loss in A/B) CD4+ and C/D) CD8+ T cells after interaction with matured Antigen Presenting Cells (APC).

FIG. 5: Immunization protocol—Administration (intramuscular route) of Ovalbumin with adjuvants.

FIG. 6: Development of the weight of mice vaccinated with Ovalbumin-containing control formulations and ovalbumin combined with adjuvants via the intramuscular route.

FIG. 8: Antigen-specific multifunctional CD4+ T cells.

FIG. 9: Immunization protocol—Administration (intranasal route) of Ovalbumin with adjuvants.

FIG. 10: Development of the weight of mice vaccinated with Ovalbumin-containing control formulations and ovalbumin combined with adjuvants via the intranasal route.

DETAILED DESCRIPTION OF THE FIGURES

FIG. 1: Potent activators of iNKTs. Presented is a selection of prior art compounds including KRN7000 and α-GalCer derivatives.

FIG. 2: Analysis of unspecific proliferative responses of murine cells stimulated without or with enhanced concentrations of the Phytosphingosine-compounds. Splenocytes from mice were re-stimulated for 96 h with different concentrations of adjuvant (1, 10 and 20 μg/ml). The results are presented by are expressed (A-C) as counts per minute (cpm) and (D-F) stimulation index (SI) being the ratio of [$^3$H]-thymidine uptake of stimulated versus non-stimulated samples. (A) and (D) show data for α-GalCer controls, (B) and (E) show data for IPB1901-1910, and (C) and (F) show data for IPB1911-1917.

Figure 3A:
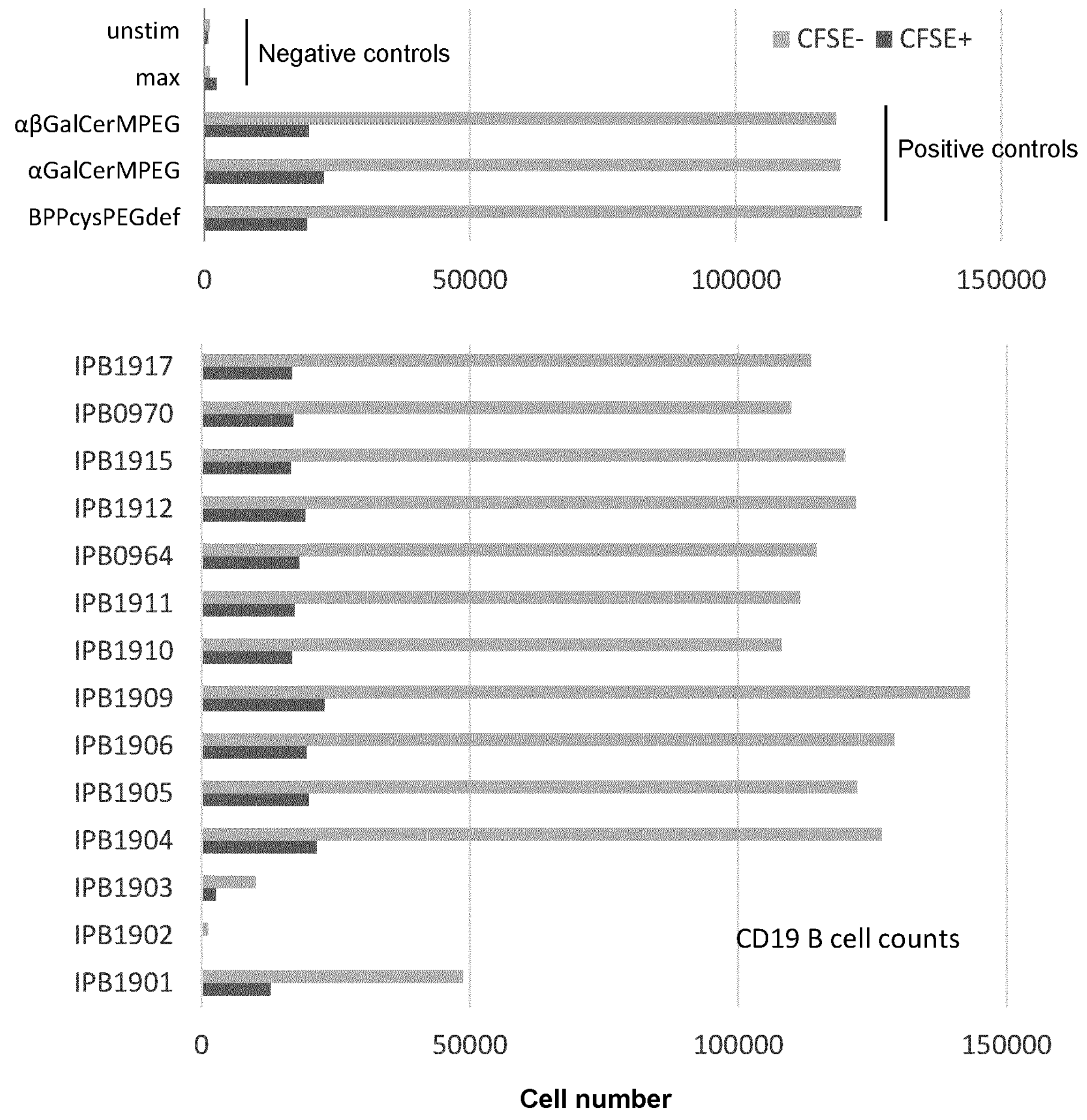
FIG. 3A: Cell proliferation tracked by CFSE dilution of CD19+ B cells after interaction with matured Antigen Presenting Cells (APC).

FIG. 3A: Cell proliferation tracked by CFSE dilution of B cells after interaction with matured Antigen Presenting Cells (APC). With every cell division, the CFSE signal strength is approximately halved. The observed cell numbers indicate the ratio of proliferating viable CD19+ B cells.

Figure 3B:
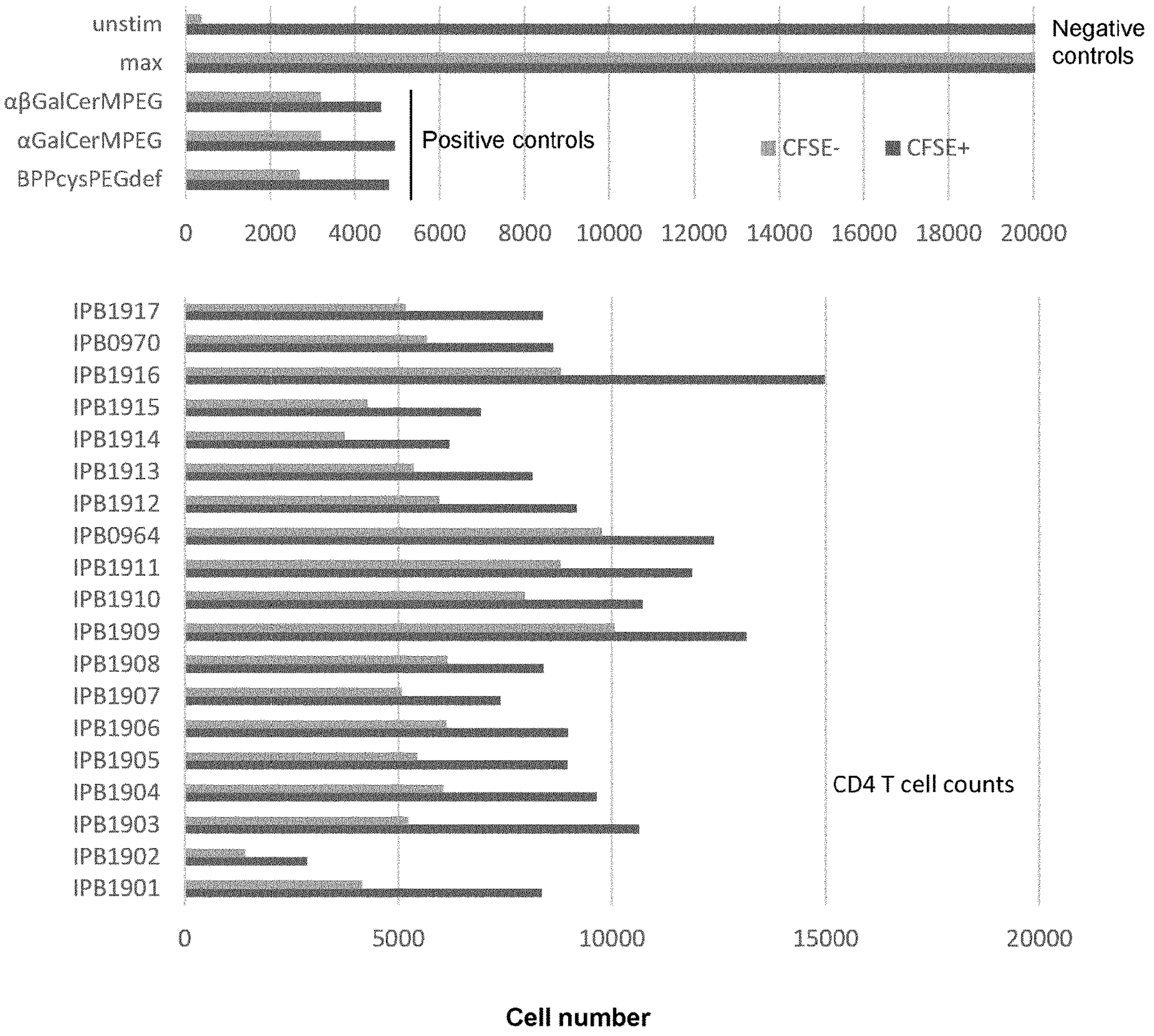
FIG. 3B: Cell proliferation tracked by CFSE dilution of CD4+ T cells after interaction with matured Antigen Presenting Cells (APC).

FIG. 3B: Cell proliferation tracked by CFSE dilution of CD4+ T cells after interaction with matured Antigen Presenting Cells (APC). With every cell division, the CFSE signal strength is approximately halved. The shown cell numbers indicate the ratio of proliferated live CD4+ T cells.

Figure 3C:
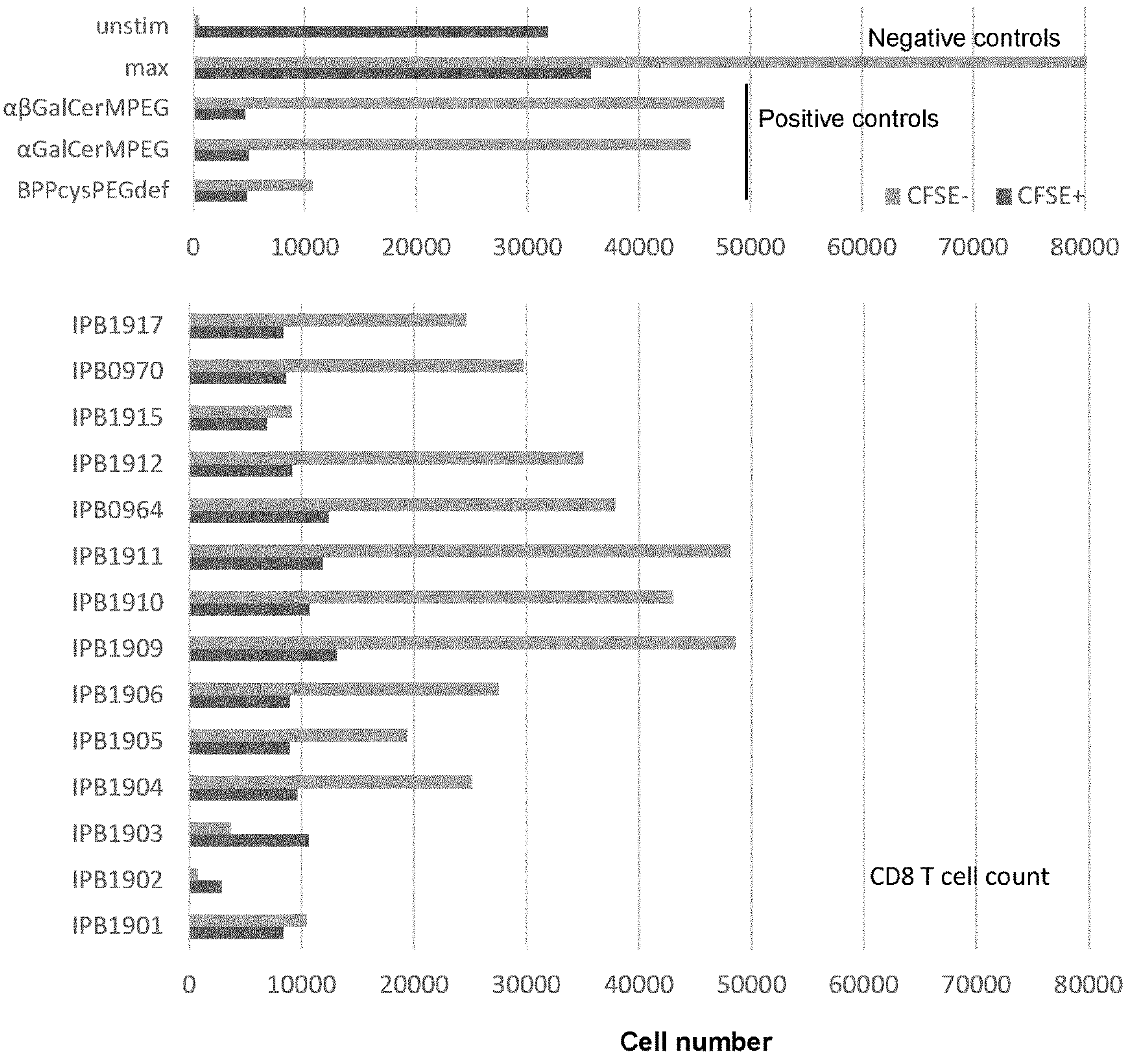
FIG. 3C: Cell proliferation tracked by CFSE dilution of CD8+ T cells after interaction with matured Antigen Presenting Cells (APC).

FIG. 3C: Cell proliferation tracked by CFSE dilution of CD8+ T cells after interaction with matured Antigen Presenting Cells (APC). With every cell division, the CFSE signal strength is approximately halved. The shown cell numbers indicate the ratio of proliferated live CD8+ T cells FIG. 4: Effect after treatment with IPB 0964-1917—Cell proliferation tracked by CFSE loss of T cells after interaction with matured Antigen Presenting Cells (APC). With every cell division, the CFSE signal strength is reduced. The shown cell numbers indicate the ratio of proliferating T and B cells (7 steps are shown). (A) Numbers of CD4+ T cells are shown at different proliferation steps up to 7 days measuring the loss of CFSE. Naïve cells were treated with one of IPB1901-1912 together with DCs activated with Ova prior to the CFSE assay. (B) Numbers of CD4+ T cells are shown at different proliferation steps up to 7 days measuring the loss of CFSE. Naïve cells were treated with one of IPB2033-2044 together with DCs activated with Ova prior to the CFSE assay. (C) Numbers of CD8+ T cells are shown at different proliferation steps up to 7 days measuring the loss of CFSE. Naïve cells were treated with one of IPB1901-1912 together with DCs activated with Ova prior to the CFSE assay. (D) Numbers of CD8+ T cells are shown at different proliferation steps up to 7 days measuring the loss of CFSE. Naïve cells were treated with one of IPB2033-2044 together with DCs activated with Ova prior to the CFSE assay.

FIG. 5: Immunization protocol—Administration (intramuscular route) of Ovalbumin with adjuvants. Ovalbumin (30 μg) was co-administered (intramuscular) without or with different adjuvants, such as IPB 2033-2044, c-di-AMP or aßGalCerMPEG (15 μg), on days 0, 14 and 28.

FIG. 6: Development of the weight of mice vaccinated with Ovalbumin-containing control formulations and ovalbumin combined with adjuvants via the intramuscular route. (A) Mice weight after administration of controls ovalbumin, owa+c-di-AMP or ova+alpha-beta-GalCerMPEG. Animal body weight was monitored throughout the whole experimental setting. (B) Development of the weight of mice vaccinated with different Ovalbumin-containing IPB 2033-2044 formulations. Animal body weight was monitored throughout the whole experimental setting. No signs of acute toxicity were observed in animals receiving Ovalbumin-containing IPB 2033-2044 formulations by i.m. route.

Figure 7:
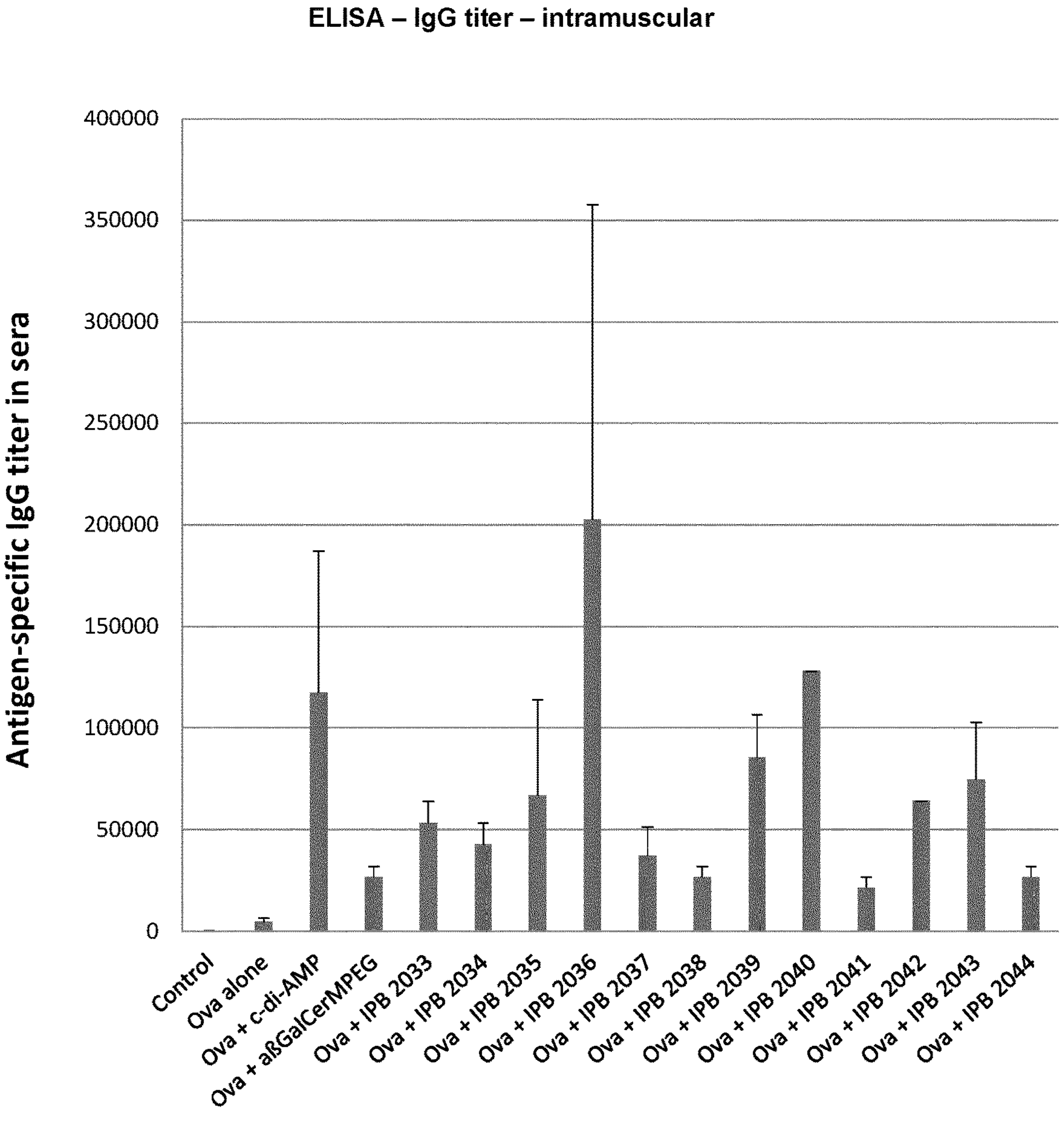
FIG. 7: Systemic humoral immune responses induced in mice.

FIG. 7: Systemic humoral immune responses induced in mice. Shown is the IgG titer as a readout of systemic humoral immune responses induced in mice after three immunizations with Ovalbumin co-administered with different adjuvants via intramuscular route. Ova-specific IgG titers were measured via ELISA in sera 14 days after the last immunization.

FIG. 8: Antigen-specific multifunctional CD4+ T cells. (A) Groups of 3 BALB/c mice were immunized intramuscularly with PBS (control) or with three doses (14 days apart) of Ovalbumin (30 μg), alone or adjuvanted with c-di-AMP or aßGalCerMPEG or IPB 2033-2044 (15 μg). At 14 days after the second immunization, spleen cells were harvested, restimulated with Ovalbumin, intracellularly stained for double positive Th cytokines (IFN-γ, IL-2, TNF-α, IL-4 and IL-17), and analyzed by flow cytometry. (B) Groups of 3 BALB/c mice were immunized intramuscularly with PBS (control) or with three doses (14 days apart) of Ovalbumin (30 μg), alone or adjuvanted with c-di-AMP or aßGalCerMPEG or IPB 2033-2044 (15 μg). At 14 days after the second immunization, spleen cells were harvested, restimulated with Ovalbumin, intracellularly stained for triple positive Th cytokines (IFN-γ, IL-2, TNF-α, IL-4 and IL-17), and analyzed by flow cytometry.

FIG. 9: Immunization protocol—Administration (intranasal route) of Ovalbumin with adjuvants. Immunization protocol: Mucosal administration (intranasal (i.n.) route) of Ovalbumin (30 μg) co-administered without or with different adjuvants, such as IPB 2033-2044, c-di-AMP or aßGalCerMPEG (15 μg), on days 0, 14 and 28.

FIG. 10: Development of the weight of mice vaccinated with Ovalbumin-containing control formulations and ovalbumin combined with adjuvants via the intranasal route. (A) Development of the weight of mice vaccinated with different Ovalbumin-containing control formulations by i.n. route. Animal body weight was monitored throughout the whole experimental setting. (B) Development of the weight of mice vaccinated with different Ovalbumin-containing IPB 2033-2044 formulations by i.n. route. Animal body weight was monitored throughout the whole experimental setting. No signs of acute toxicity were observed in animals receiving Ovalbumin-containing IPB 2033-2044 formulations.

Figure 11:
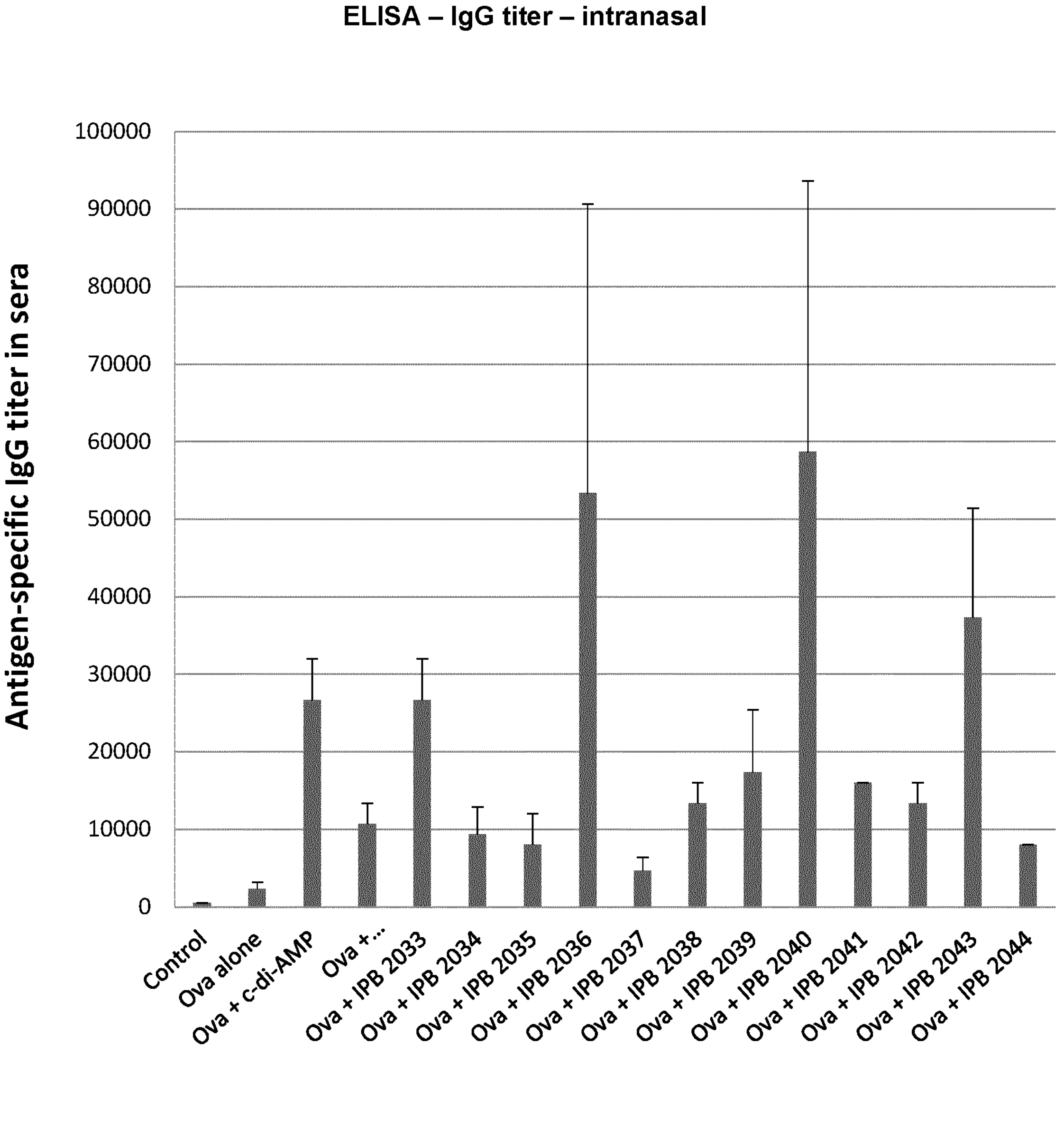
FIG. 11: Systemic humoral immune responses induced in mice.

FIG. 11: Systemic humoral immune responses induced in mice. Shown is the IgG titer as a readout of systemic humoral immune responses induced in mice after three immunizations with Ovalbumin co-administered with different adjuvants via intranasal route. Ova-specific IgG titers in sera 14 days after the last immunization.

EXAMPLES

The invention is further described by the following examples. These are not intended to limit the scope of the invention but represent preferred embodiments of aspects of the invention provided for greater illustration.

Example 1: Unspecific T and B Cell Stimulation

In order to assess the properties of the inventive compounds in antigen-unspecific immune response stimulation the compounds were administered to splenocytes in an established proliferation assay.

For the proliferation assay, splenocytes ($5\times10^6$ cells/ml) are seeded at 100 μl per well in a U-bottomed 96-well microtiter plate (Sarstedt Inc., Newton, N.C.) and cultured in quadruplicates 4 days in the presence of enhanced concentrations of adjuvant (1, 10 and 20 μg/ml)), 5 μg/ml of Concanavalin A (max); or medium alone. Eighteen hours before harvesting, 1 μCi of [3H]thymidine (Amersham International, Freiburg, Germany) is added to each well. Cells are harvested on paper filters (Filtermat A; Wallac, Freiburg, Germany) using a cell harvester (Inotech, Wohlen, Switzerland) and the incorporation of [3H] thymidine into the DNA of proliferating cells is determined using a scintillation counter (Wallac 1450, Micro-Trilux).

The novel phytosphingosine derivatives, IPB 1901 (SI 4), IPB 1902 (SI>3), IPB 1903 (SI>10), IPB 1904 (SI>3), IPB 1910 (SI ca. 2) in FIG. 2E and IPB 1911, IPB 1913 (SI>1.5), IPB 1912 (SI>2.5), amongst others in FIG. 2F, showed induction of unspecific proliferation after restimulation of splenocytes with different concentrations of the Phytosphingosine-compounds (1, 10 and 20 μg/ml) for 96 h. Refer to FIG. 2.

Example 2: Antigen-Specific T and B Cell Stimulation by Maturated Bone Marrow Derived DCs In order to assess the properties of the inventive compounds in antigen-specific T and B cell stimulation, the compounds were administered to cultured bone marrow cells in a CFSE assay.

Briefly, femurs and Tibiae of female 4-12 weeks old C57Bl6 (or BALB/c for TCR HA) were removed and purified from the surrounding muscle tissue (Kleenex tissues). Intact Bones were left in 70% ethanol for 2-5 min for disinfection. Both ends were cut with scissors and the bone marrow were flushed with PBS using a syringe with a 0.45 mm diameter needle, clusters were disintegrated by vigorous pipetting.

In order to obtain activated antigen presenting dendritic cells (DCs), bone marrow cells were cultured with GM-CSF. On Day 0, cells were seeded in a concentration of $2\times10^6$ cells per 100 mm dish (bacteriological petri dishes) in 10 ml RPMI-10 (100 U Pen/100 μg Strept/2 mM Glutamin/50 μm ß-Mercaptoethanol/10% FCS heat-inactivated and filtered 0.22 μm Filter) containing 200 Units GM-CSF. On Day 3 another 10 ml RPMI-10 containing 200 U GM-CSF were added to the plates. On Day 6 half of the culture supernatants (10 ml) were collected, centrifuged and the cell pellet resuspended in 10 ml fresh RPMI-10/200 U GM-CSF and given back into the original plates.

Subsequently, the DCs were incubated with Ovalbumin (as antigen) alone or co-administered with known adjuvants, such as α-GalCerMPEG, aßGalCerMPEG or TLR2/6 ligand (BPPcysMPEG), or the novel phytosphingosine derivatives of the present invention. The activation of DCs was controlled by FACS analysis of different CD markers, such as CD40, CD54, CD80, CD86, CD83, MHCI and MHCII.

The effect of the compounds of the present invention was then ascertained via co-incubation of naïve T or B cells, obtained from mice (OTI or OTII mice) with previous exposure to the Ova antigen, with DCs that had been treated with the compounds of the invention.

Naïve T cells were derived from LN/spleen from OTI or OTII mice. The MagniSort™ Mouse CD4 naïve or CD8 naïve T cell Enrichment Kit is designed for the magnetic separation of CD4 or CD8 naïve T cells by negative selection from mouse spleens or lymph nodes utilizing a biotinylated antibody cocktail and streptavidin-coated magnetic beads. Undesired cells are bound by antibody (Anti-Mouse CD8 or CD4/CD11b CD19/CD24/CD44/CD45R(B220)/CD49b(Integrin α 2)/Ly-6G (Gr-1)/γδ TCR/TER-119) and then magnetic beads that, when placed in a magnetic field, leave CD4 or CD8 naïve T cells untouched and free in solution.

CFSE staining of the CD4+ or CD8+ naïve T cells is then carried out according to standard procedures. Subsequently, $2\text{-}5\times10^4$ DCs (as mature antigen presenting cells APCs) are incubated with $4\times10^5$ CFSE+ T cells (OTI or OTII) per well (ratio DC/T cells is 1:4 or 1:8). A CFSE proliferation assay is then conducted, using on Day +5 or on Day +7 a FACS analysis (CFSE/LD/CD4/CD8/CD19/Thy1.1), providing a cell count for the desired cell type based on CFSE. With every cell division, the CFSE signal strength is approximately halved. The cells marked with CFSE can therefore be used to determine the proliferation of CD19+ B cells, CD4+ or CD8+ T cells in response to treatment with activated DCs, that were treated with or without the compounds of the invention.

Example 3A: Antigen-Specific CD19+ B Cell Proliferation

As is shown in FIG. 3A, cell proliferation of B cells is tracked by CFSE dilution after interaction with APCs. With every cell division, the CFSE signal strength is approximately halved. Therefore, the compounds of the invention show an effect on inducing antigen specific CD19+ cell proliferation.

On day −1, mature DCs were restimulated with Ovalbumin (antigen) co-administered with 10 μg of the different novel phytosphingosine derivatives (0964-1917) or with positive controls (α-GalCerMPEG, aßGalCerMPEG, CDA or BPPcysPEGdef) for 24 h. The novel phytosphingosine derivatives showed comparable or higher capacity to stimulate B cells via DC interaction.

The novel phytosphingosine derivatives, IPB 1909, IPB 1905, IPB 1906, IPB 1904 and IPB 1912 in FIG. 3A showed a particularly high capacity to induce antigen specific CD19+ B cell proliferation after interaction with matured Antigen Presenting Cells (APC) for 5 days. These compounds showed a greater effect than known adjuvants as controls. Additionally, essentially all compounds showed comparable effects to the adjuvant controls, with the exception of IPB 1916, IPB 1901, IPB 1902, IPB 1903, which may show some toxicity against B cells.

Example 3B: Antigen-Specific CD4+ T Cell Proliferation

As is shown in FIG. 3B, cell proliferation is of CD4+ T cells tracked by CFSE dilution after interaction with matured Antigen Presenting Cells (APC).

On day −1, mature DCs were restimulated with Ovalbumin (antigen) co-administered with 10 μg of the different novel phytosphingosine derivatives (IPB 0964-1917) or with positive controls (α-GalCerMPEG, aßGalCerMPEG, CDA or BPPcysPEGdef) for 24 h. The novel Phytosphingosine-compounds showed higher capacity to stimulate CD4+ T cells via DC interaction.

The novel phytosphingosine derivatives IPB 1909, IPB 0964, IPB 1903, IPB 1911 and IPB 1910 in FIG. 3B showed high capacity to induce antigen specific CD4+ T cell proliferation after interaction with matured Antigen Presenting Cells (APC) for 5 days. These compounds showed the greatest effect, although essentially all compounds showed improved effects over the adjuvant controls, with the exception of IPB 1902, which may show some toxicity against CD4+ T cells.

Example 3C: Antigen-Specific CD8+ T Cell Proliferation

As is shown in FIG. 3C, cell proliferation of CD8+ T cells is tracked by CFSE dilution after interaction with matured Antigen Presenting Cells (APC).

On day −1, mature DCs were restimulated with Ovalbumin (antigen) co-administered with 10 μg of the different novel phytosphingosine derivatives (IPB 1901-0964) or with positive controls (α-GalCerMPEG, aßGalCerMPEG, CDA or BPPcysPEGdef) for 24 h. The novel phytosphingosine derivatives showed comparable or higher capacity to stimulate CD8+ T cells via DC interaction. A strong capacity was seen to stimulate more efficiently antigen specific CD8+ T cells in comparison to the positive controls.

The novel phytosphingosine derivatives IPB 1909, IPB 0964, IPB 1911, IPB 1912 and IPB 1910 in FIG. 3C also showed a strong effect to induce antigen specific CD8+ T cell proliferation after interaction with matured Antigen Presenting Cells (APC) for 5 days.

Example 4: Cell Proliferation of CD4+ and CD8+ T Cells

As is shown in FIG. 4, cell proliferation of T and B cells is tracked by CFSE loss after interaction with matured Antigen Presenting Cells (APC). On day −1, mature DCs were restimulated with Ovalbumin (antigen) and co-administered with 10 μg of the different novel phytosphingosine derivatives (IPB 1901-0964 and IPB 2033-2044) for 24 h.

The novel phytosphingosine derivatives showed comparable or higher capacity to stimulate CD4+ T cells and 8+ T cells via DC interaction.

In FIG. 4A the novel phytosphingosine derivatives IPB 1901, IPB 1902, IPB 1903 and IPB 1912 showed a stimulating effect of CD4+ T cells beyond controls in which only the antigen Ova was used to activate the antigen presenting DCs. In FIG. 4B the novel phytosphingosine derivatives IPB 2036, IPB 2038, IPB 2039 showed a stimulating effect of CD4+ T cells beyond controls in which only the antigen Ova was used to activate the antigen presenting DCs.

In FIG. 4C the novel phytosphingosine derivatives IPB 1901, IPB 1902, IPB 1903 and IPB 1912 showed a stimulating effect of CD8+ T cells beyond controls in which only the antigen Ova was used to activate the antigen presenting DCs. In FIG. 4D the novel phytosphingosine derivatives IPB 2036, IPB 2039 showed a stimulating effect of CD8+ T cells beyond controls in which only the antigen Ova was used to activate the antigen presenting DCs.

The inventive compounds therefore showed high capacity to induce antigen-specific B or T cell proliferation after interaction with matured Antigen Presenting Cells (APC) for 7 days.

Further Examples

Additional experimentation was undertaken and is ongoing to investigate the properties of the compounds of the present invention with respect to their immune-stimulating action and potential as adjuvants. In particular, the compounds IPB 2033-2044 have been subjected to further analysis.

Many adjuvants from preclinical studies interact with receptors of the innate immune system, e.g. toll-like receptors (TLR) on antigen-presenting immune cells, thereby triggering an activation cascade. In contrast, the novel IPB compounds 2033-2044 interact with the surface molecule CD1d on antigen-presenting cells (e.g. dendritic cells). The contact of IPB 2033-2044 with CD1d mediates the bond between natural killer cells (NK cells) or iNKT cells and antigen-presenting cells, thus enhancing adjuvant activity.

The following experimental protocols are of relevance:

IPB 2033-2044 Adoptive Transfer Experiment (In Vitro):

Adoptive Transfer Models OTI and OTII:

OTII mice transgenic for aßTCR specific for 323-339 OVA-peptide in the context of H-2 I-Ab, and OTI mice transgenic for aßTCR specific for SIINFEKL OVA-peptide in the context of H-2Kb were crossed to Thy1.1 C57BL/6J congenic mice. For adoptive transfer, CD4 T cells from LN and spleen of OTII mice were purified using Affymetrix enrichment kit for naïve CD4+ T cells; CD8 T cells from LN and spleen of OTI mice were purified using Affymetrix enrichment kit for naïve CD8+ T cells. In all experiments, OTI or OTII cells were stained with CFSE (Cambridge Bioscience) before injection into Thy1.2+ recipient mice.

Where indicated, small naïve Thy1.1+CD4+CD62L+ CD44− OT-II cells were sorted by flow cytometry (MoFlo, DakoCytomation, UK). To ensure high purity, and the exclusion of memory (CD4+CD62L-CD44+) cells from the naïve CD4+CD62L+CD44-OT-II cell population, samples were sorted. Sorted cell purity was assessed on a MoFlo or based on a BD FACSsort. Before transfer Thy1.1+OT-II T cells were labeled with CFSE (Cambridge Bioscience, Cambridge, UK), as follows:

Prepare suspension of cells in PBS at about 0.5-3×$10^7$/ml

Add equal volume of 2 μM CFDA in PBS (stock 10 mM in DMSO) (=>1:5000; 5 ml PBS+1 μl CFDA stock)

Incubate the cells for 5 minutes at RT in the dark.

Add equal volume of FCS (bind to unbound CFSE)

Incubate the cells for further 5 minutes.

Centrifuge the cells and wash with complete medium one time.

Suspend the cells in medium 1 to 3×$10^6$ cells per congenic Thy1.2+ recipient mouse were injected i.v., unless otherwise stated. Mice were immunized the following day.

Where indicated, small naïve Thy1.1+CD8+CD62L+ CD44− OT-1 cells were sorted by flow cytometry (MoFlo, DakoCytomation, UK). To ensure high purity, and the exclusion of memory (CD8+CD62L-CD44+) cells from the naïve CD8+CD62L+CD44− OT-1 cell population, samples were sorted. Sorted cell purity was assessed on a MoFlo or based on a BD FACSsort. Before transfer Thy1.1+OT-1 T cells were labeled with CFSE (Cambridge Bioscience, Cambridge, UK) and were injected iv. at 1 to 3×$10^6$ cells per congenic Thy1.2+ recipient mouse, unless otherwise stated. Mice were immunized the following day.

The chimeras were immunized by different routes (e.g. i.n. or i.m.) with different volumes and concentrations (Table below). As antigen, endotoxin-free OVA protein (Hyglos) was used, formulated or conjugated to nanoparticles, and co-administered with different adjuvants (e.g. IPB 2033-2044, c-di-AMP, etc.).

TABLE

Routes of immunization

| Route | Volume | Ova Concentration |
|---|---|---|
| i.n. | 20 μl | 20 μg |
| Oral | 100 μl | 75 μg |
| Rectal | 50 μl | 75 μg |
| i.p. | 100 μl | 75 μg |
| Pulmonal | 75 μl | 20 μg |
| i.v. | 100 μl | 1 to 3 × $10^6$ cells |
| s.c. | 50-100 μl | 20 μg |

Flow Cytometry Analysis and FACS Cell Sort (CFSE) was carried out as follows:

Draining LNs and spleen were removed single-cell suspensions were prepared in RPMI medium containing 5% FCS.

The antibodies used for surface staining are listed in Table 2.

Thy1.1+ cells were analysed for the CFSE loss of LN or spleen cell suspensions by flow cytometry using a FACS Fortessa (Becton Dickinson).

Final analysis and graphical output were performed using FlowJo software (Treestar).

The number of Thy1.1 positive cells in combination with the loss of CFSE staining per sample (LN, spleen, etc.) and the numbers of proliferating CFSE-cells in response to the vaccine versus non-proliferating CFSE+ cells was calculated.

TABLE

Antibody list

| | Flourochrom | Marker | Action |
|---|---|---|---|
| 1 | FITC | CFSE | Proliferation |
| 2 | UV | Live/dead | |
| 3 | PE | CD3+ | T cells |
| 4 | APC | CD4+ | CD4+ T cells |
| 5 | APC-Cy7 | CD8+ | CD8+ T cells |

TABLE-continued

| Antibody list | | | |
|---|---|---|---|
| | Flourochrom | Marker | Action |
| (6) | PE-Cy7 | Thy1.1+ (CD90)− | Sorting |
| (7) | PE | CD69+/or CD19+ | Activation |

Immunization Protocol (In Vivo)

Groups of mice (3-5 animals) were immunized either intranasal (i.n.) or intramuscular (i.m.) on days 0, 14 and 281 with PBS, or with Ovalbumin (30 μg); the latter were administered alone or with different adjuvants—c-di-AMP, aßGalCerMPEG or IPB 2033 to 2044—made up to a maximal volume of 20 μl (i.n.) or 50 μl (i.m.) in PBS. Vaccinated animals showed no adverse effects when vaccinated with Ova in combinations of IPB 2033-2044.

Blood samples were collected on days 1, 14, 28 and 42 via retro-bulbar bleeding. Spleens of vaccinated mice were aseptically removed. For the subsequent methods, cell suspensions of spleens (n=5) of each immunized groups were prepared and erythrocytes were lysed. These splenocyte pools of each group were cultured in the presence of different concentrations of Ovalbumin; controls received 5 μg/mL concanavalin A. The incorporation of [$^3$H] thymidine into the DNA of proliferating cells was determined using a scintillation counter (Wallac 1450, Micro-Trilux).

Immunization Using IPB 2033-2044 Effectively Stimulates T-Cell-Mediated Proliferation Responses when Co-Administered with a Soluble Model Antigen (Proliferation)

The spleens were removed from sacrificed animals and combined for the analysis of the cell immune reactions. The cells were then resolved in RPMI 1640, supplemented by 10% fetal calf serum, 10 U/ml penicillin, 50 μg/ml streptomycin, $5\times10^5$ M ß-mercaptoethanol and 1 mM L-glutamine (GIBCO BRL, Karlsruhe, Germany) and stored at 37° C. in a humid atmosphere with 5% $CO_2$. The spleen cell suspensions were adjusted to $5\times10^6$ cells/ml in the complete medium, placed in a flat-bottomed microtiter plate with 96 wells (Nunc) at 100 μl/well, and the plates were incubated for four days in the presence of different concentrations of soluble IPB 2033-2044. Each concentration was tested in groups of three. During the last 18 hours of incubation, 1 μCi of $^3$H thymidine (Amersham International, Freiburg, Germany) was added to each well. The cells were then harvested on filter paper (Filtermat A; Wallac, Freiburg, Germany) using a cell harvester (Inotech, Wohlen, Switzerland) and the amount of $^3$H thymidine embedded in the DNA of the multiplied cells was determined using a γ-scintillation counter (Wallac 1450, Trilux). The results were presented as the arithmetic mean of the $^3$H thymidine uptake in cpm.

Detection of Antigen-Specific IgG and IgA in Serum (Humoral Response)

The Ova-specific antibodies were determined in serum samples by ELISA. Endpoint titers were expressed as reciprocal values of the last dilution, which gave an optical density at 405 nm of two times above the values of the negative controls. For calculation purposes, negative samples were assigned an arbitrary titer of the lowest dilution measured.

Immunization Using IPB 2033-2044 Effectively Stimulates Cytokines Secretion when Co-Administered with a Soluble Model Antigen (Elispot)

The number of Ova-specific cytokine-producing cells was determined using an ELISpot assay. 96-well plates (BD Pharmingen) were coated with anti-IFN-γ, anti-IL2, anti-IL4, anti-IL-10 or anti-IL17 antibodies overnight at 4° C. Then plates were washed one time with culture medium (RPMI, 10% fetal calf serum (FCS), PenStrep, L-glutamine, and ß-mercaptoethanol) and cells were seeded in culture medium with or without Ova (5 μg/ml). Plates were incubated 24 h for IFN-γ and 48 h for the other cytokines. Then, cells were removed and the plates processed according to manufacturer's instructions. Colored spots were counted with an ELISpot reader (CTL-Europe GmbH) and analyzed using the ImmunoSpot image analyzer software v3.2.

CDA-Adjuvanted Dose Elicits Multiple-Cytokine Producers Among Antigen-Specific T Cells (Multifunctional T Cells)

In order to characterize more accurately the cellular immune response, the production of intracellular cytokines was measured in CD4+ and CD8+ T cells. Multifunctional CD4+ and CD8+ cells were stimulated when mice received OVA+IPB 2033-2044. Vaccinated animals showed enhanced secretions of double or triple positive cytokines. The above-mentioned in vitro approach is very useful as an initial screening for the evaluation of cytokine profiles promoted by candidate adjuvants after stimulation of different types of cells. However, it does not allow accurate prediction of important effector functions of an adjuvant, such as CTL stimulation capabilities, target cell subpopulations and capacity to confer protective immunity.

Therefore, mice were immunized to assess the in vivo performance of CDA in an active vaccination setting. To assess vaccination effectivity, the frequencies of cytokine producers among the CD4+ and CD8+ T cell populations were evaluated by intracellular cytokine staining and flow cytometry. The production of multiple cytokines (especially IL-2, IFN-γ, IL-17, IL-10 and TNF-α) by T cells has been described to correlate with vaccine protective efficacy (Darrah, P. A., et. al., 2007, Nat Med 13 (7):843-50. doi: 10.1038/nm1592). Thus, the frequency of T cells producing single cytokines or combinations (positive events/million) was analyzed by flow cytometry. In contrast, the use of CDA and by IPB 2033-2044 adjuvanted Ovalbumin increased the frequency of triple, double and single cytokine producers.

NK Cells Combined with IPB 2033-2044 (FACS)

PBMCs were thawed and 1×106 to 4×106 cells/sample were re-stimulated for 16 h in complete RPMI 1640 (Gibco, supplemented with 10% FCS, 5% Penicillin/Streptomycin and 5% Glutamine) containing the vaccine formulation with a final concentration of 5 μg Ovalbumin/mL model antigen combined with IPB 2033-2044. Unstimulated samples were incubated for the same time in complete RPMI without the vaccine formulation. Brefeldin A and monensin were added to all samples after 5 h of incubation. Cells were collected and stained for flow cytometric analysis. Surface marker staining was performed for 20 min at 4° C. The following antibodies were used diluted in PBS: CD56 (PE-Cy7, clone B159, BD, Franklin Lakes, NJ, USA), CD3 (V450, clone UCHT1, BD), CD14 (Pacific Blue, clone M5E2, BD), CD19 (V450, clone HIB19, BD Horizon), CD16 (APC-H7, clone 3G8, BD Pharmingen), NKG2C (PE, clone 134591, R&D Systems, Minneapolis, MN, USA), CD57 (APC, clone HCD57, BioLegend, San Diego, CA, USA), Live/Dead (Fixable Blue, Invitrogen, Carlsbad, CA, USA). The expression of CD107a was used as a correlate of degranulation. To this end, the anti-CD107a antibody (PE-Cy5, clone eBioH4A3, eBioscience, San Diego, CA, USA) was added to the culture. The secretion of IFNγ (Alexa Fluor 700, clone B27, BioLegend) was detected by intracellular staining using Cytofix/Cytoperm solution (BD Biosciences). Samples were acquired at a BD Fortessa flow cytometer and analyzed using FlowJo (FlowJo, LLC, Ashland, OR, USA). Unstained, single stained (one antibody/sample) as well as fluorescence-minus-one (FMO) samples were used as controls for the acquisition as well as the subsequent analysis. Statistical differences were determined by the GraphPad Prism software.

Example 5: Immunization Using IPB 2033-2044 Effectively Stimulates Cytokines Secretion when Co-Administered with a Soluble Model Antigen As described in the protocols above, groups of mice (3-5 animals) were immunized either intranasal (i.n.) or intramuscular (i.m.) on days 0, 14 and 281 with PBS, or with Ovalbumin (30 µg); the latter were administered alone or with different adjuvants—c-di-AMP, aßGalCerMPEG or IPB 2033 to 2044—is shown in FIG. 5-11, intramuscular.

The data presented in FIG. 5 to 11 shows the immunization protocols, measurements of animal weight, measurements of cellular immune response via multifunctional CD4+ T cells and measurements of the systemic humoral immune responses via IgG titer.

As is shown in FIGS. 6 and 10, both intramuscular and intranasal administration had no detrimental effect on mice weight development during the immunization and sampling protocol, indicating no or negligible toxicity to the mice in this experimental setting.

As shown in FIGS. 7 and 11, both intramuscular and intranasal administration of the inventive adjuvants IPB 2033 to 2044 lead to enhanced antigen-specific IgG titer in sera of immunized mice. Of note is that the inventive adjuvants provide at least equivalent (IPB 2038, 2041, 2044 in i.m.; 2034, 2035, 2037, 2044 in i.n.), or in many cases improved stimulation (IPB 2033, 2034, 2035, 2036, 2037, 2039, 2040, 2042, 2043 in i.m.; 2033, 2036, 2038, 2039, 2040, 2041, 2042, 2043 in i.n.) of antigen specific IgG production compared to the structurally-related relevant control (aßGalCerMPEG+ova).

As shown in FIG. 8, the production of multifunctional CD4+ T cells is enhanced when using the inventive adjuvants IPB 2033 to 2044, using a readout of antigen-specific CD4+ T cells that express particular immune-stimulatory cytokines. All inventive adjuvants IPB 2033 to 2044 provide enhanced levels of these CD4+ T cells compared to the structurally-related relevant control (aßGalCerMPEG+ova), as is evident from staining and sorting cells according to e.g. IL-2 and TNFa, or any 2 of IL-2, TNFa or IFNg.

Synthesis and Analytical Chemistry

1. General Procedure for the Synthesis of Phytosphingosine Derivatives (Also Described as α-GalCer Analogues) by Ugi-4CR

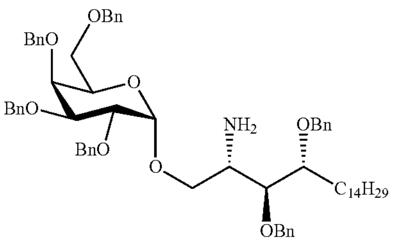

1

+

-continued

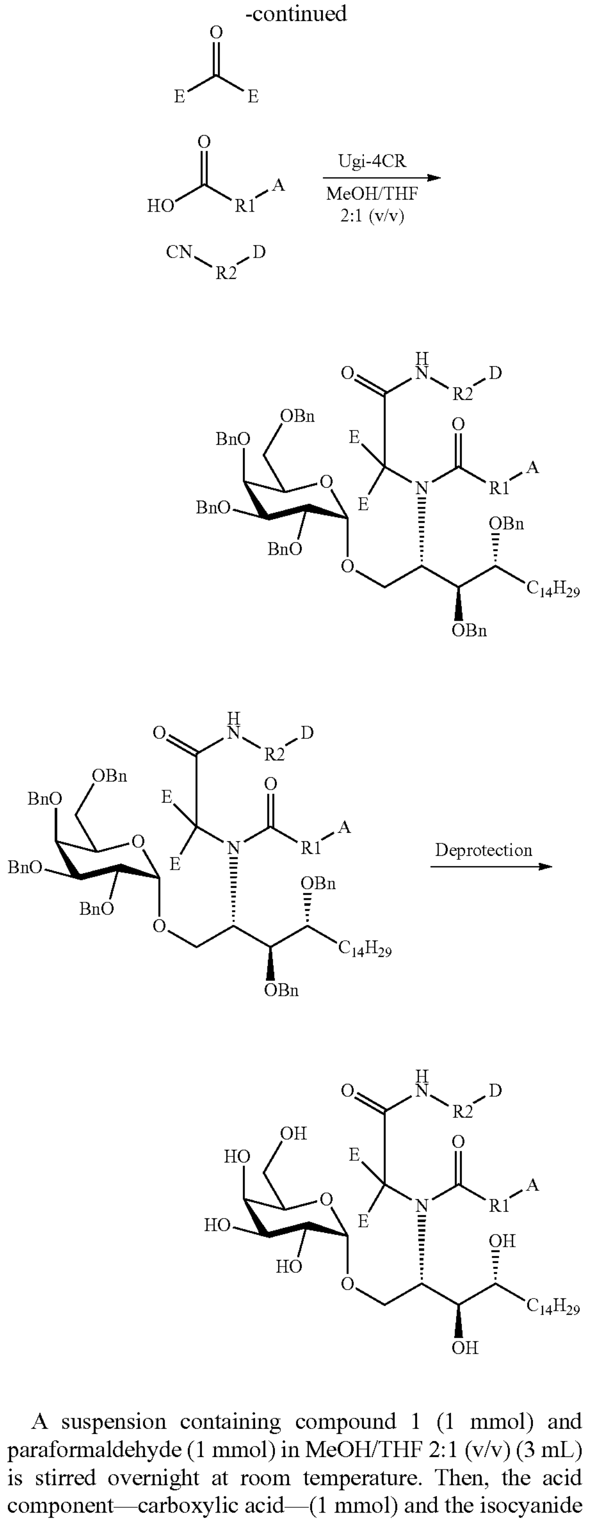

A suspension containing compound 1 (1 mmol) and paraformaldehyde (1 mmol) in MeOH/THF 2:1 (v/v) (3 mL) is stirred overnight at room temperature. Then, the acid component—carboxylic acid—(1 mmol) and the isocyanide (1 mmol) are added and the reaction mixture is protected from light and stirred at room temperature for 72 h. The product formation is checked by TLC, the volatiles are removed under high vacuum, and the obtained crude is purified by column chromatography (n-hexane/EtOAc) to obtain the protected α-GalCer analogue.

In other embodiments, the general procedure for the synthesis of α-GalCer analogues by Ugi-4CR may be as follows:

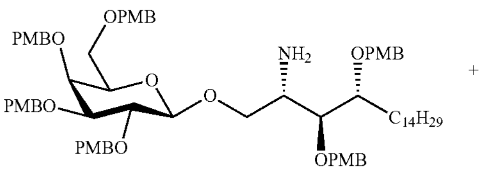

2

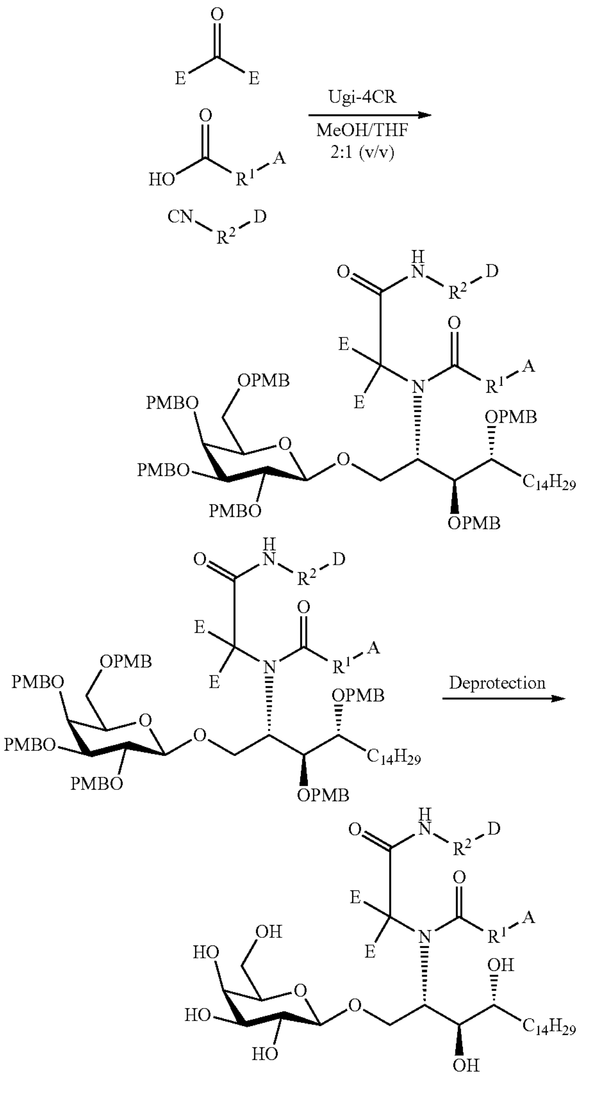

A suspension containing compound 2 (1 mmol) and paraformaldehyde (1 mmol) in MeOH/THF 2:1 (3 mL) is stirred overnight at room temperature. Then, the acid component—(1 mmol) and the isocyanide (1 mmol) are added and the reaction mixture is protected from light and stirred at room temperature for 72 h. The product formation is checked by TLC, the volatiles are removed under high vacuum, and the obtained crude is purified by column chromatography (n-hexane/EtOAc) to obtain the protected α-GalCer analogue.

2. General Procedure for the Benzyl Ether/Azide/4-Phenyl-1,3-Dioxolane Removal

To a three necked flask containing a suspension of Pd/C 10% (5 g per g of the α-GalCer analogue) in THF (1 mL) under nitrogen atmosphere, the Ugi-GalCer analogue—dissolved in THF (2 mL)—and formic acid (300 μL) are added and the reaction mixture is stirred for 4 h. The product formation is checked by ESI-MS, and finally the reaction mixture is filtered over celite and washed thoroughly with THF. All volatiles are removed under reduced pressure to afford the deprotected α-GalCer analogue.

3. General Procedure for the p-Methoxybenzyl Ether Removal

To a solution of the per-PMB-protected Ugi-GalCer analogue (0.01 mmol) in 1,4-dioxane (1 mL) are added sequentially anisole (0.1 mmol) and HCl (1 mL, 4M in 1,4-dioxane) at rt. The progress of the reaction is followed by ESI-MS. The volatiles are removed under reduced pressure to afford the deprotected α-GalCer analogue.

4. Synthesis of Isocyanides

The amine (1 mmol) is dissolved in ethyl formate, in the presence of base ($Et_3N$ or DIPEA) when necessary, and the solution is refluxed overnight at 70-80° C. The solvent is removed under reduced pressure and the corresponding formamide (checked by TLC) is purified when necessary and dissolved in dry DCM or THF. $Et_3N$ (5 mmol) and $POCl_3$ (1 mmol)—drop wise and over 15 min—are then added under nitrogen atmosphere at 0° C. and the reaction mixture is allowed to reach room temperature and stirred for 2 to 3 additional hours until completeness. A saturated solution of $NaHCO_3$ is added drop wise to neutralize and quench the reaction and the organic phase is separated and washed twice with brine. The volatiles are removed under reduced pressure and the product is immediately purified by column chromatography and stored under nitrogen atmosphere at −20° C.

4.1. Synthesis and Characterization of Isocyanide 31

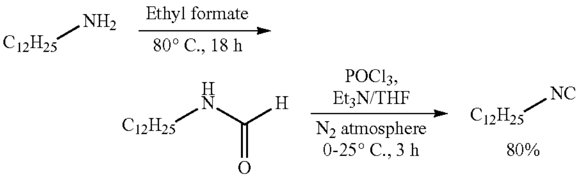

4.2. Synthesis and Characterization of Isocyanide 4

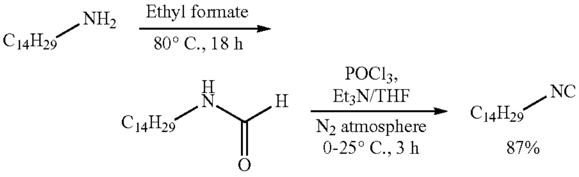

Tetradecylamine (3.0 g, 14.1 mmol) was subjected to the standard procedure for the isocyanide synthesis described in section 4 to afford isocyanide 4 (2.7 g, 87%) as a light-yellow oil over two steps and a final column chromatography purification (n-hexane/EtOAc 2:1); $R_f$=0.90 (n-hexane/

EtOAc 2:1). $^1$H NMR (400 MHz, $CDCl_3$): δ=0.87 (t, 3H, J=6.6 Hz, $CH_3$); 1.22-1.34 (m, 20H); 1.38-1.47 (m, 2H); 1.63-1.72 (m, 2H); 3.34-3.41 (m, 2H). $^{13}$C NMR (100 MHz, $CDCl_3$): δ=14.2 ($CH_3$); 22.8, 26.5, 28.8, 29.3, 29.5, 29.6, 29.7, 29.8, 32.1 ($CH_2$); 43.7 (t, J=6.0 Hz, $CH_2$); 155.7 (t, J=6.0 Hz, C≡N).

4.3. Synthesis and Characterization of Isocyanide 5[1]

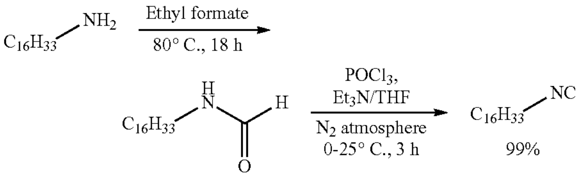

4.4. Synthesis and Characterization of s Isocyanide 6[1]

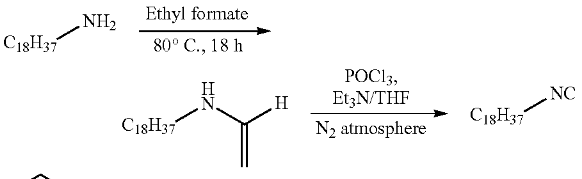

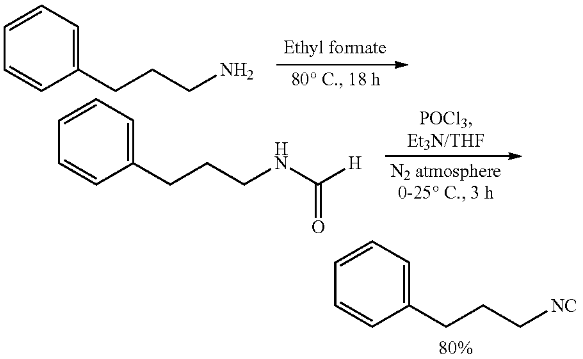

4.5. Synthesis and Characterization of Isocyanide 7

3-Phenylpropan-1-amine (5.0 g, 31 mmol) was subjected to the standard procedure for the isocyanide synthesis described in section 4 and the resulting product purified by column chromatography (n-hexane/EtOAc 4:1) to afford isocyanide 7 (3.6 g, 80%). $R_f$=0.85 (n-hexane/EtOAc 2:1). $^1$H NMR (400 MHz, $CDCl_3$): 1.93-2.05 (m, 2H, $CH_2$); 2.78 (t, 2H, J=7.4 Hz, $CH_2$); 3.32-3.39 (m, 2H, $CH_2$); 7.10-7.29 (m, 5H, Ar). $^{13}$C NMR (100 MHz, $CDCl_3$): δ=30.6, 32.3 ($CH_2$); 40.8 (t, J=6.5 Hz, $CH_2$); 126.5, 128.6, 128.7 (CH); 139.9 (C); 156.4 (t, J=5.7 Hz, C≡N).

4.6. Synthesis and Characterization of Isocyanide 8

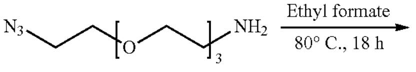

-continued

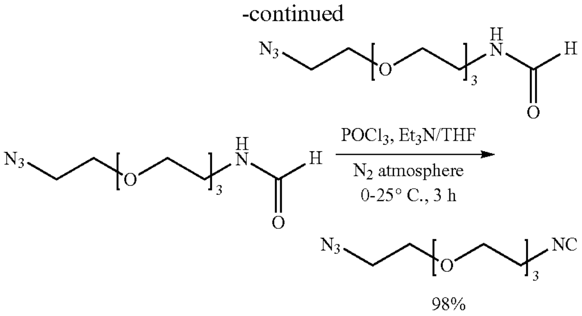

2-{2-[2-(2-Azidoethoxy)ethoxy]ethoxy}ethan-1-amine (1.0 g, 4.6 mmol) was subjected to the standard procedure for the isocyanide synthesis described in section 4 to afford isocyanide 8 (0.62 g, 59%) as a light yellow liquid over two steps and two column chromatography purifications: for the formamide (DCM/MeOH 20:1; $R_f$=0.86 (DCM/MeOH 10:1)); for the isocyanide (EtOAc/n-hexane 1:1; $R_f$=0.75 (EtOAc/n-hexane 1:2)). $^1$H NMR (400 MHz, $CDCl_3$): δ=3.39 (t, 2H, J=5.3 Hz, $CH_2$); 3.57 (t, 2H, J=5.3 Hz, $CH_2$); 3.64-3.74 (m, 12H, 6×$CH_2$); $^{13}$C NMR (100 MHz, $CDCl_3$): δ=41.9 (t, J=7.1 Hz, $CH_2$); 50.8, 68.8, 70.2, 70.8, 70.9, 71.0 ($CH_2$); 157.4 (t, J=5.5 Hz, C≡N).

4.7. Synthesis and Characterization of Isocyanide 9

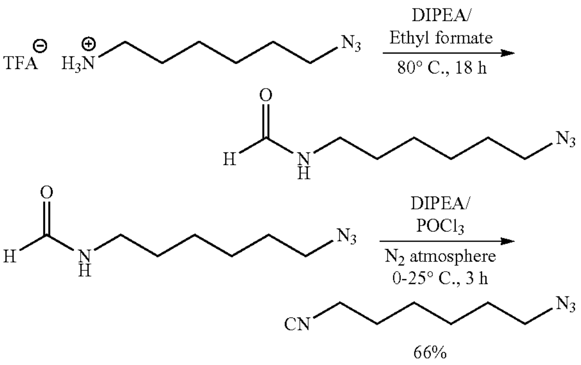

6-Azidohexan-1-amine (TFA salt) (1.17 g, 4.9 mmol) was subjected to the standard procedure for the isocyanide synthesis described in section 4 to afford isocyanide 9 (0.49 g, 66%) as a light yellow liquid over two steps and two column chromatography purifications: for the formamide (EtOAc/n-hexane 2:1-3:1; $R_f$=0.44 (EtOAc/n-hexane 1:1)); for the isocyanide (EtOAc/n-hexane 1:2; $R_f$=0.60 (EtOAc/n-hexane 1:4)). $^1$H NMR (400 MHz, $CDCl_3$): δ=1.36-1.54 (m, 4H, 2×$CH_2$); 1.57-1.75 (m, 4H, 2×$CH_2$); 3.28 (t, 2H, J=6.8 Hz, $CH_2$); 3.35-3.44 (m, 2H, $CH_2$); $^{13}$C NMR (100 MHz, $CDCl_3$): δ=26.0, 28.8, 29.9 ($CH_2$); 41.5 (t, J=6.4 Hz, $CH_2$); 51.8, ($CH_2$); 156.1 (t, J=5.8 Hz, C≡N).

4.8 Synthesis and Characterization of Isocyanide 10

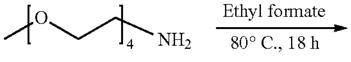

-continued

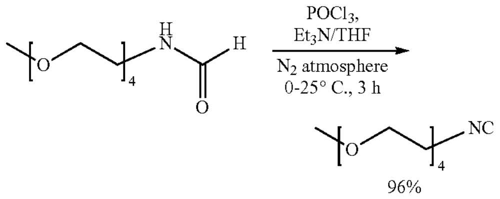

2,5,8,11-Tetraoxatridecan-13-amine (1.0 g, 4.8 mmol) was subjected to the standard procedure for the isocyanide synthesis described in section 4 and the resulting product purified by column chromatography (DCM/methanol 40:1) to afford isocyanide 10 (1.0 g, 96%) as a light yellow liquid; $R_f$=0.35 (DCM/methanol 30:1). $^1H$ NMR (400 MHz, $CDCl_3$): δ=3.36 (s, 3H, $CH_3$); 3.51-3.58 (m, 4H, 2×$CH_2$); 3.61-3.71 (m, 12H, 6×$CH_2$); $^{13}C$ NMR (100 MHz, $CDCl_3$): δ=41.8 (t, J=7.1 Hz, $CH_2$); 53.5 ($CH_2$); 59.1 ($CH_3$); 68.8, 70.6, 70.7, 70.9, 72.0 ($CH_2$); 157.3 (t, J=5.4 Hz, C≡N).

4.9. Synthesis and Characterization of Isocyanide 11

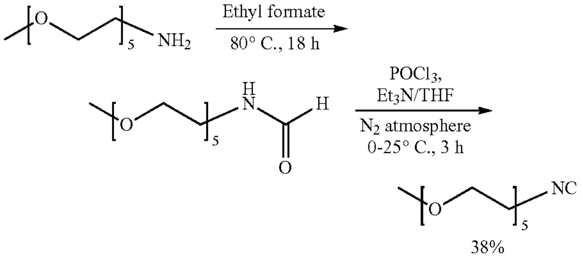

2,5,8,11,14-Pentaoxahexadecan-16-amine (1.0 g, 4.0 mmol) was subjected to the standard procedure for the isocyanide synthesis described in section 4 and the resulting product purified by column chromatography (DCM/methanol 40:1) to afford isocyanide 11 (0.40 g, 38%) as a light yellow liquid; $R_f$=0.37 (DCM/methanol 30:1). $^1H$ NMR (400 MHz, $CDCl_3$): δ=3.35 (s, 3H, $CH_3$); 3.50-3.59 (m, 4H, 2×$CH_2$); 3.60-3.72 (m, 16H, 8×$CH_2$); $^{13}C$ NMR (100 MHz, $CDCl_3$): δ=41.8 (t, J=7.1 Hz, $CH_2$); 59.1 ($CH_3$); 68.8, 70.6, 70.7, 70.9, 72.0 ($CH_2$); 157.3 (t, J=5.6 Hz, C≡N).

4.10. Synthesis and Characterization of Isocyanide 12

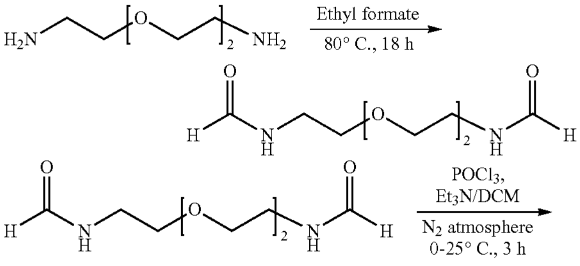

-continued

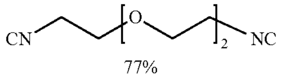

2,2'-(Ethane-1,2-diylbis(oxy))bis(ethan-1-amine) (2.0 g, 13.5 mmol) was subjected to the standard procedure for the isocyanide synthesis described in section 4 to afford isocyanide 12 (1.7 g, 77%) as a light yellow liquid over two steps and two column chromatography purifications: for the formamide (DCM/MeOH 20:1; $R_f$=0.42 (DCM/MeOH 10:1)); for the isocyanide (EtOAc/n-hexane 2:1; $R_f$=0.25 (EtOAc/n-hexane 1:1)). $^1H$ NMR (400 MHz, $CDCl_3$): δ=3.56-3.61 (m, 4H, 2×$CH_2$); 3.69-3.75 (m, 8H, 4×$CH_2$); $^{13}C$ NMR (100 MHz, $CDCl_3$): δ=42.0 (t, J=7.0 Hz, $CH_2$); 68.8, 71.0 ($CH_2$); 157.5 (t, J=5.7 Hz, C≡N).

4.11. Synthesis and Characterization of Isocyanide 13

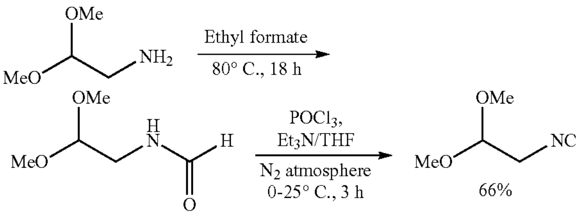

2,2-Dimethoxyethylamine (2.0 g, 19.0 mmol) was subjected to the standard procedure for the isocyanide synthesis described in section 4 to afford isocyanide 13 (1.5 g, 66%) as a light-yellow oil over two steps and a final column chromatography purification (n-hexane/EtOAc 1:1); $R_f$=0.85 (n-hexane/EtOAc 2:1). $^1H$ NMR (400 MHz, $CDCl_3$): δ=3.43 (s, 6H, 2×$OCH_3$); 3.50 (d, 2H, J=5.2 Hz, $CH_2$); 4.60 (d, 1H, J=5.2 Hz, CH). $^{13}C$ NMR (100 MHz, $CDCl_3$): δ=43.7 (t, J=7.5 Hz, $CH_2$); 54.5 ($OCH_3$); 101.1 (CH); 158.6 (t, J=5.2 Hz, C≡N).

4.12. Synthesis and Characterization of Isocyanide 14

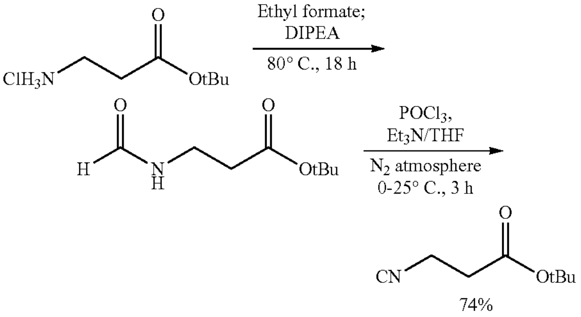

L-Alanine tert-butyl ester hydrochloride (4.0 g, 22.0 mmol) was subjected to the standard procedure for the isocyanide synthesis described in section 4 to afford isocyanide 14 (2.5 g, 74%) as a light yellow liquid over two steps and two column chromatography purifications: for the formamide (EtOAc/n-hexane 1:1-5:1; $R_f$=0.35 (EtOAc/n-hexane 1:1)); for the isocyanide (EtOAc/n-hexane 1:1; $R_f$=0.75 (EtOAc/n-hexane 1:2)). $^1H$ NMR (400 MHz, $CDCl_3$): δ=1.46 (s, 9H, 3×$CH_3$); 2.62 (tt, 2H, J=6.9/2.1 Hz, $CH_2$); 3.63 (tt, 2H, J=6.9/1.9 Hz, $CH_2$); $^{13}C$ NMR (100 MHz, $CDCl_3$): δ=28.1 ($CH_3$); 35.4, 37.6 ($CH_2$); 82.1 (C); 157.3 (t, J=5.4 Hz, C≡N); 168.7 (C═O).

4.13. Synthesis and Characterization of Isocyanide 15

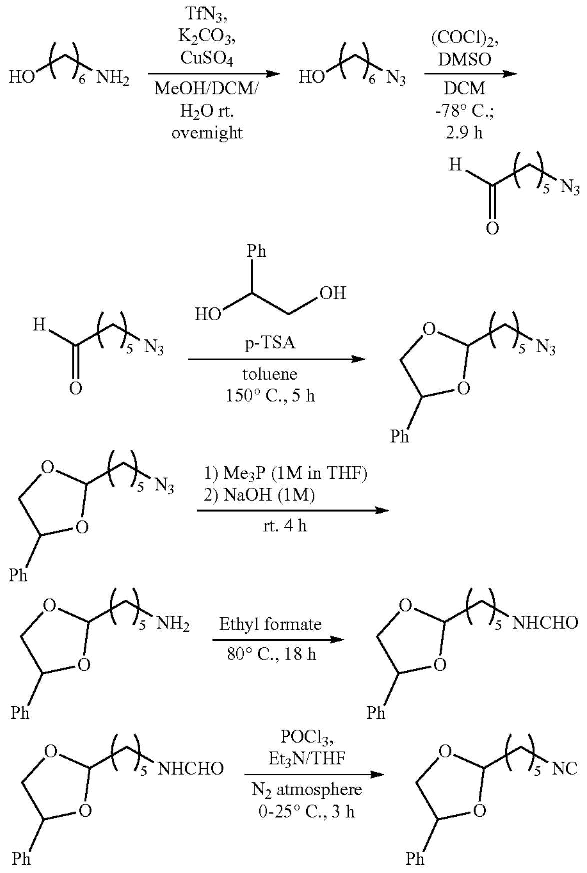

A solution containing $NaN_3$ (11.5 g, 177.2 mmol) in DCM/$H_2O$ 1:1 (40 mL) was cooled to 0° C., and $Tf_2O$ (10.0 g, 35.4 mmol) was added dropwise. After 2 h of stirring at 0° C., the organic phase was separated, the aqueous layer was extracted with DCM and the combined organic layers were washed with $H_2O$. This freshly prepared $TfN_3$ solution in DCM (20 mL) was added to a suspension of 6-amino-1-hexanol (2.0 g, 17.1 mmol), $K_2CO_3$ (4.3 g, 31.4 mmol), $CuSO_4$ (0.04 g, 0.2 mmol), in MeOH/$H_2O$ 3:1 (v:v) (160 mL). The reaction mixture was stirred overnight, filtered and the organic solvents were evaporated under reduced pressure. The remaining aqueous solution was extracted with EtOAc (5×30 mL) and the combined organic layer was washed with $H_2O$, $NH_4OH$ (12%) and brine, dried over $Na_2SO_4$ and concentrated under reduced pressure to afford 6-azido-1-hexanol (15a) (2.2 g, 89%) as a colorless oil. $R_f$=0.46 (n-hexane/EtOAc 2.1). $^1H$ NMR (400 MHz, $CDCl_3$): δ=1.26 (s, 1H, OH); 1.41 (p, 3H, J=3.6 Hz); 1.53-1.67 (m, 5H); 3.27 (t, 2H, J=6.9 Hz, $CH_2$); 3.65 (t, 2H, J=6.5 Hz, $CH_2$). $^{13}C$ NMR (100 MHz, $CDCl_3$): δ=25.5, 26.7, 29.0, 32.7, 51.5, 63.0 ($CH_2$). A solution of DMSO (4.3 mL, 60.9 mmol) in DCM (5 mL) was added over 30 min to a stirred solution of oxalyl chloride (2.6 mL, 30.5 mmol) in DCM (20 mL) at −78° C. Upon completion of the addition, the mixture was stirred at −78° C. for 5 min, followed by addition of a solution of 15a (2.2 g, 15.2 mmol) in DCM (5 mL) over 30 min at −78° C. and the resulting mixture was stirred for 40 min. Then $Et_3N$ (13 mL, 91.4 mmol) was added dropwise over 10 min. The resulting mixture was allowed to warm to 0° C. and stirred at 0° C. for 1 h. $H_2O$ (30 mL) was added to quench the reaction and the organic layer was then separated and further washed with $H_2O$ (2×20 mL) and brine (20 mL), dried over anhydrous $Na_2SO_4$, concentrated under reduced pressure, and the residue purified by column chromatography (n-hexane/EtOAc 4:1) to afford 6-azidohexanal (15b) (1.4 g, 65%) as a colorless oil. $R_f$=0.65 (n-hexane/EtOAc 4:1). $^1H$ NMR (400 MHz, $CDCl_3$): δ=1.35-1.48 (m, 2H); 1.56-1.71 (m, 4H); 2.46 (td, 2H, J=7.3/1.6 Hz, $CH_2$ α); 3.28 (t, 2H, J=6.8 Hz, $CH_2$); 9.77 (t, 1H; J=1.6 Hz, CHO). $^{13}C$ NMR (100 MHz, $CDCl_3$): δ=21.7, 26.4, 28.8, 43.8, 51.3 ($CH_2$); 202.3 (C═O). 15b (0.8 g, 5.7 mmol) was dissolved in toluene (200 mL) and then placed in a two necked flask equipped with a Dean Stark apparatus, a reflux condenser and a thermometer. Then, p-TSA (32 mg, 0.17 mmol) and 1-phenyl-1,2-ethanediol (1.96 g, 14.2 mmol) were added and the mixture was heated up until toluene distillation. The reaction was carried out for five hours and then the reaction mixture was allowed to cool down, diluted with diethyl ether and washed with a saturated $NaHCO_3$ solution (30 mL). The organic layer was further washed with $H_2O$ (2×30 mL) and brine (30 mL), dried over anhydrous $Na_2SO_4$ and concentrated under reduced pressure. The residue was purified by column chromatography (n-hexane/EtOAc 20:1) to afford the cyclic acetal 2-(5-azidopentyl)-4-phenyl-1,3-dioxolane (15c) (1.3 g, 85%) as a pale-yellow liquid. $R_f$=0.84 (n-hexane/EtOAc 4:1). For the major diastereomer: $^1H$ NMR (400 MHz, $CDCl_3$): δ=1.43-1.57 (m, 3H); 1.64 (p, 3H, J=7.1 Hz); 1.80-1.86 (m, 1H); 3.28 (t, 2H, J=6.9 Hz, $CH_2$); 3.75 (dd, 1H; J=7.7/6.3 Hz); 4.20 (t, 1H, J=7.7 Hz); 5.01 (t, 1H, J=6.3 Hz); 5.09 (t, 1H, J=4.7 Hz); 7.27-7.40 (m, 5H, Ar). $^{13}C$ NMR (100 MHz, $CDCl_3$): δ=23.8, 26.8, 28.9, 33.9, 51.5, 72.1 ($CH_2$); 78.5, 105.4, 126.5, 128.3, 128.7 (CH); 139.7 (C). A solution of trimethylphosphine in THF (24 mL, 1 M) was added dropwise to a solution of 15c (1.26 g, 4.8 mmol) in THF (10 mL) at room temperature. After stirring for 2 h at room temperature, a solution of NaOH (24 mL, 1 M) was added and the mixture was allowed to stir for additional 2 h. The reaction mixture was diluted with EtOAc (50 mL), washed with $H_2O$ (3×20 mL) and brine (20 mL), dried over $MgSO_4$, filtered, and evaporated to dryness to afford the corresponding amine[2] 5-(4-phenyl-1,3-dioxolan-2-yl)pentan-1-amine (15d) (quantitative) as a colorless oil, that was employed in the next step without further purification. $R_f$=0.11 (DCM/MeOH 20:1). For the major diastereomer: $^1H$ NMR (400 MHz, $CDCl_3$): δ=1.36-1.58 (m, 6H, 3×$CH_2$); 1.71-1.79 (m, 1H); 1.79-1.86 (m, 1H); 2.71 (t, 2H, J=6.8 Hz, $CH_2$); 3.74 (dd, 1H; J=7.7/6.8 Hz, $CH_2$); 4.19 (t, 1H, J=7.7 Hz, $CH_2$); 5.09 (t, 1H, J=6.8 Hz, CH); 5.09 (t, 1H, J=4.8 Hz, CH); 7.25-7.43 (m, 5H, Ar). $^{13}C$ NMR (100 MHz, $CDCl_3$): δ=24.1, 27.0, 33.7, 34.5, 42.2, 72.1 ($CH_2$); 78.4, 105.8, 126.5, 128.1, 128.7 (CH); 139.8 (C). 15d (0.89 g, 3.79 mmol) was subjected to the standard procedure for the isocyanide synthesis described in section 4 and the resulting product purified by column chromatography (n-hexane/EtOAc 4:1) to afford isocyanide 15 (0.35 g, 38%). $R_f$=0.79

(n-hexane/EtOAc 2:1). For the major diasteromer: $^1H$ NMR (400 MHz, $CDCl_3$): δ=1.48-1.61 (m, 5H); 1.66-1.89 (m, 3H); 3.37-3.43 (m, 2H, $CH_2$); 3.75 (dd, 1H; J=8.1/6.5 Hz, $CH_2$); 4.41 (dd, 1H, J=8.1/6.5 Hz, $CH_2$); 5.10 (t, 1H, J=6.5 Hz, CH); 5.26 (t, 1H, J=4.7 Hz, CH); 7.27-7.40 (m, 5H, Ar). $^{13}C$ NMR (100 MHz, $CDCl_3$): δ=23.3, 26.4, 29.2, 33.8, 41.5, 72.0 ($CH_2$); 78.5, 105.2, 126.5, 128.3, 128.7 (CH); 193.6 (C); 155.9 (t, J=5.7 Hz, C≡N).

4.14. Synthesis and Characterization of Isocyanide 16[3]

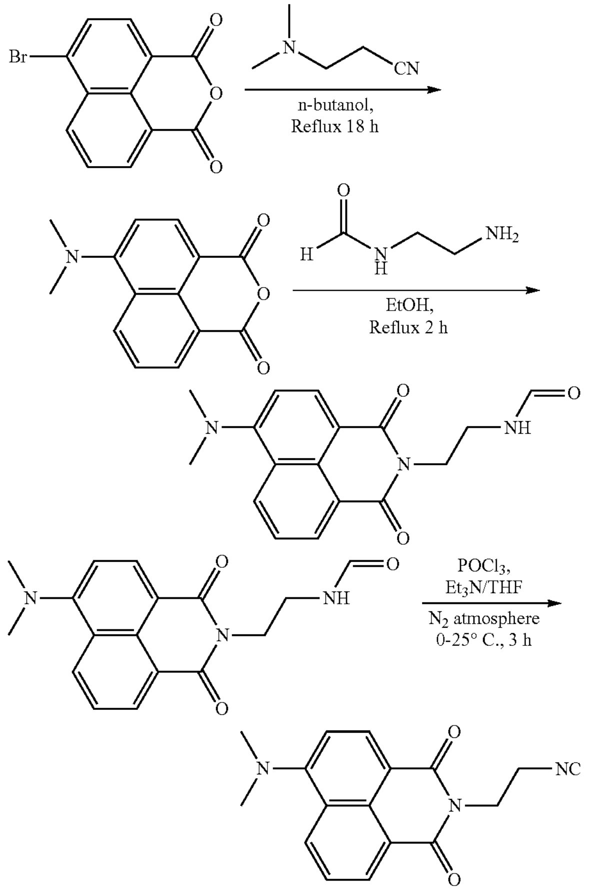

4.15. Synthesis and Characterization of Isocyanide 17

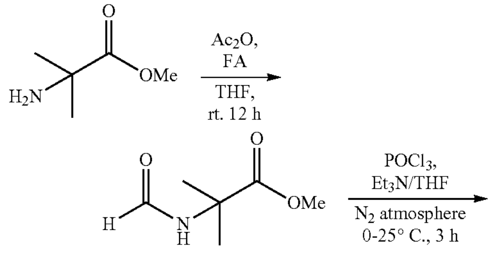

-continued

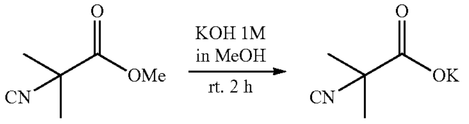

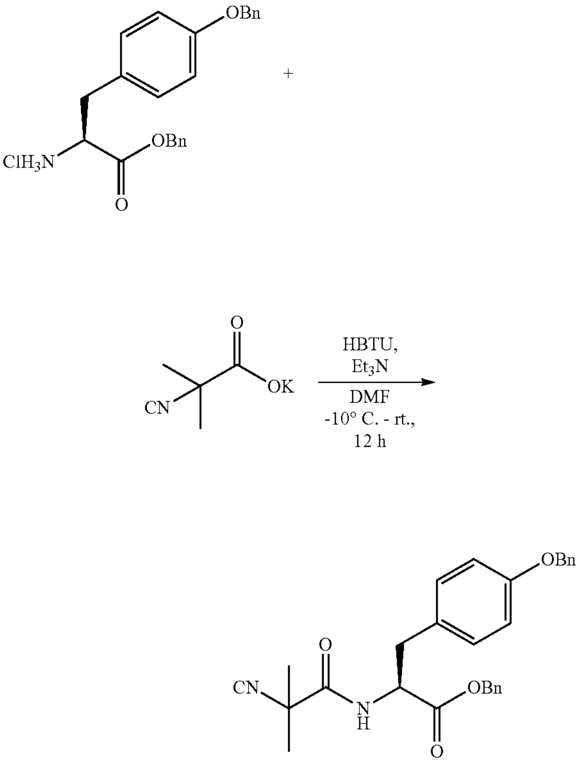

Formic acid (39.1 mL, 1164.1 mmol) and acetic anhydride (73.3 mL, 776.1 mmol) were mixed and reacted for 3 h at 60° C. To the cooled mixture diluted with THF, methyl α-aminoisobutyrate (9.1 g, 77.6 mmol) was added. After stirring for 12 h at room temperature, the crude mixture was co-evaporated with toluene under reduced pressure and then diluted with EtOAc (200 mL), washed with $H_2O$ (50 mL) and brine (50 mL) and the organic phase dried over $Na_2SO_4$. The volatiles were removed under reduced pressure to afford 17a as a yellowish liquid (10.3 g, 92%). $R_f$=0.23 (n-hexane/EtOAc 1:1). 17a (10.3 g, 71.0 mmol) was dissolved in DCM (100 mL) and $Et_3N$ (49.5 mL, 355.1 mmol) and $POCl_3$ (7.9 mL, 85.2 mmol)—drop wise and over 15 min—were subsequently added under nitrogen atmosphere and the reaction mixture was stirred for 2 to 3 h until completeness. A saturated solution of $NaHCO_3$ (10 mL) was added drop wise and the organic phase was separated and washed with brine (2×20 mL). All volatiles were removed under reduced pressure and the product was purified by column chromatography (n-hexane/EtOAc 10:1-6:1) to afford 17b as a yellowish liquid (9.0 g, >99%). Rf=0.81 (n-hexane/EtOAc 1:1). 17b (2 g, 15.6 mmol) was mixed with a solution of KOH (3 mL, 1 M in MeOH) and the mixture was stirred for 2 h at room temperature. The product formation was checked by TLC and ESI-MS and after completeness, the volatiles were removed under reduced pressure and the product (17c) stored without further purification step. Triethylamine (2.2 mL, 15.8 mmol) was added dropwise to a mixture of 17c (1.2 g, 9.8 mmol) and L-Tyr(Bn)-OBzl-HCl (3.0 g, 7.5 mmol) in DMF (5 mL). After stirring for 20 min at room temperature, the reaction mixture was cooled to −10° C. (ice-salt bath; internal thermometer). HBTU (4.3 g, 11.3 mmol) was added and the mixture was stirred for 12 h until reaction completion (monitored by TLC). The reaction mixture was then diluted with EtOAc (100 mL), transferred to a separatory funnel and washed with brine (50 mL). The organic phase was dried over anhydrous $Na_2SO_4$ and concentrated under reduced pressure to dryness. The crude product was purified by column chromatography (n-hexane/EtOAc 6:1) to afford isocyanide 17 (1.5 g, 44%). $R_f$=0.24 (n-hexane/EtOAc 6:1). $^1H$ NMR (400 MHz, $CDCl_3$): δ=1.55 (s, 3H, $CH_3$); 1.58 (s, 3H, $CH_3$); 3.03-3.19 (m, 2H, $CH_2$); 4.79 (dt, 1H, J=7.9/6.0 Hz, CH); 5.02 (s, 2H, $CH_2$); 5.13 (d, 1H, J=12.1 Hz, $CH_2$); 5.23 (d, 1H, J=12.1 Hz, $CH_2$); 6.86 (d, 2H, J=8.6 Hz, 2×CH, Ar); 6.95 (d, 2H, J=8.6 Hz, 2×CH, Ar); 7.30-7.45 (m, 10H, Ar). $^{13}C$ NMR (100 MHz, $CDCl_3$): δ=27.7, 27.8 ($CH_3$); 36.9 ($CH_2$); 53.7 (CH); 67.6, 70.1 ($CH_2$); 115.3, 127.4, 127.6, 128.1, 128.8, 130.4 (CH); 135.1, 137.0, 158.2 (C); 160.6 (t, J=3.6 Hz, C≡N); 168.8 (C); 170.7 (C═O).

5.1. Synthesis of α-GalCer Analogue 19 (IPB001901

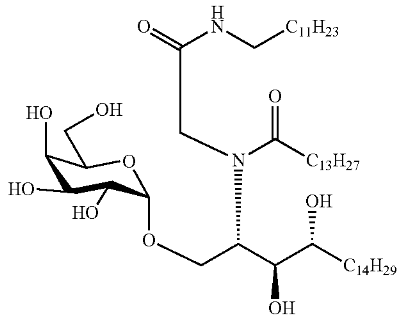

1 (50 mg, 0.05 mmol), paraformaldehyde (1.5 mg, 0.05 mmol), myristic acid (11 mg, 0.05 mmol) and lauric isocyanide 3 (9.6 μL, 0.05 mmol) in MeOH/THF (3 mL) reacted following the general procedure for the synthesis of α-GalCer analogues by Ugi-4CR (section 1). Column chromatography (n-hexane/EtOAc 5:1) afforded the protected Ugi product 18 (60 mg, 84%). $R_f$=0.24 (n-hexane/EtOAc 5:1) that was further deprotected following the general procedure for the benzyl ether protecting group removal (section 2) to afford the α-GalCer analogue 19 (33 mg, 88%) as a colorless oil. $[\alpha]_D^{23.5}$=23.9 (c 1.0 $CHCl_3$). $^1H$ NMR (400 MHz, $CDCl_3$): δ=0.87 (t, 9H, J=6.7 Hz, 3×$CH_3$); 0.98-1.36 (m, 61H); 1.36-1.67 (m, 9H), 2.17 (s, 1H); 2.26 (d, 1H, J=8.8 Hz); 2.32 (t, 1H, J=7.5 Hz); 3.08-3.26 (m, 2H); 3.47 (s, 2H); 3.55-4.31 (m); 7.43 (t, 1H, J=7.5 Hz, NH). $^{13}C$ NMR (100 MHz, $CDCl_3$): δ=14.2 ($CH_3$); 22.8, 25.0, 29.3, 29.4, 29.5, 29.6, 29.8, 29.9, 30.0, 32.1, 34.1, 40.0 ($CH_2$); 50.8 (CH); 63.5 ($CH_2$), 70.3, 77.4 (CH); 178.1 (C═O). HRMS: m/z=937.7428 [M+Na]$^+$ (calculated for $C_{52}H_{102}N_2NaO_{10}$: 937.7432).

5.2. Synthesis of α-GalCer Analogue 21 (IPB002040

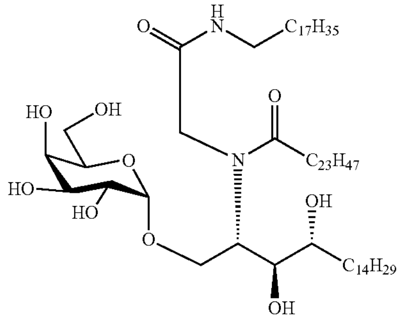

1 (150 mg, 0.15 mmol), paraformaldehyde (4.4 mg, 0.15 mmol), lignoceric acid (54 mg, 0.15 mmol) and stearic isocyanide 6 (41 mg, 0.15 mmol) in MeOH/THF (6 mL) reacted following the general procedure for the synthesis of α-GalCer analogues by Ugi-4CR (section 1). Column chromatography (n-hexane/EtOAc 10:1) afforded the protected Ugi product 20 (160 mg, 65%). $R_f$=0.33 (n-hexane/EtOAc 10:1) that was further deprotected following the general procedure for the benzyl ether protecting group removal (section 2) to afford the α-GalCer analogue 21 (68 mg, 63%) as a colorless oil. $[\alpha]_D^{23.5}$=ND. $^1H$ NMR (400 MHz, DMSO-$d_6$): 5=0.85 (t, 9H, J=6.8 Hz, 3×$CH_3$); 1.13-1.38 (m, 70H); 1.38-1.68 (m, 30H); 2.31-2.34 (m); 2.39-2.45 (m, 2H), 3.36-4.27 (m). $^{13}C$ NMR* (100 MHz, $CDCl_3$): δ=13.8 ($CH_3$); 22.0, 24.3, 25.4, 28.8, 29.0, 31.2, 68.8 ($CH_2$); 69.7 (CH); 70.3 ($CH_2$), 70.2, 70.8, 71.6 (CH). HRMS: m/z=1140.0106 [M+H]$^+$ (calculated for $C_{68}H_{135}N_2O_{10}$: 1140.0117).

5.3. Synthesis of α-GalCer Analogue 23 (IPB002033)

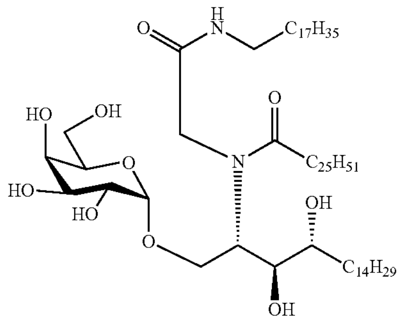

1 (150 mg, 0.15 mmol), paraformaldehyde (4.4 mg, 0.15 mmol), cerotic acid (58 mg, 0.15 mmol) and stearic isocyanide 6 (41 mg, 0.15 mmol) in MeOH/THF (6 mL) reacted following the general procedure for the synthesis of α-GalCer analogues by Ugi-4CR (section 1). Column chromatography (n-hexane/EtOAc 10:1) afforded the protected Ugi product 22 (140 mg, 56%). $R_f$=0.33 (n-hexane/EtOAc 10:1) that was further deprotected following the general procedure for the benzyl ether protecting group removal (section 2) to afford the α-GalCer analogue 23 (47 mg, 49%) as a colorless oil. $[\alpha]_D^{23.5}$=ND. $^1H$ NMR (400 MHz, DMSO-$d_6$): δ=0.80-

0.89 (m, 9H, 3×$CH_3$); 1.14-59 (m, 104H); 1.95-2.10 (m); 2.30-2.33 (m, 2H); 3.13-4.66 (m); $^{13}C$ NMR* (100 MHz, DMSO-$d_6$): δ=13.8 ($CH_3$); 21.9, 23.0, 25.2, 25.5, 28.6, 28.8, 31.2 39.6 ($CH_2$); 48.5 (CH); 61.9 ($CH_2$). HRMS: m/z=1168.0422 $[M+H]^+$ (calculated for $C_{70}H_{139}N_2O_{10}$: 1168.0430).

5.4. Synthesis of α-GalCer Analogue 25 (IPB001902

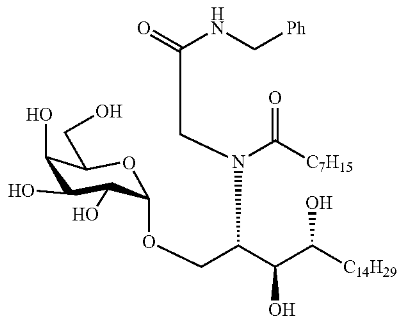

1 (70 mg, 0.07 mmol), paraformaldehyde (2.1 mg, 0.07 mmol), octanoic acid (11 μL, 0.07 mmol) and benzyl isocyanide (8 μL, 0.07 mmol) in MeOH/THF (3 mL) reacted following the general procedure for the synthesis of α-GalCer analogues by Ugi-4CR (section 1). Column chromatography (n-hexane/EtOAc 5:1) afforded the protected Ugi product 24 (36 mg, 40%). $R_f$=0.31 (n-hexane/EtOAc 5:1) that was further deprotected following the general procedure for the benzyl ether protecting group removal (section 2) to afford the α-GalCer analogue 25 (20 mg, 95%) as a colorless oil. $[\alpha]_D^{24.2}$=52.9 (c 1.0 $CHCl_3$). $^1H$ NMR (400 MHz, $CDCl_3$): δ=0.87 (t, 6H, J=6.6 Hz, 2×$CH_3$); 1.07-1.39 (m, 34H); 1.61 (p, 2H, J=6.6 Hz); 2.31 (t, 2H, J=7.5 Hz); 3.35-3.44 (m, 2H); 3.25 (s, 2H); 3.47-3.78 (m); 7.11-7.37 (m, 5H, Ar); 7.43 (t, 1H, J=7.6 Hz, NH). $^{13}C$ NMR (100 MHz, $CDCl_3$): δ=14.2 ($CH_3$); 22.7, 22.8, 24.9, 29.0, 29.2, 29.5, 29.8, 31.8, 32.0, 34.1, 45.9 ($CH_2$); 50.8 (CH); 63.7, 68.6, 70.6 ($CH_2$), 75.1, 75.2, 77.4, 128.5, 128.7, 130.2 (CH); 178.7 (C═O). HRMS: m/z=775.5078 $[M+Na]^+$ (calculated for $C_{41}H_{72}N_2NaO_{10}$: 775.5085).

5.5. Synthesis of α-GalCer Analogue 27 (IPB002042

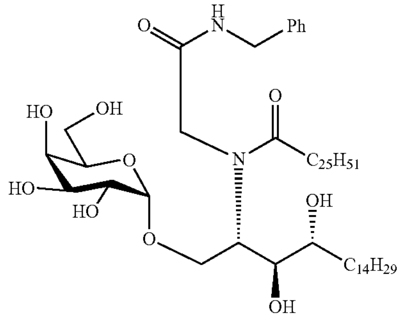

1 (150 mg, 0.15 mmol), paraformaldehyde (4.4 mg, 0.15 mmol), cerotic acid (58 mg, 0.15 mmol) and benzyl isocyanide (18 μL, 0.15 mmol) in MeOH/THF (6 mL) reacted following the general procedure for the synthesis of α-GalCer analogues by Ugi-4CR (section). Column chromatography (n-hexane/EtOAc 7:1) afforded the protected Ugi product 26 (85 mg, 37%). $R_f$=0.35 (n-hexane/EtOAc 6:1) that was further deprotected following the general procedure for the benzyl ether protecting group removal (section 2) to afford the α-GalCer analogue 27 (53 mg, 96%) as a colorless oil. $[\alpha]_D^{24.2}$=20.0 (c 1.0 $CHCl_3$). $^1H$ NMR (400 MHz, DMSO-$d_6$): δ=0.82 (t, 6H, J=6.6 Hz, 2×$CH_3$); 1.10-1.30 (m, 64H); 1.32-1.59 (m, 10H); 2.32-2.39 (m, 2H); 3.24-3.28 (m, 2H); 3.34-3.37 (m, 2H); 3.37-3.40 (m, 1H); 3.40-4.60 (m); 7.18-7.31 (m, 5H, Ar); 7.95 (t, 1H, J=6.3 Hz, NH). $^{13}C$ NMR (100 MHz, DMSO-$d_6$): δ=13.9 ($CH_3$); 22.0, 24.6, 24.8, 25.4, 28.7, 29.0, 29.1, 30.7, 31.3, 33.1 ($CH_2$), 39.4 (CH); 42.0; 46.4, 60.4 ($CH_2$), 68.2, 68.5, 69.7, 71.3, 98.9, 126.3, 126.9, 128.0 (CH); 162.8, 165.9 (C═O). HRMS: m/z=1005.8065 $[M+H]^+$ (calculated for $C_{59}H_{109}N_2O_{10}$: 1005.8082).

5.6. Synthesis of α-GalCer Analogue 29 (IPB002037)

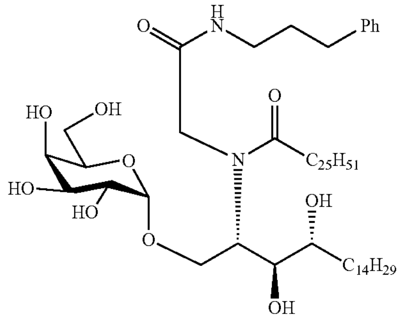

1 (150 mg, 0.15 mmol), paraformaldehyde (4.4 mg, 0.15 mmol), cerotic acid (58 mg, 0.15 mmol) and 3-phenylpropyl isocyanide 7 (21 mg, 0.15 mmol) in MeOH/THF (6 mL) reacted following the general procedure for the synthesis of α-GalCer analogues by Ugi-4CR (section 1). Column chromatography (n-hexane/EtOAc 7:1) afforded the protected Ugi product 27 (110 mg, 46%). $R_f$=0.34 (n-hexane/EtOAc 6:1) that was further deprotected following the general procedure for the benzyl ether protecting group removal (section 2) to afford the α-GalCer analogue 29 (70 mg, 97%) as a colorless oil. $[\alpha]_D^{24.2}$=34.6 (c 1.0 $CHCl_3$). $^1H$ NMR (400 MHz, DMSO-$d_6$): δ=0.84 (t, 6H, J=6.3 Hz, 2×$CH_3$); 1.10-1.33 (m, 61H); 1.34-1.57 (m, 8H); 1.58-1.74 (m, 4H); 2.30-2.40 (m, 2H); 2.98-3.07 (m, 2H); 3.08-3.19 (m, 3H); 3.40-4.90 (m); 7.10-7.26 (m, 5H, Ar); 7.56 (t, 1H, J=6.6 Hz, NH). $^{13}C$ NMR (100 MHz, DMSO-$d_6$): δ=13.7 ($CH_3$); 20.9, 22.2, 24.5, 24.9, 26.5, 27.3, 28.0, 29.0, 30.0, 31.3, 31.4, 32.3, 32.4, 33.1, 38.2 ($CH_2$), 39.7 (CH); 46.4 ($CH_2$), 57.1 (CH), 60.3, 64.3 ($CH_2$), 68.6, 68.7, 69.7, 71.2, 75.7, 99.0, 125.4, 126.3, 128.1 (CH); 166.0 (C═O). HRMS: m/z=1033.8365 $[M+H]^+$ (calculated for $C_{61}H_{113}N_2O_{10}$: 1033.8395).

5.7. Synthesis of α-GalCer Analogue 31 (IPB001903

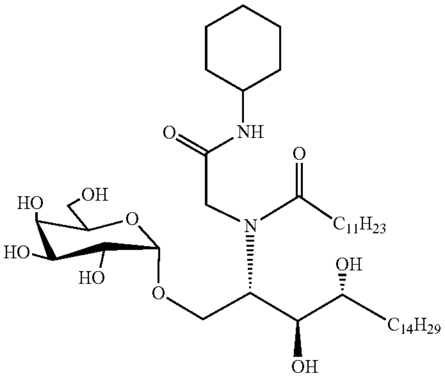

1 (50 mg, 0.05 mmol), paraformaldehyde (1.5 mg, 0.05 mmol), lauric acid (9.8 mg, 0.05 mmol) and cyclohexyl isocyanide (6.0 μL, 0.05 mmol) in MeOH/THF (3 mL) reacted following the general procedure for the synthesis of α-GalCer analogues by Ugi-4CR (section 1). Column chromatography (n-hexane/EtOAc 5:1) afforded the protected Ugi product 30 (36 mg, 54%), $R_f$=0.34 (n-hexane/EtOAc 5:1) that was further deprotected following the general procedure for the benzyl ether protecting group removal (section 2) to afford the α-GalCer analogue 31 (20 mg, 93%) as a colorless oil. $[\alpha]_D^{24.7}$=30.8 (c 1.0 $CHCl_3$). $^1$H NMR (400 MHz, $CDCl_3$): δ=0.87 (t, 6H, J=6.6 Hz, 2×$CH_3$); 1.07-1.40 (m, 44H); 1.49-1.89 (m, 10H); 1.53 (s, 1H); 1.57 (s, 1H); 2.04 (s, 1H); 2.26 (s, 1H); 2.28-2.33 (m, 2H); 3.35-3.44 (m, 2H); 3.43-3.56 (m, 2H); 3.55-4.30 (m); 7.42 (t, 1H, J=7.5 Hz, NH). $^{13}$C NMR (100 MHz, $CDCl_3$): δ=14.2 ($CH_3$); 22.8, 25.0, 29.5, 29.9, 30.0, 32.1, 34.5, 68.6 ($CH_2$), 70.2 (CH); 70.7 ($CH_2$), 75.1, 75.3, 77.4, 110.0 (CH); 174.7, 175.8 (C═O).

5.8. Synthesis of α-GalCer Analogue 33 (IPB002039

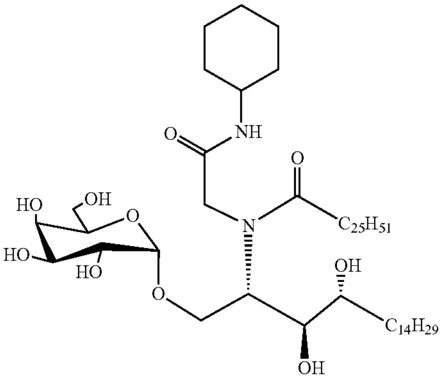

1 (150 mg, 0.15 mmol), paraformaldehyde (4.4 mg, 0.15 mmol), cerotic acid (58 mg, 0.15 mmol) and cyclohexyl isocyanide (18 μL, 0.15 mmol) in MeOH/THF (6 mL) reacted following the general procedure for the synthesis of α-GalCer analogues by Ugi-4CR (section 1). Column chromatography (n-hexane/EtOAc 8:1) afforded the protected Ugi product 32 (108 mg, 48%), $R_f$=0.24 (n-hexane/EtOAc 8:1) that was further deprotected following the general procedure for the benzyl ether protecting group removal (section 2) to afford the α-GalCer analogue 33 (68 mg, 97%) as a colorless oil. $[\alpha]_D^{24.7}$=36.1 (c 1.0 $CHCl_3$). $^1$H NMR (400 MHz, $CDCl_3$): δ=0.88 (t, 6H, J=6.7 Hz, 2×$CH_3$); 1.11-1.38 (m, 70H), 1.46-2.03 (m, 15H); 2.13-2.48 (m, 5H); 3.44-4.96 (m). $^{13}$C NMR* (100 MHz, $CDCl_3$) δ=14.1 ($CH_3$); 22.7, 24.7, 25.3, 25.6, 29.7, 31.9, 32.6, 33.6 ($CH_2$), 48.8, 70.4 (CH). HRMS: m/z=997.8374 [M+H]$^+$ (calculated for $C_{58}H_{113}N_2O_{10}$: 997.8395).

5.9. Synthesis of α-GalCer Analogue 35 (IPB001904

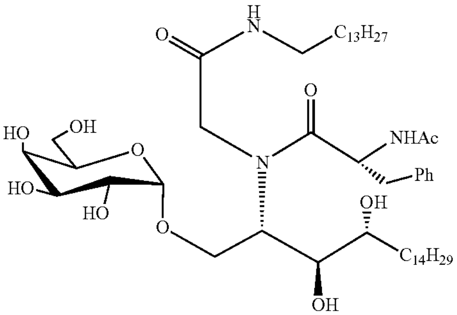

1 (80 mg, 0.08 mmol), paraformaldehyde (2.4 mg, 0.08 mmol), L-Phe (Ac) (16 mg, 0.08 mmol) and myristic isocyanide 4 (18 mg, 0.08 mmol) in MeOH/THF reacted following the general procedure for the synthesis of α-GalCer analogues by Ugi-4CR (section 1). Column chromatography (n-hexane/EtOAc 3:1) afforded the protected Ugi product 34 (34 mg, 30%), $R_f$=0.27 (n-hexane/EtOAc 4:1) that was further deprotected following the general procedure for the benzyl ether protecting group removal (section 2) to afford the α-GalCer analogue 35 (21 mg, 98%) as a colorless oil. $[\alpha]_D^{23.2}$=25.1 (c 1.0 $CHCl_3$). $^1$H NMR (400 MHz, $CDCl_3$): δ=0.87 (t, 6H, J=6.6 Hz, 2×$CH_3$); 1.10-1.34 (m, 50H); 1.38 (s, 1H); 2.05 (s, 1H); 2.17 (s, 1H); 2.24 (s, 1H); 3.35-3.44 (m, 2H); 3.46-3.52 (m, 2H); 3.55-3.76 (m); 7.10-7.25 (m, 5H, Ar); 7.44 (t, 1H, J=7.7 Hz, NH). $^{13}$C NMR (100 MHz, $CDCl_3$): δ=14.3, 17.3, 18.5 ($CH_3$); 22.8, 27.3, 29.5, 29.6, 29.9, 30.0, 30.1, 32.1, 40.4, 58.6, 68.6, 70.7 ($CH_2$); 75.1, 77.4, 110.1, 117.4, 121.1, 127.0, 128.6, 129.2 (CH); 136.9 (C). HRMS: m/z=944.6534 [M+Na]$^+$ (calculated for $C_{51}H_{91}N_3NaO_{11}$: 944.6551).

5.10. Synthesis of α-GalCer Analogue 37 (IPB001905

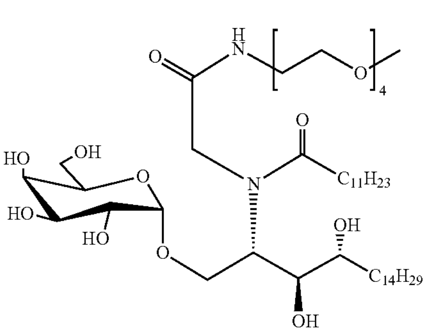

1 (57 mg, 0.056 mmol), paraformaldehyde (1.7 mg, 0.056 mmol), lauric acid (11 mg, 0.056 mmol) and isocyanide 10 (12 mg, 0.057 mmol) in MeOH/THF (3 mL) reacted following the general procedure for the synthesis of α-GalCer analogues by Ugi-4CR (5). Column chromatography (n-hexane/EtOAc 5:1) afforded the protected Ugi product 36 (43 mg, 52%). $R_f$=0.34 (n-hexane/EtOAc 5:1) that was further deprotected following the general procedure for the benzyl ether protecting group removal (section 2) to afford the α-GalCer analogue 37 (25 mg, 94%) as a colorless oil. $[\alpha]_D^{23.6}$=16.4 (c 1.0 $CHCl_3$). $^1H$ NMR (400 MHz, $CD_3OD$): δ=0.91 (t, 6H, J=6.6 Hz, $2\times CH_3$); 1.12-1.18 (m, 14H); 1.25-1.40 (m, 31H); 2.00 (s, 2H); 3.37 (s, 1H); 3.38-3.73 (m); 7.46 (t, 1H, J=7.7 Hz, NH). $^{13}C$ NMR (100 MHz, $CD_3OD$): δ=14.4, 17.5 ($CH_3$); 23.7, 26.3, 29.6, 29.8, 29.9, 30.5, 30.8, 33.1, 40.4 ($CH_2$); 59.2 ($CH_3$); 62.0, 62.2, 64.3, 69.6, 71.1, 71.3, 71.5. ($CH_2$); 73.0, 73.6 (CH); 76.1 ($CH_2$); 78.0, 100.8 (CH); 172.8 (C═O). HRMS: m/z=931.6423 $[M+Na]^+$ (calculated for $C_{47}H_{92}N_2NaO_{14}$: 931.6446).

5.11. Synthesis of α-GalCer Analogue 39 (IPB001906

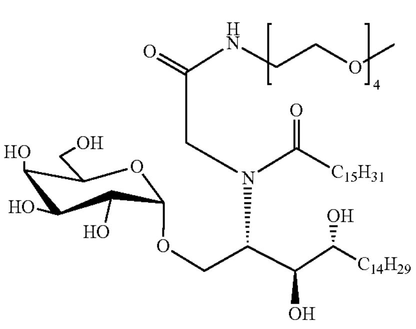

1 (62 mg, 0.061 mmol), paraformaldehyde (1.8 mg, 0.061 mmol), palmitic acid (16 mg, 0.061 mmol) and isocyanide 10 (13.2 mg, 0.061 mmol) in MeOH/THF (3 mL) reacted following the general procedure for the synthesis of α-GalCer analogues by Ugi-4CR (section 1). Column chromatography (n-hexane/EtOAc 1:2) afforded the protected Ugi product 38 (46.7 mg, 51%). $R_f$=0.31 (n-hexane/EtOAc 1:1) that was further deprotected following the general procedure for the benzyl ether protecting group removal (section 2) to afford the α-GalCer analogue 39 (18 mg, 60%) as a colorless oil. $[\alpha]_D^{23.4}$=12.9 (c 1.0 $CHCl_3$). $^1H$ NMR (400 MHz, $CDCl_3$): δ=0.87 (t, 6H, J=7.0 Hz, $2\times CH_3$); 1.08-1.61 (m, 54H); 1.96-2.41 (m); 3.03 (q, 2H; J=7.3 Hz); 3.34-4.36 (m); 7.45 (t, 1H; J=7.8 Hz, NH); 8.05-8.10 (m, 1H). $^{13}C$ NMR (100 MHz, $CDCl_3$): δ=14.3, 17.4 ($CH_3$); 22.8, 29.5, 29.8, 29.9, 32.1, 42.3 ($CH_2$); 59.1 ($CH_3$); 68.6, 70.7, 70.9, 71.0, 71.1 ($CH_2$); 75.1 (CH); 75.3 ($CH_2$); 77.4, (CH); 169.3 (C═O). HRMS: m/z=987.7045 $[M+Na]^+$ (calculated for $C_{51}H_{100}N_2NaO_{14}$: 987.7072).

5.12. Synthesis of α-GalCer Analogue 41 (IPB002036)

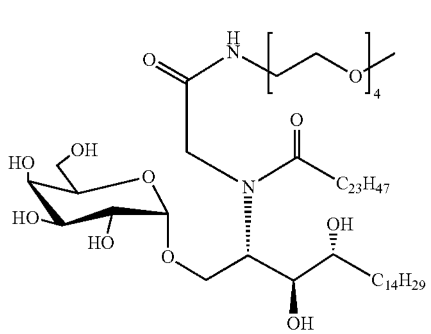

1 (150 mg, 0.15 mmol), paraformaldehyde (4.4 mg, 0.15 mmol), lignoceric acid (54 mg, 0.15 mmol) and isocyanide 10 (31.9 mg, 0.15 mmol) in MeOH/THF (6 mL) reacted following the general procedure for the synthesis of α-GalCer analogues by Ugi-4CR (section 1). Column chromatography (n-hexane/EtOAc 2:1) afforded the protected Ugi product 40 (139 mg, 58%). $R_f$=0.15 (n-hexane/EtOAc 2:1) that was further deprotected following the general procedure for the benzyl ether protecting group removal (section 2) to afford the α-GalCer analogue 41 (91 mg, 98%) as a colorless oil. $[\alpha]_D^{23.4}$=28.5 (c 1.0 $CHCl_3$). $^1H$ NMR (400 MHz, DMSO-$d_6$): δ=0.84 (t, 6H, J=6.5 Hz, $2\times CH_3$); 1.12-1.32 (m, 60H); 1.33-1.56 (m, 8H), 1.73-1.79 (m, 3H), 3.22-3.26 (m, 4H); 3.39-3.45 (m, 4H); 3.47-3.53 (m); 3.56-3.63 (m); 3.66-4.66 (m); 7.55 (t, 1H, J=5.8 Hz, NH); $^{13}C$ NMR* (100 MHz, DMSO-$d_6$) δ=13.8, ($CH_3$); 22.1, 23.3, 24.2, 24.6, 24.9, 26.5, 27.3, 28.0, 29.1, 30.1, 31.4, 32.4, 32.6, 33.0, 33.7, 38.4 ($CH_2$); 46.3 ($CH_2$); 58.0 ($CH_3$); 60.3, 64.2, 64.3, 67.0 ($CH_2$); 68.2, 68.6 (CH); 68.9, 69.7, 71.3 ($CH_2$); 71.3, 73.7, 75.8, 99.0 (CH). HRMS: m/z=1077.8487 $[M+H]^+$ (calculated for $C_{59}H_{117}N_2O_{14}$: 1077.8505).

5.13. Synthesis of α-GalCer Analogue 43 (IPB002034

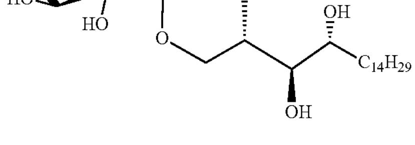

1 (150 mg, 0.15 mmol), paraformaldehyde (4.4 mg, 0.15 mmol), cerotic acid (58 mg, 0.15 mmol) and isocyanide 10

(31.9 mg, 0.15 mmol) in MeOH/THF (6 mL) reacted following the general procedure for the synthesis of α-GalCer analogues by Ugi-4CR (section 1). Column chromatography (n-hexane/EtOAc 2:1) afforded the protected Ugi product 42 (126 mg, 52%). $R_f$=0.20 (n-hexane/EtOAc 2:1) that was further deprotected following the general procedure for the benzyl ether protecting group removal (section 2) to afford the α-GalCer analogue 43 (71.7 mg, 85%) as a colorless oil. $[\alpha]_D^{23.4}$=25.1 (c 1.0 $CHCl_3$). $^1H$ NMR (400 MHz, DMSO-$d_6$): δ=0.83 (t, 6H, J=6.7 Hz, 2×$CH_3$); 0.96-1.35 (m, 63H); 1.36-1.56 (m, 7H), 2.09-2.43 (m, 4H); 3.14-4.31 (m); 4.56-4.66 (m, 2H); 5.27-5.38 (m, 2H); 7.55 (bs, 1H, NH); $^{13}C$ NMR* (100 MHz, DMSO-$d_6$) δ=13.7 ($CH_3$); 22.0, 23.1, 24.5, 25.0, 27.3, 29.0, 30.1, 31.3, 32.6, 33.0, 34.8, 38.4, 46.2 ($CH_2$); 57.0 (CH); 58.0 ($CH_3$); 60.2, 60.7, 64.2, 65.6, 66.9, 68.2 ($CH_2$); 68.2, 68.5 (CH); 68.8, 69.6, 71.2 ($CH_2$); 71.2, 73.6, 75.7, 98.9 (CH). HRMS: m/z=1105.8961 $[M+H]^+$ (calculated for $C_{61}H_{121}N_2O_{14}$: 1105.8818).

5.14. Synthesis of α-GalCer Analogue 45 (IPB002044

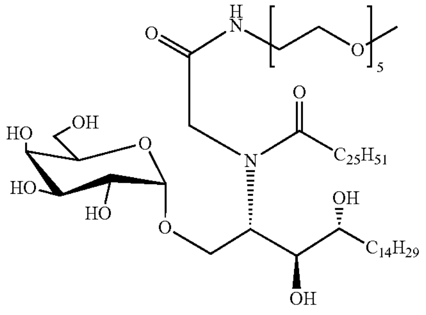

1 (150 mg, 0.15 mmol), paraformaldehyde (4.4 mg, 0.15 mmol), cerotic acid (58 mg, 0.15 mmol) and isocyanide 11 (38.4 mg, 0.15 mmol) in MeOH/THF (6 mL) reacted following the general procedure for the synthesis of α-GalCer analogues by Ugi-4CR (section 1). Column chromatography (n-hexane/EtOAc 1:1) afforded the protected Ugi product 44 (110 mg, 44%). $R_f$=0.17 (n-hexane/EtOAc 2:1) that was further deprotected following the general procedure for the benzyl ether protecting group removal (section 2) to afford the α-GalCer analogue 45 (52.9 mg, 71%) as a colorless oil. $[\alpha]_D^{23.4}$=25.8 (c 1.0 $CHCl_3$). $^1H$ NMR (400 MHz, DMSO-$d_6$): δ=0.83 (t, 6H, J=6.6 Hz, 2×$CH_3$); 1.12-1.34 (m, 58H); 1.35-1.66 (m, 14H), 2.10-2.18 (m, 2H); 2.39-2.46 (m, 2H); 3.18-4.29 (m); 4.56-4.66 (m, 2H), 7.55 (t, 1H, J=6.0 Hz, NH); $^{13}C$ NMR* (100 MHz, DMSO-$d_6$) δ=13.8 ($CH_3$); 22.0, 21.6, 23.2, 24.5, 25.0, 27.3, 29.0, 31.4, 32.4, 33.0, 35.7, 38.3, 40.1, 46.2, 57.0 ($CH_2$); 57.0 (CH); 57.9 ($CH_2$); 57.9 ($CH_3$); 60.2, 60.7, 64.3, 65.6, 66.9 ($CH_2$); 68.1 (CH); 68.2 ($CH_2$); 68.6 (CH); 68.8, 69.7, 71.2 ($CH_2$); 71.3, 73.5, 75.7, 99.1 (CH). HRMS: m/z=1149.9048 $[M+H]^+$ (calculated for $C_{63}H_{125}N_2O_{15}$: 1149.9080).

5.15. Synthesis of α-GalCer Analogue 47 (IPB002035

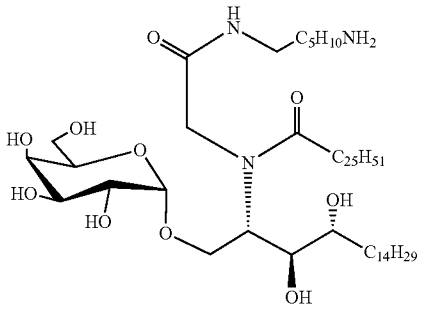

1 (150 mg, 0.15 mmol), paraformaldehyde (4.4 mg, 0.15 mmol), cerotic acid (58 mg, 0.15 mmol) and isocyanide 9 (22 mg, 0.15 mmol) in MeOH/THF (6 mL) reacted following the general procedure for the synthesis of α-GalCer analogues by Ugi-4CR (section 1). Column chromatography (n-hexane/EtOAc 6:1) afforded the protected Ugi product 46 (119 mg, 51%), $R_f$=0.28 (n-hexane/EtOAc 6:1) that was further deprotected following the general procedure for the benzyl ether/azide protecting groups removal (section 2) to afford the α-GalCer analogue 47 (59 mg, 78%) as a colorless oil $[\alpha]_D^{23.4}$=28.1 (c 1.0 $CHCl_3$). $^1H$ NMR (400 MHz, DMSO-$d_6$): δ=0.83 (t, 6H, J=5.9 Hz, 2×$CH_3$); 0.95-1.85 (m, 80H); 2.10-2.20 (m, 3H); 2.31-2.38 (m, 2H); 2.42 (t, 2H, J=8.1 Hz, $CH_2$); 2.95-4.71 (m); 7.46-7.54 (m, 1H). $^{13}C$ NMR* (100 MHz, DMSO-$d_6$): δ=13.7 ($CH_3$); 21.9, 25.7, 29.0, 31.3, 34.0, 38.4, 46.2 ($CH_2$), 57.0 (CH); 60.0, 63.1 ($CH_2$); 68.0, 68.5, 71.2, 99.0 (CH). HRMS: m/z=1014.8637 $[M+H]^+$ (calculated for $C_{58}H_{116}N_3O_{10}$: 1014.8661).

5.16. Synthesis of α-GalCer Analogues 49 and 50 (IPB001910 and IPB000964

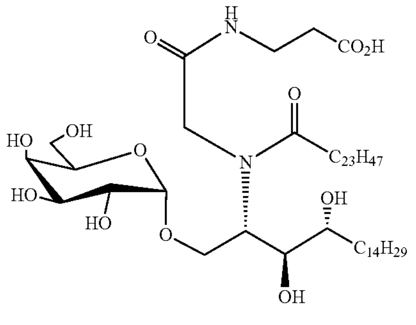

1 (800 mg, 0.785 mmol), paraformaldehyde (23.6 mg, 0.785 mmol), lignoceric acid (289 mg, 0.785 mmol) and isocyanide 14 (122 mg, 0.785 mmol) in MeOH/THF (9 mL) reacted following the general procedure for the synthesis of α-GalCer analogues by Ugi-4CR (section 1). Column chromatography (n-hexane/EtOAc 10:1-5:1) afforded the protected Ugi product 48 (428 mg, 42%). $R_f$=0.47 (n-hexane/EtOAc 5:1) that was further deprotected following the general procedure for the benzyl ether protecting group removal (section 2) to afford α-GalCer analogue 49. In order to remove the tert-butyl group, the product was dissolved in a solution containing 25% TFA in DCM (3 mL) and the reaction mixture was stirred for 3 h. Then, the solvent was evaporated under reduced pressure and the remaining TFA co-evaporated with DCM to afford the final deprotected α-GalCer analogue 50 (167 mg, 63% over two steps) as a colorless oil. [Ca]°=28.8 (c 1.0 $CHCl_3$). $^1$H NMR (400 MHz, $CDCl_3$): δ=0.88 (t, 6H, J=6.6 Hz, 2×$CH_3$); 1.02-1.70 (m); 2.04-2.79 (m); 2.93-4.53 (m). ESI-MS: m/z=959.8 $[M+H]^+$ (calculated for $C_{53}H_{103}N_2O_{12}$: 959.8); 997.7 $[M+K]^+$ (calculated for $C_{53}H_{102}KN_2O_{12}$: 997.7). HRMS: m/z=995.7487 $[M(OMe)+Na]^+$ (calculated for $C_{54}H_{104}N_2NaO_{12}$: 995.7466).

5.17. Synthesis of α-GalCer Analogue 52 (IPB001909

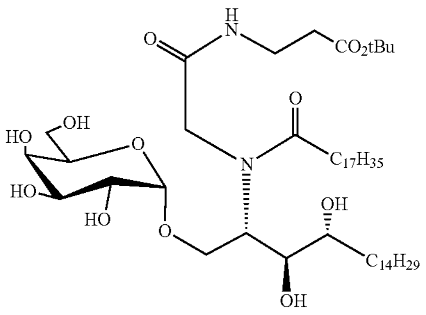

1 (100 mg, 0.098 mmol), paraformaldehyde (2.9 mg, 0.098 mmol), stearic acid (28 mg, 0.098 mmol) and isocyanide 14 (15 mg, 0.098 mmol) in MeOH/THF (6 mL) reacted following the general procedure for the synthesis of α-GalCer analogues by Ugi-4CR (section 1). Column chromatography (n-hexane/EtOAc 8:1-1:1) afforded the protected Ugi product 51 (51 mg, 35%). $R_f$=0.73 (n-hexane/EtOAc 1:1) that was further deprotected following the general procedure for the benzyl ether protecting group removal (section 2). to afford the final deprotected α-GalCer analogue 52 (32 mg, 99%) as a colorless oil. $[\alpha]_D^{24.0}$=17.9 (c 1.0 $CHCl_3$). $^1$H NMR (400 MHz, $CD_3OD$): δ=0.89 (t, 6H, J=6.9 Hz, 2×$CH_3$); 1.24-1.38 (m, 54H); 1.43-1.48 (m, 9H, 3×$CH_3$ (tBu)); 2.23-2.30 (m, 2H); 2.43-2.50 (m, 2H); 3.22-4.38 (m). $^{13}$C NMR (100 MHz, $CDCl_3$): δ=14.2 ($CH_3$); 18.2, 22.8, 24.9 ($CH_2$); 28.2 ($CH_3$); 29.2, 29.4, 29.5, 29.6, 29.7, 29.8, 29.9, 32.0, 34.0 ($CH_2$); 53.5 (CH); 58.5 ($CH_2$); 77.4 (CH); 81.6 (C); 163.9, 175.6, 178.2 (C═O); HRMS: m/z=953.8387 $[M+Na]^+$ (calculated for $C_{51}H_{98}N_2NaO_{12}$: 953.7017).

5.18. Synthesis of α-GalCer Analogue 54 (IPB002043

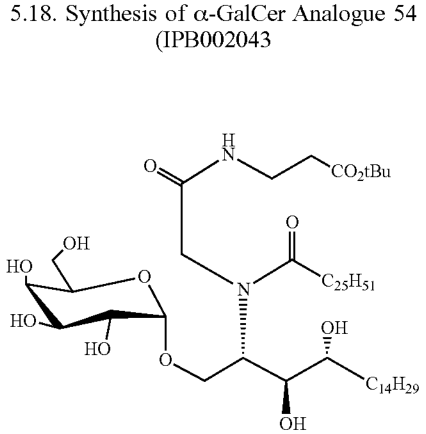

1 (225 mg, 0.22 mmol), paraformaldehyde (4.4 mg, 0.15 mmol), cerotic acid (58 mg, 0.098 mmol) and isocyanide 14 (23 mg, 0.15 mmol) in MeOH/THF (6 mL) reacted following the general procedure for the synthesis of α-GalCer analogues by Ugi-4CR (section 1). Column chromatography (n-hexane/EtOAc 6:1) afforded the protected Ugi product 53 (190 mg, 54%). $R_f$=0.28 (n-hexane/EtOAc 6:1) that was further deprotected following the general procedure for the benzyl ether protecting group removal (section 2). to afford the final deprotected α-GalCer analogue 54 (125 mg, 99%) as a colorless oil. $[\alpha]_D^{24.0}$=32.2 (c 1.0 $CHCl_3$). $^1$H NMR (400 MHz, DMSO-$d_6$): δ=0.84 (t, 6H, J=7.2 Hz, 2×$CH_3$); 1.04-1.35 (m, 67H); 1.36-1.42 (m, 9H, 3×$CH_3$ (tBu)); 1.42-1.56 (m, 5H); 2.25-2.42 (m, 4H); 3.15-4.93 (m); 7.52 (t, 1H, J=6.0 Hz, NH). $^{13}$C NMR (100 MHz, DMSO-$d_6$): δ=13.8 ($CH_3$); 22.2, 24.6 ($CH_2$); 27.7 ($CH_3$); 28.9, 29.2, 31.4, 32.5, 34.6, 35.0 ($CH_2$); 54.9 (CH); 60.3, 64.1 ($CH_2$); 68.2, 68.6, 69.7, 71.3, 75.7 (CH); 79.7 (C); 98.9 (CH); 166.1, 169.9, 170.6 (C═O); HRMS: m/z=1043.8430 $[M+H]^+$ (calculated for $C_{59}H_{115}N_2O_{12}$: 1043.8450).

5.19. Synthesis of α-GalCer Analogue 56 (IPB001911

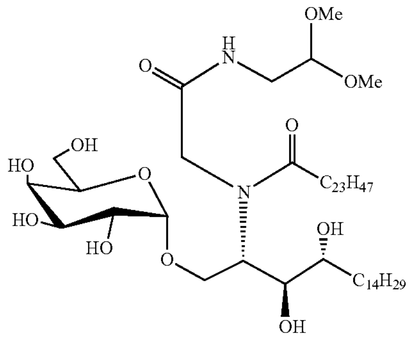

1 (400 mg, 0.392 mmol), paraformaldehyde (11.8 mg, 0.392 mmol), lignoceric acid (144.5 mg, 0.392 mmol) and isocyanide 13 (45.1 mg, 0.392 mmol) in MeOH/THF (6 mL) reacted following the general procedure for the synthesis of α-GalCer analogues by Ugi-4CR (section 1). Column chromatography (n-hexane/EtOAc 10:1-5:1) afforded the protected Ugi product 55 (200 mg, 34%). $R_f$=0.16 (n-hexane/EtOAc 4:1) that was further deprotected following the general procedure for the benzyl ether protecting group removal (section 1) to afford the α-GalCer analogue 56 (114 mg, 89%) as a colorless oil. $[\alpha]_D^{24.1}$=28.1 (c 1.0 $CHCl_3$). $^1$H NMR (400 MHz, $CDCl_3$): δ=0.88 (t, 6H, J=7.0 Hz, 2×$CH_3$); 1.11-1.42 (m, 66H); 1.52-1.70 (m, 4H); 2.17 (s, 1H); 2.19-2.22 (m, 2H); 2.34 (t, 1H; J=7.6 Hz); 3.33-3.41 (2×s, 6H; 2×$OCH_3$); 3.47-4.44 (m); 8.27 (s, 1H; NH). $^{13}$C NMR (100 MHz, $CDCl_3$): δ=14.3 ($CH_3$); 22.9, 29.5, 29.6, 29.8, 29.9, 30.0, 32.1 ($CH_2$), 79.8 (CH). HRMS: m/z=997.7627 $[M+Na]^+$ (calculated for $C_{54}H_{106}N_2NaO_{12}$: 997.7643).

5.20. Synthesis of α-GalCer Analogue 58 (IPB002038)

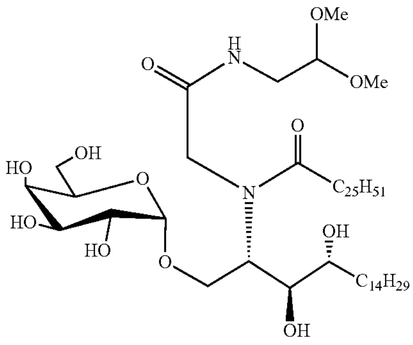

1 (150 mg, 0.15 mmol), paraformaldehyde (4.4 mg, 0.15 mmol), cerotic acid (58.3 mg, 0.15 mmol) and isocyanide 13 (17 mg, 0.15 mmol) in MeOH/THF (6 mL) reacted following the general procedure for the synthesis of α-GalCer analogues by Ugi-4CR (section 1). Column chromatography (n-hexane/EtOAc 6:1) afforded the protected Ugi product 57 (125 mg, 55%). $R_f$=0.25 (n-hexane/EtOAc 6:1) that was further deprotected following the general procedure for the benzyl ether protecting group removal (section 1) to afford the α-GalCer analogue 58 (81 mg, 99%) as a colorless oil. $[\alpha]_D^{24.1}$=32.6 (c 1.0 $CHCl_3$). $^1H$ NMR (400 MHz, DMSO-$d_6$/$CDCl_3$ 6.5:1 (v:v)) δ=0.85 (t, 6H, J=6.7 Hz, 2×$CH_3$); 1.15-1.31 (m, 69H), 1.34-1.59 (m, 7H), 2.10-2.16 (m, 1H); 2.31-2.33 (m, 1H); 2.35 (t, 1H; J=7.3 Hz); 3.15 (t, 2H, J=5.8 Hz); 3.22-3.27 (2×s, 6H; 2×$OCH_3$); 3.38-4.79 (m); 8.24 (s, 1H; NH). $^{13}C$ NMR* (100 MHz, DMSO-$d_6$/$CDCl_3$ 6.5:1 (v:v)) δ=12.8 ($CH_3$); 21.8, 24.4, 24.6, 28.8, 31.0, 32.3, 32.4, 39.9, 40.3 ($CH_2$), 52.9 ($CH_3$); 56.7, 68.0, 68.5, 69.6, 70.9, 71.1, 98.8 (CH); 170.3 (C═O). HRMS: m/z=1003.8111 [M+H]+(calculated for $C_{56}H_{111}N_2O_{12}$: 1003.8137).

5.21. Synthesis of α-GalCer Analogue 60 (IPB000970)

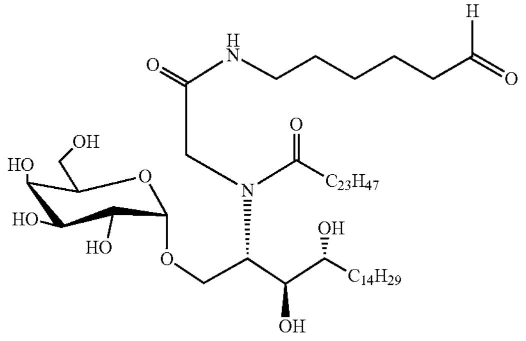

1 (400 mg, 0.392 mmol), paraformaldehyde (11.8 mg, 0.392 mmol), lignoceric acid (144.5 mg, 0.392 mmol) and isocyanide 15 (96.2 mg, 0.392 mmol) in MeOH/THF (6 mL) reacted following the general procedure for the synthesis of α-GalCer analogues by Ugi-4CR (section 1). Column chromatography (n-hexane/EtOAc 10:1-5:1) afforded the protected Ugi product 59 (469 mg, 72%). $R_f$=0.74 (n-hexane/EtOAc 2:1) that was further deprotected following the general procedure for the benzyl ether/4-phenyl-1,3-dioxolane protecting groups removal (section 2) to afford the α-GalCer analogue 60 (160 mg, 57%) as a colorless oil. $[\alpha]_D^{24.0}$=30.6 (c 1.0 $CHCl_3$). $^1H$ NMR (400 MHz, $CDCl_3$): δ=0.78-0.95 (m, 7H); 0.88 (t, 6H, J=6.7 Hz, 2×$CH_3$); 0.96-1.74 (m, 73H); 2.12-2.50 (m, 4H); 3.10-4.44 (m); 4.89 (s, 1H); 8.09 (s, 1H); 9.73 (s, 1H; CHO); $^{13}C$ NMR (100 MHz, $CDCl_3$): δ=14.3 ($CH_3$); 22.8, 25.3, 26.4, 29.9, 32.1, 34.0, 43.8 ($CH_2$); 69.0, 70.2, 110.2 (CH); 202.9 (CHO). ESI-MS: m/z=986.0 $[M+H]^+$ (calculated for $C_{56}H_{109}N_2O_{11}$: 985.8). HRMS: m/z=1053.8332 [M(dimethyl acetal)+Na]+ (calculated for $C_{58}H_{114}N_2NaO_{12}$: 1053.8269).

5.22. Synthesis of α-GalCer Analogue 62 (IPB002041)

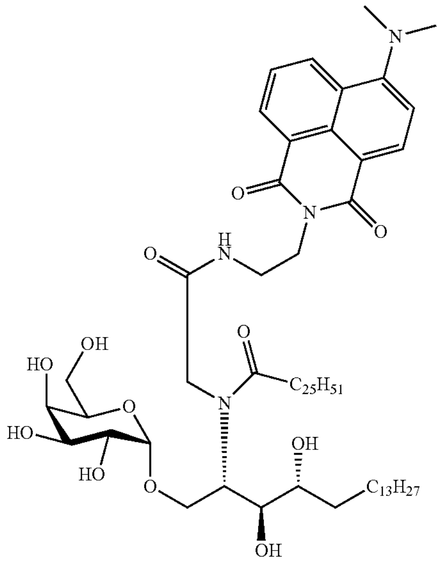

1 (150 mg, 0.15 mmol), paraformaldehyde (4.4 mg, 0.15 mmol), cerotic acid (58 mg, 0.392 mmol) and isocyanide 16 (41 mg, 0.15 mmol) in MeOH/THF (6 mL) reacted following the general procedure for the synthesis of α-GalCer analogues by Ugi-4CR (section 1). Column chromatography (n-hexane/EtOAc 10:1-5:1) afforded the protected Ugi product 61 (129 mg, 82%). $R_f$=0.74 (n-hexane/EtOAc 2:1) that was further deprotected following the general procedure for the benzyl ether/4-phenyl-1,3-dioxolane protecting groups removal (section 2) to afford the α-GalCer analogue 62 (72 mg, 82%) as a colorless oil. $[\alpha]_D^{24.0}$=26.8 (c 1.0 $CHCl_3$). $^1H$ NMR (400 MHz, DMSO-$d_6$): δ=0.77-0.85 (m, 6H); 1.01-1.51 (m, 72H); 2.40-2.45 (m, 2H); 3.03 (s, 3H, $CH_3$); 3.06 (s, 3H, $CH_3$); 3.09-4.86 (m); 7.07-7.33 (m, 3H, Ar); 8.17-8.49 (m, 2H, Ar). HRMS: m/z=1181.8628 $[M+H]^+$ (calculated for $C_{68}H_{117}N_4O_{12}$: 1181.8668).

5.23. Synthesis of α-GalCer Analogue 64 (IPB001912

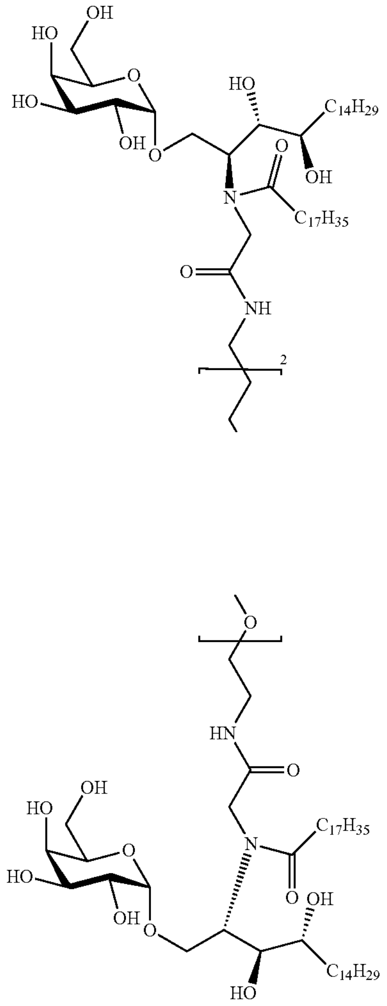

1 (100 mg, 0.098 mmol), paraformaldehyde (2.9 mg, 0.098 mmol), stearic acid (27.9 mg, 0.098 mmol) and isocyanide 12 (8.2 mg, 0.049 mmol) in MeOH/THF (3 mL) reacted following the general procedure for the synthesis of α-GalCer analogues by Ugi-4CR (section 1). Column chromatography (n-hexane/EtOAc 6:1) afforded the protected Ugi product 63 (15.1 mg, 5%). $R_f$=0.44 (n-hexane/EtOAc 5:1) that was further deprotected following the general procedure for the benzyl ether protecting group removal (section 2) to afford the α-GalCer analogue 64 (9.0 mg, 98%) as a colorless oil. $[\alpha]_D^{24.8}$=26.8 (c 1.0 $CHCl_3$). $^1H$ NMR (400 MHz, $CDCl_3$): δ=0.77-0.94 (m, 14H); 0.88 (t, 12H, J=6.7 Hz, 4×$CH_3$); 1.07-1.46 (m, 102H); 1.55-1.70 (m, 8H); 2.20-2.30 (m, 4H); 2.35 (t, 5H, J=7.5 Hz); 2.50 (t, 3H, J=8.2 Hz); 3.58-5.24 (m), 4.35 (t, J=7.0 Hz); 8.00-8.18 (m, 2H; 2×NH); $^{13}C$ NMR (100 MHz, $CDCl_3$): δ=14.3 ($CH_3$); 22.3, 22.8, 24.8, 25.1, 28.0, 29.2, 29.3, 29.4, 29.5, 29.6, 29.7, 29.8, 32.1, 34.0, 51.6, 68.7 ($CH_2$); 77.4, 110.0 (CH); 179.0 (C═O).

5.24. Synthesis of α-GalCer Analogue 66 (IPB001915

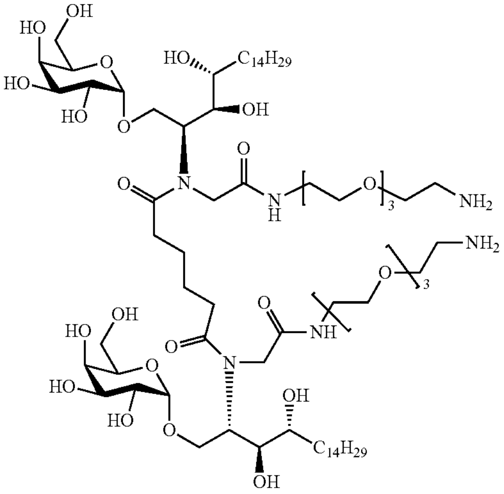

1 (100 mg, 0.098 mmol), paraformaldehyde (2.9 mg, 0.098 mmol), adipic acid (7.2 mg, 0.049 mmol) and isocyanide 8 (22.4 mg, 0.098 mmol) in MeOH/THF (3 mL) reacted following the general procedure for the synthesis of α-GalCer analogues by Ugi-4CR (section 1). Column chromatography (n-hexane/EtOAc 2:1-1:2) afforded the protected Ugi product 65 (59.1 mg, 45%). $R_f$=0.21 (n-hexane/EtOAc 1:1) that was further deprotected following the general procedure for the benzyl ether/azide protecting groups removal (section 2) to afford the α-GalCer analogue 66 (18.3 mg, 54%) as a colorless oil. $[\alpha]_D^{24.7}$=14.3 (c 1.0 $CHCl_3$). $^1H$ NMR (400 MHz, $DMSOd_6$): δ=0.85 (t, 6H, J=6.7 Hz, 2×$CH_3$); 1.04 (d, 2H, J=6.2 Hz); 1.05-1.29 (m, 48H); 1.36-1.59 (m, 11H); 2.07-2.22 (m, 4H); 2.36-2.45 (m, 2H); 2.89-3.00 (m, 4H); 3.17-4.68 (m); 8.26 (s, 2H, 2×NH). $^{13}C$ NMR (100 MHz, $DMSOd_6$): δ=13.9 ($CH_3$); 22.1, 28.7, 29.1, 29.2, 29.4, 31.3, 38.5, 45.5 ($CH_2$); 57.1 (CH); 58.0, 60.6, 66.6 ($CH_2$); 68.3, 68.9 (CH); 69.6, 69.7, 69.8, 60.9 ($CH_2$), 71.3, 107.0 (CH). HRMS: m/z=767.5122 $[M+2H]^{2+}$ (calculated for $C_{74}H_{144}N_6O_{26}/2$: 767.5144).

5.25. Synthesis of α-GalCer Analogue 68 (IPB001917

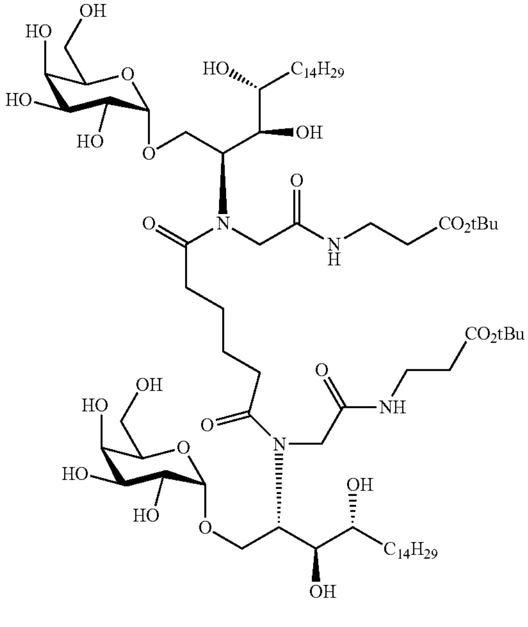

1 (100 mg, 0.098 mmol), paraformaldehyde (2.9 mg, 0.098 mmol), adipic acid (7.2 mg, 0.049 mmol) and isocyanide 14 (15.2 mg, 0.098 mmol) in MeOH/THF (3 mL) reacted following the general procedure for the synthesis of α-GalCer analogues by Ugi-4CR (section 1). Column chromatography (n-hexane/EtOAc 3:1-2:1) afforded the protected Ugi product 67 (23.1 mg, 9%). $R_f$=0.77 (n-hexane/EtOAc 2:1) that was further deprotected following the general procedure for the benzyl ether protecting group removal (section 2) to afford the α-GalCer analogue 68 (13 mg, 99%) as a colorless oil. $[\alpha]_D^{24.6}$=36.7 (c 1.0 $CHCl_3$). $^1H$ NMR (400 MHz, $CDCl_3$): δ=0.87 (t, 6H, J=6.8 Hz, 2×$CH_3$); 1.14-1.36 (m, 24×$CH_2$; 6×$CH_3$); 1.35-1.50 (m); 1.74-2.10 (m); 2.21-2.53 (m); 3.36-4.71 (m); 8.07 (s, 2H, NH). $^{13}C$ NMR (100 MHz, $CDCl_3$): δ=14.3 ($CH_3$); 22.8, 24.0 ($CH_2$); 28.2 ($CH_3$); 29.3, 29.5, 29.8, 32.1 ($CH_2$); 53.9 (CH); 67.6, 67.8, 67.9, 68.7 ($CH_2$), 77.4 (CH); 82.6 (C); 106.5, 107.8 (CH); 171.0, 172.1 (C═O). HRMS: m/z=1439.9477 $[M+H]^+$ (calculated for $C_{72}H_{135}N_4O_{24}$: 1439.9466).

5.26. Synthesis of GalCer Analogue 70 (IPB002611

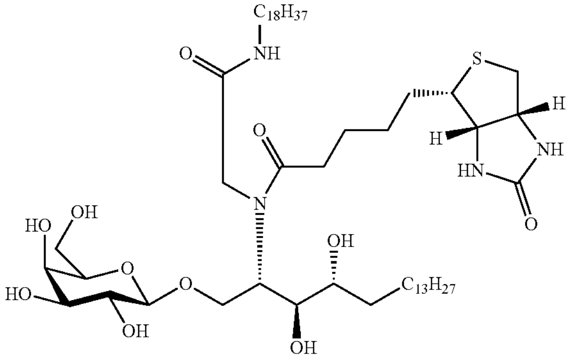

2 (120 mg, 0.100 mmol), paraformaldehyde (3.0 mg, 0.100 mmol), biotin (24.4 mg, 0.100 mmol) and isocyanide 6 (27.9 mg, 0.100 mmol) in MeOH/DCM (3 mL) reacted following the general procedure for the synthesis of GalCer analogues by Ugi-4CR (section 1). Column chromatography (DCM/MeOH 80:1-20:1) afforded the protected Ugi product 69 (54 mg, 31%). $R_f$=0.35 (DCM/MeOH 20:1) that was further deprotected following the general procedure for the p-methoxybenzyl ether protecting group removal (section 3) to afford the GalCer analogue 70 (31 mg, 99%) as a light-yellow oil. $^1H$ NMR (400 MHz, $CDCl_3$): δ=0.88 (t, 6H, J=6.7 Hz, 2×$CH_3$); 0.94-2.00 (m); 3.32-5.00 (m). $^{13}C$ NMR (100 MHz, $CDCl_3$): δ=14.3 ($CH_3$); 22.8, 27.2, 29.5, 29.8, 29.9, 32.1, 35.0, 37.2, 46.6 ($CH_2$); 55.4, 55.6 (CH); 70.9 ($CH_2$); 110.6 (CH). HRMS: m/z=1015.7391 $[M+H]^+$ (calculated for $C_{54}H_{103}N_4O_{11}S$: 1015.7344).

5.27. Synthesis of GalCer Analogue 72 (IPB002613

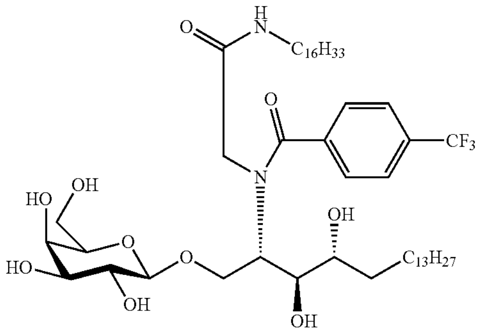

2 (120 mg, 0.100 mmol), paraformaldehyde (3.0 mg, 0.100 mmol), 4-(trifluoromethyl) benzoic acid (19.0 mg, 0.100 mmol) and isocyanide 5 (25.1 mg, 0.100 mmol) in MeOH/DCM (3 mL) reacted following the general procedure for the synthesis of GalCer analogues by Ugi-4CR (section 1). Column chromatography (n-hexane/EtOAc 4:1-2:1) afforded the protected Ugi product 71 (20 mg, 12%). $R_f$=0.25 (n-hexane/EtOAc 2:1) that was further deprotected following the general procedure for the p-methoxybenzyl ether protecting group removal (section 3) to afford the GalCer analogue 72 (11 mg, 99%) as a light-yellow oil. $^1H$ NMR (400 MHz, $CDCl_3$): δ=0.88 (bs, 6H, 2×$CH_3$); 1.02-1.48 (m); 3.46-5.20 (m), 7.00-7.60 (m, Ar). $^{13}C$ NMR (100 MHz, $CDCl_3$): δ=14.2, 14.3 ($CH_3$); 22.8, 27.2, 29.5, 29.8, 30.0, 32.0, 32.1, 37.2 ($CH_2$); 55.4, 55.6, 113.7, 128.7, 128.8 (CH). HRMS: m/z=933.6357 $[M+H]^+$ (calculated for $C_{50}H_{88}F_3N_2O_{10}$: 933.6391).

5.28. Synthesis of GalCer Analogue 74 (IPB002614

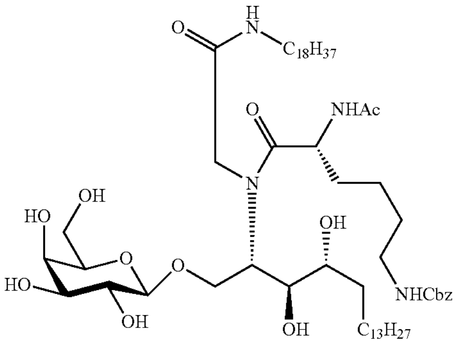

2 (120 mg, 0.100 mmol), paraformaldehyde (3.0 mg, 0.100 mmol), Ac-L-Lys(Z)—OH (32.2 mg, 0.100 mmol) and isocyanide 6 (27.9 mg, 0.100 mmol) in MeOH/DCM (3 mL) reacted following the the general procedure for the synthesis of GalCer analogues by Ugi-4CR (section 1). Column chromatography (DCM/MeOH 99:1) afforded the protected Ugi product 73 (20 mg, 11%). $R_f$=0.30 (DCM/MeOH 20:1) that was further deprotected following the general procedure for the p-methoxybenzyl ether protecting group removal (section 3) to afford the GalCer analogue 74 (12 mg, 99%) as a light-yellow oil. $^1H$ NMR (400 MHz, $CDCl_3$): δ=0.88 (t, 6H, J=6.4 Hz, 2×$CH_3$); 0.94-1.65 (m); 2.93-5.52 (m), 7.15-7.61 (m, Ar). $^{13}C$ NMR (100 MHz, $CDCl_3$): δ=14.2, 14.3 ($CH_3$); 22.8, 29.5, 29.8, 30.1, 32.0, 32.1 ($CH_2$). HRMS: m/z=1093.7944 $[M+H]^+$ (calculated for $C_{60}H_{109}N_4O_{13}$: 1093.7991).

5.29. Synthesis of GalCer Analogue 76 (IPB002615

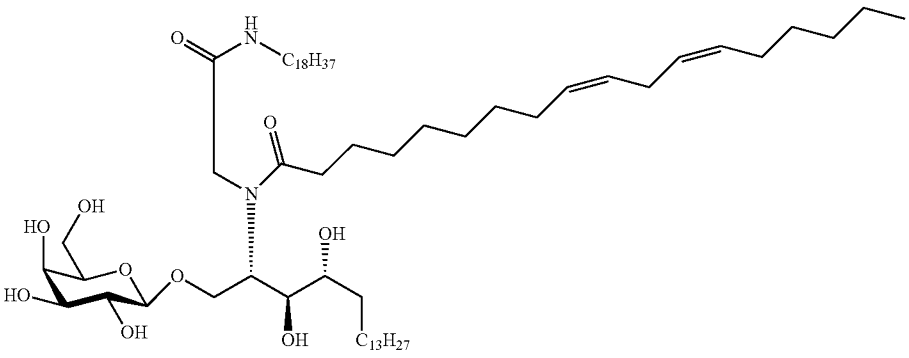

2 (120 mg, 0.100 mmol), paraformaldehyde (3.0 mg, 0.100 mmol), linoleic acid (31.0 mL, 0.100 mmol) and isocyanide 10 (21.7 mg, 0.100 mmol) in MeOH/DCM (3 mL) reacted following the general procedure for the synthesis of GalCer analogues by Ugi-4CR (section 1). Column chromatography (DCM/EtOAc 5:1-1:2) afforded the protected Ugi product 75 (70 mg, 41%). $R_f$=0.28 (DCM/EtOAc 1:1) that was further deprotected following the general procedure for the p-methoxybenzyl ether protecting group removal (section 3) to afford the GalCer analogue 76 (40 mg, 99%) as a light-yellow oil. $^1H$ NMR (400 MHz, $CDCl_3$): δ=0.85-0.90 (m, 6H, 2×$CH_3$); 1.15-1.44 (m); 1.46-1.68 (m), 1.74-1.90 (m); 1.99-2.08 (m); 2.71-2.78 (m); 3.31-4.50 (m); 5.27-5.41 (m). $^{13}C$ NMR (100 MHz, $CDCl_3$): δ=14.2 ($CH_3$); 22.7, 22.8, 25.7, 27.3, 29.4, 29.5, 29.8, 29.9, 31.6, 32.0, 37.9, 46.6 ($CH_2$); 55.3, 55.6 (CH); 59.1 ($CH_3$), 59.3, 64.9 (CH); 67.4, 69.7, 70.2, 70.4, 70.6, 70.7, 72.0 ($CH_2$); 72.9, 82.7, 110.5, 113.8, 128.0, 128.2, 130.1, 130.3 (CH); 165.6, 173.4 (C═O). HRMS: m/z=989.7216 $[M+H]^+$ (calculated for $C_{53}H_{101}N_2O_{14}$: 989.7253).

5.30. Synthesis of GalCer Analogue 78 (IPB002612

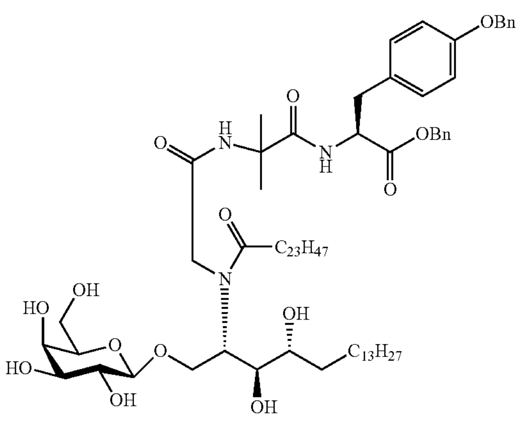

2 (120 mg, 0.100 mmol), paraformaldehyde (3.0 mg, 0.100 mmol), lignoceric acid (36.9 mg, 0.100 mmol) and isocyanide 17 (45.6 mg, 0.100 mmol) in MeOH/DCM (3 mL) reacted following the general procedure for the synthesis of GalCer analogues by Ugi-4CR (section 1). Column chromatography (n-hexane/EtOAc 5:1-2:1) afforded the protected Ugi product 77 (30 mg, 15%). $R_f$=0.30 (n-hexane/EtOAc 2:1) that was further deprotected following the general procedure for the p-methoxybenzyl ether protecting group removal (section 3) to afford the GalCer analogue 78 (19 mg, 99%) as a light-yellow oil. $^1H$ NMR (400 MHz, $CDCl_3$): δ=0.88 (t, 6H, J=7.2 Hz, 2×$CH_3$); 1.05-1.60 (m); 3.34-5.33 (m); 6.71-7.14 (m, Ar); 7.19-7.54 (m, Ar). $^{13}C$ NMR (100 MHz, $CDCl_3$): δ=14.3 ($CH_3$); 22.8 ($CH_2$); 24.9 ($CH_3$); 29.5, 29.9, 32.1, 33.2, 46.4 ($CH_2$); 55.3, 55.5 (CH); 67.8, 70.1 ($CH_2$); 114.3, 115.0, 127.6, 128.7, 130.2, 130.3 (CH); 135.3, 136.8 (C); 168.6, 176.5 (C═O). ESI-MS: m/z=1317.3 $[M+H]^+$ (calculated for $C_{77}H_{126}N_3O_{14}$: 1316.9).

(1) Brouard, I.; Rivera, D. G. Multicomponent Synthesis of Ugi-Type Ceramide Analogues and Neoglycolipids from Lipidic Isocyanides. 2012. https://doi.org/10.1021/jo300462m.

(2) Trappeniers, M.; Goormans, S.; Van Beneden, K.; Decruy, T.; Linclau, B.; Al-Shamkhani, A.; Elliott, T.; Ottensmeier, C.; Werner, J. M.; Elewaut, D.; et al. Synthesis and in Vitro Evaluation of α-GalCer Epimers. *ChemMedChem* 2008, 3, 1061-1070. https://doi.org/10.1002/cmdc.200800021.

(3) Rotstein, B. H.; Mourtada, R.; Kelley, S. O.; Yudin, A. K. Solvatochromic Reagents for Multicomponent Reactions and Their Utility in the Development of Cell-Permeable Macrocyclic Peptide Vectors. 2011, No. Scheme 2, 12257-12261. https://doi.org/10.1002/chem.201102096.

The invention claimed is:

1. A compound according to formula (I):

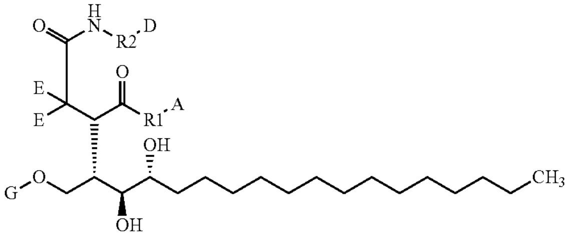

wherein

R1 is a linear or branched alkyl, alkenyl, or alkoxy group, wherein R1 is optionally substituted with —halogen, —OH, —$NH_2$, —NHR10, —$N_3$, —C═O; acetal, —$CO_2H$, —$CO_2R11$, —$SO_3H$, —$SO_3R11$, —SH; —SR12, maleimide, —$OPO_3R13$, or wherein R1 is absent, wherein R10, R11 and R12 are, independently, a linear or branched alkyl or alkenyl group, cycloalkyl or an aromatic or heteroaromatic group, or protecting groups, and R13 is H or a linear or branched alkyl or alkenyl group;

A is H, cycloalkyl, an aromatic for heteroaromatic) group, a linear or branched alkyl, alkenyl, or alkoxy, wherein A is optionally substituted with: —OH, —$NH_2$, —NHR10, —$N_3$, —C═O; acetal, —$CO_2H$, —$CO_2R11$, —$SO_3H$, $SO_3R11$, —SH; —SR12, maleimide, —$OPO_3R13$, wherein preferably R1 is absent when A is a cycloalkyl group, or wherein A is an amino acid or a polypeptide;

R2 is a linear or branched alkyl, alkenyl, or alkoxy group, wherein R2 is optionally substituted with —halogen, —OH, —$NH_2$, —NHR10, —$N_3$, —C═O; acetal, —$CO_2H$, —$CO_2R11$, —$SO_3H$, —$SO_3R11$, —SH; —SR12, maleimide, —$OPO_3R13$, or wherein R2 is absent, D is H, cycloalkyl, an aromatic or heteroaromatic group, a linear or branched alkyl, alkenyl, or alkoxy, wherein D is optionally substituted with: —OH, —$NH_2$, —NHR10, —$N_3$, —C═O; ═O, $NR10_2$, acetal, —$CO_2H$, —$CO_2R11$, —$SO_3H$, $SO_3R11$, —SH; —SR12, maleimide, —$OPO_3R13$, or wherein D is an amino acid or a polypeptide;

E is, independently, —H, alkyl, —halogen, —OH, —$NH_2$, —NHR10, —$N_3$, —C═O; acetal, —$CO_2H$, —$CO_2R11$, —$SO_3H$, —$SO_3R11$, —SH; —SR12, maleimide, or —$OPO_3R13$;

G is a saccharide, wherein the saccharide is optionally substituted with —halogen, —OH, —$NH_2$, —NHR10, —$N_3$, —C═O; acetal, —$CO_2H$, —$CO_2R11$, —$SO_3H$, —$SO_3R11$, —SH; —SR12, maleimide, —$OPO_3R13$, alkyl, or ester—, alkyl— or amide-aromatic or heteroaromatic substituents;

wherein optionally two compounds according to formula (I) are covalently bonded to each other at their respective R2 groups, thereby forming R15, wherein R15 is a linear or branched alkyl, alkenyl or alkoxy group, and wherein D is absent, or wherein optionally two compounds according to formula (I) are covalently bonded to each other at their respective R1 groups, thereby forming R18, wherein R18 is a linear or branched alkyl, alkenyl or alkoxy group, and wherein A is absent.

2. The compound according to claim 1, of a structure according to formula (II):

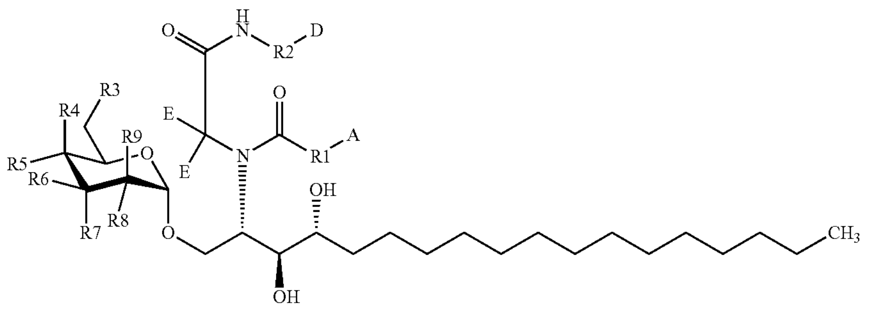

wherein

A, D, R1, R2 and E are as defined above for formula (I), and

R3 is —OH, $OC_1$-$C_{12}$ alkyl, —$CO_2H$, or R19, wherein R19 is —NHCONH—R20, —OCONH—R20, —$OCOC_1$-$C_{12}$ alkyl— or —$NHCOC_1$-$C_{12}$ alkyl—, optionally bound to R20, wherein R20 is an aromatic group, wherein the aromatic group comprises or consists of 1-2 aromatic or heteroaromatic 5- or 6- membered ring structures;

R4 and R5 are either:

R4 is —H and R5 is —H, —OH, —$OC_1$-$C_{12}$ alkyl, —$NH_2$, or R19, or

R5 is —H and R4 is —H, —OH, —$OC_1$-$C_{12}$ alkyl, —$NH_2$, or R19;

R6 and R7 are either:

R6 is —H and R7 is —H, —OH, —$OC_1$-$C_{12}$ alkyl, —$NH_2$, or R19, or

R7 is —H and R6 is —H, —OH, —$OC_1$-$C_{12}$ alkyl, —$NH_2$, or R19;

R8 and R9 are either:

R8 is —H and R9 is —H, —OH, —$OC_1$-$C_{12}$ alkyl, —$NH_2$, or R19, or

R9 is —H and R8 is —H, —OH, —$OC_1$-$C_{12}$ alkyl, —$NH_2$, or R19.

3. The compound according to claim 2, wherein R3 to R9 are selected to form galactosyl or glucosyl, GalNAc, or a deoxy sugar group.

4. The compound according to claim 1, wherein at least one of R1 and/or R2 is a $C_6$-$C_{30}$ linear or branched alkyl or alkenyl group, or an oligomeric-or polymeric-ethylene glycol chain, optionally substituted with —OH, —$NH_2$, —NHR10, —$N_3$, —C═O; acetal, —$CO_2H$, —$CO_2R11$, —$SO_3H$, —$SO_3R11$, —SH; —SR12, maleimide, —$OPO_3R13$.

5. The compound according claim 1, comprising at least 3, $C_6$-$C_{30}$ linear or branched alkyl, alkenyl, or alkoxy groups, optionally substituted as for R1 or R2 according to claim 1.

6. The compound according to claim 1, of a structure according to formula (III):

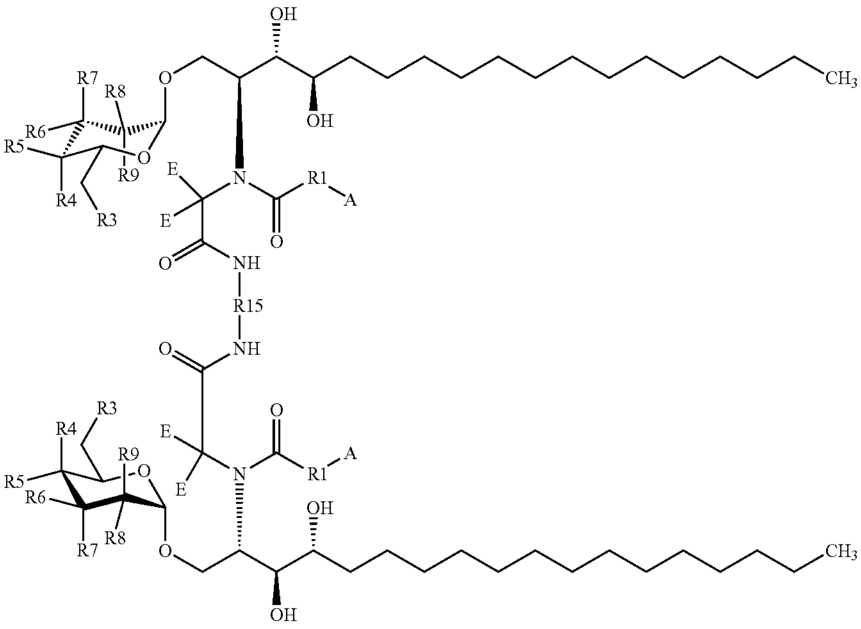

wherein

A, E and R1 are as defined in claim 1, R3 is —OH, $OC_1$-$C_{12}$ alkyl, —$CO_2H$, or R19, wherein R19 is —NHCONH-R20, —OCONH-R20, —$OCOC_1$-C12 alkyl—or —$NHCOC_1$-$C_{12}$ alkyl—, optionally bound to R20, wherein R20 is an aromatic group, wherein the aromatic group comprises or consists of 1-2 aromatic or heteroaromatic 5- or 6-membered ring structures;

R4 and R5 are either:

R4 is —H and R5 is —H, —OH, —$OC_1$-$C_{12}$ alkyl, —$NH_2$, or R19, or

R5 is —H and R4 is —H, —OH, —$OC_1$-$C_{12}$ alkyl, —$NH_2$, or R19;

R6 and R7 are either:

R6 is —H and R7 is —H, —OH, —$OC_1$-$C_{12}$ alkyl, —$NH_2$, or R19, or

R7 is —H and R6 is —H, —OH, —$OC_1$-$C_{12}$ alkyl, —$NH_2$, or R19;

R8 and R9 are either:

R8 is —H and R9 is —H, —OH, —$OC_1$-$C_{12}$ alkyl, —$NH_2$, or R19, or

R9 is —H and R8 is —H, —OH, —$OC_1$-$C_{12}$ alkyl, —$NH_2$, or R19, and

R15 is a linear or branched alkyl, alkenyl or alkoxy group, optionally substituted with —OH, —$NH_2$, —NHR10, —$N_3$, —C═O; acetal, —$CO_2H$, —$CO_2R11$, —$SO_3H$, —$SO_3R11$, —SH; —SR12, maleimide, —$OPO_3R13$, or R15 is —R16PhR17—, wherein Ph is phenyl, or a para/meta di-substituted phenyl ring and R16 and R17 are, independently, a linear or branched alkyl or alkenyl group.

7. A compound according to claim 1, of a structure according to formula (IV):

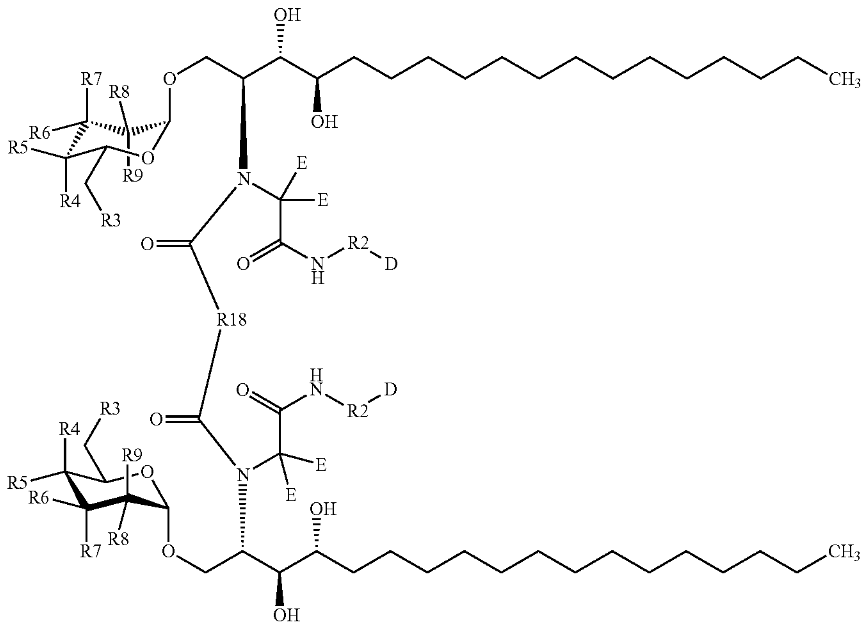

wherein

D, E and R2 are as defined in claims 1,

R3 is —OH, $OC_1$-$C_{12}$ alkyl, —$CO_2H$, or R19, wherein R19 is —NHCONH—R20, —OCONH—R20, —$OCOC_1$-$C_{12}$ alkyl- or —$NHCOC_1$-$C_{12}$ alkyl-, optionally bound to R20, wherein R20 is an aromatic group, wherein the aromatic group comprises or consists of 1-2 aromatic or heteroaromatic 5- or 6-membered ring structures;

R4 and R5 are either:

R4 is —H and R5 is —H, —OH, —$OC_1$-$C_{12}$ alkyl, —$NH_2$, or R19, or

R5 is —H and R4 is —H, —OH, —$OC_1$-$C_{12}$ alkyl, —$NH_2$, or R19;

R6 and R7 are either:

R6 is —H and R7 is —H, —OH, —$OC_1$-$C_{12}$ alkyl, —$NH_2$, or R19, or

R7 is —H and R6 is —H, —OH, —$OC_1$-$C_{12}$ alkyl, —$NH_2$, or R19;

R8 and R9 are either:

R8 is —H and R9 is —H, —OH, —$OC_1$-$C_{12}$ alkyl, —$NH_2$, or R19, or

R9 is —H and R8 is —H, —OH, —$OC_1$-$C_{12}$ alkyl, —$NH_2$, or R19, and

R18 is a linear or branched alkyl, alkenyl or alkoxy group, optionally substituted with —OH, —$NH_2$, —NHR10, —$N_3$, —C═O; acetal, —$CO_2H$, —$CO_2R11$, —$SO_3H$, —$SO_3R11$, —SH; —SR12, maleimide, —$OPO_3R13$, or R18 is —R16PhR17-, wherein Ph is phenyl, or a para/meta di-substituted phenyl ring and R16 and R17 are, independently, a linear or branched alkyl or alkenyl group.

8. The compound according to claim 1, wherein at least at least two lipophilic groups are present at R1 and/or R2, wherein said lipophilic groups are $C_6$-$C_{30}$ linear or branched alkyl or alkenyl groups, optionally substituted with —OH, —$NH_2$, —NHR10, —$N_3$, —C═O; acetal, —$CO_2H$, —$CO_2R11$, —$SO_3H$, —$SO_3R11$, —SH; —SR12, maleimide, —OPO3R13.

9. The compound according to claim 1, wherein at least at least two hydrophilic groups are present at R1 and/or R2, wherein said hydrophilic groups are an oligomeric-or polymeric-ethylene glycol chain, optionally substituted with —OH, —$NH_2$, —NHR10, —$N_3$, —C═O; acetal, —$CO_2H$, —$CO_2R11$, —$SO_3H$, —$SO_3R11$, —SH; —SR12, maleimide, —$OPO_3R13$.

10. A compound according to claim 1, selected from the group consisting of:

IPB002044

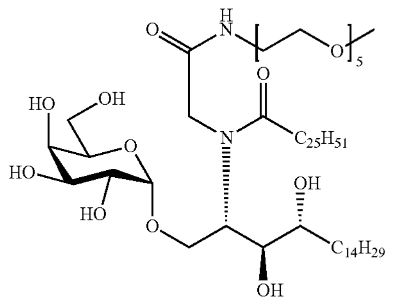

IPB002040

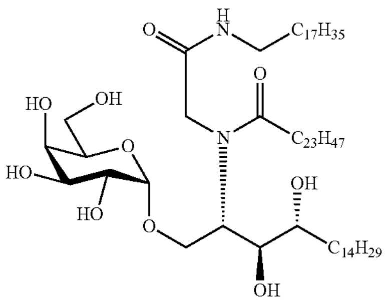

IPB002043

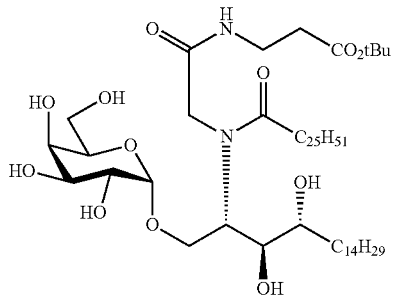

IPB002039

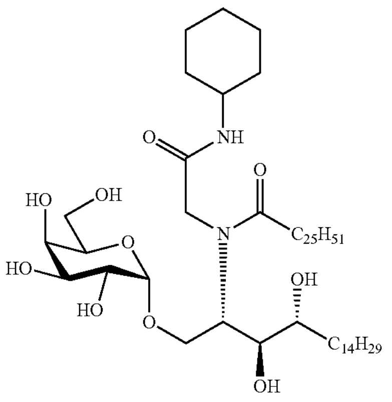

-continued
IPB002042
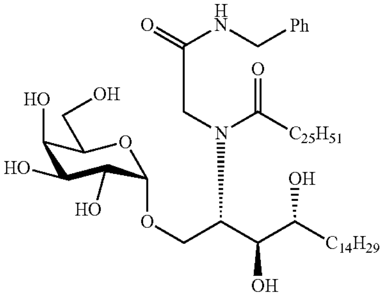
IPB002038
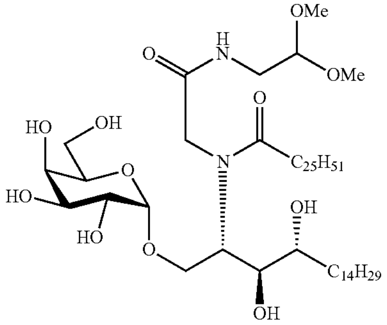
IPB002041
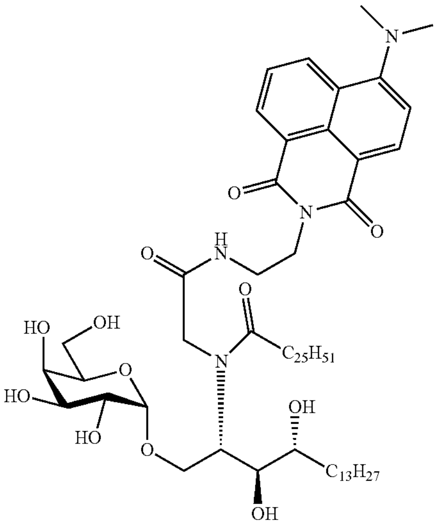
IPB002037
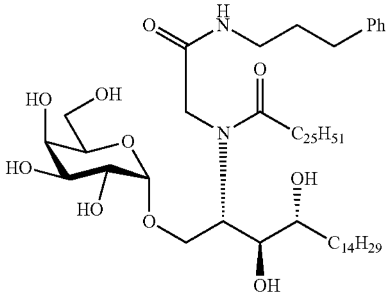
IPB002036
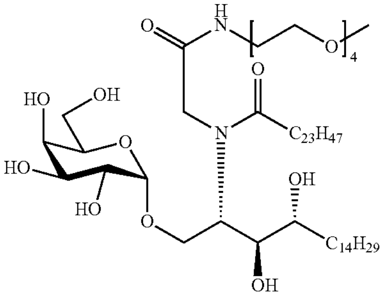
IPB001917
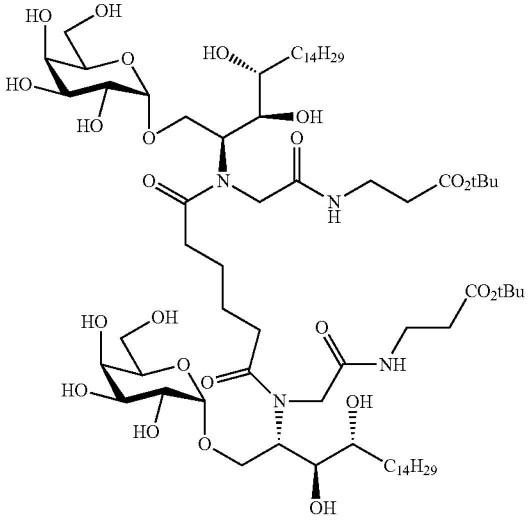

-continued
IPB002035
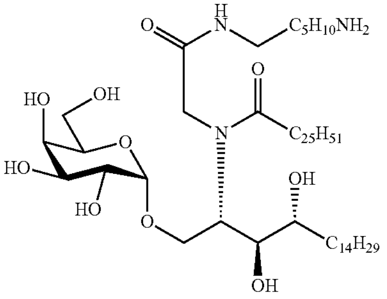
IPB002034
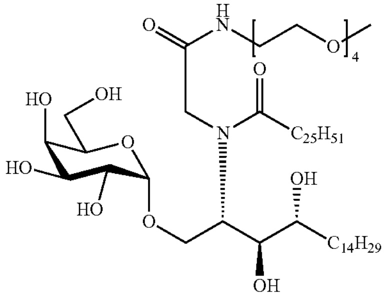
IPB001915
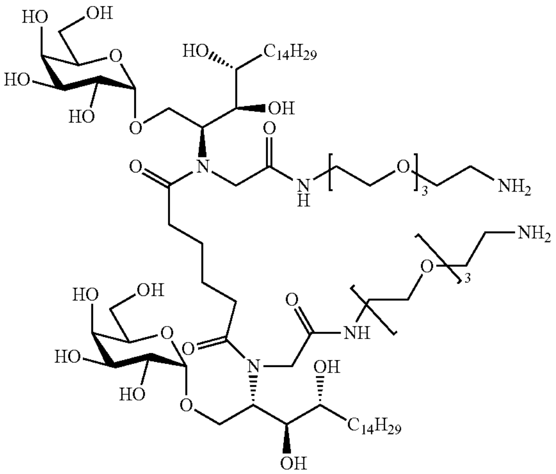
IPB002033
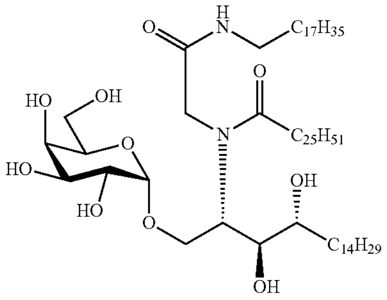
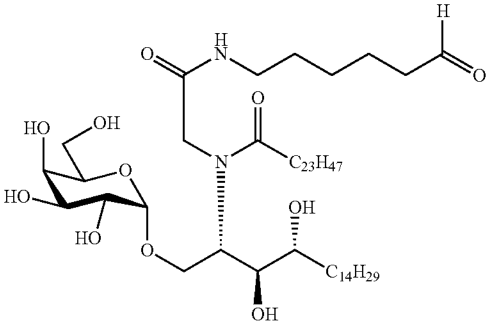
IPB000970
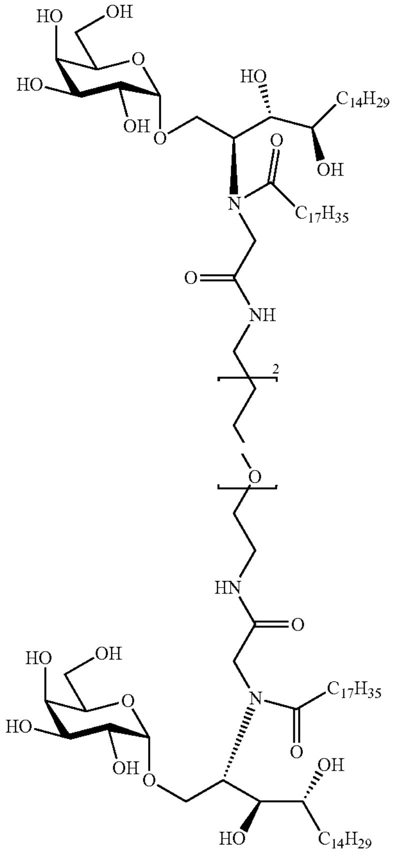

-continued
IPB001910
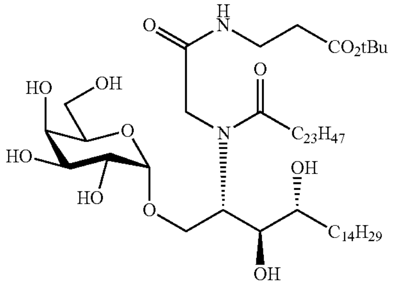
IPB000964
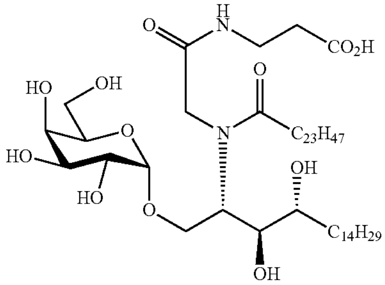
IPB001911
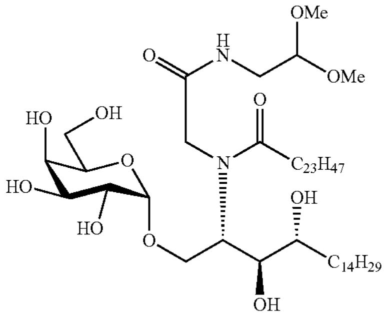
IPB001904
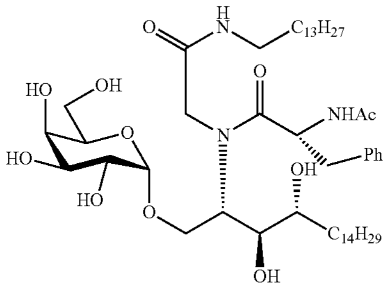
IPB001902
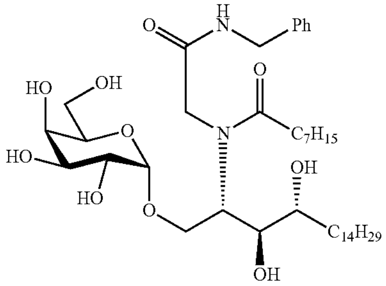
IPB001909
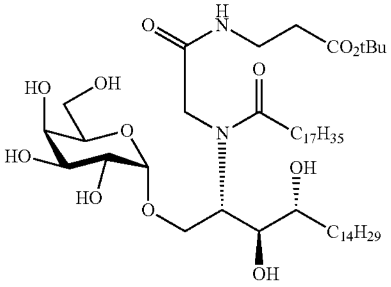
IPB001906
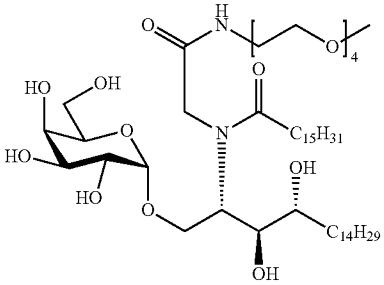
IPB001905
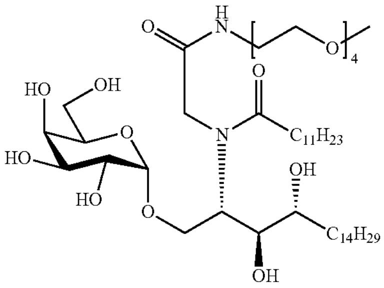
IPB001903
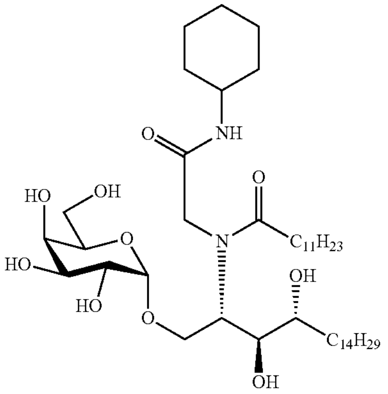
IPB001901
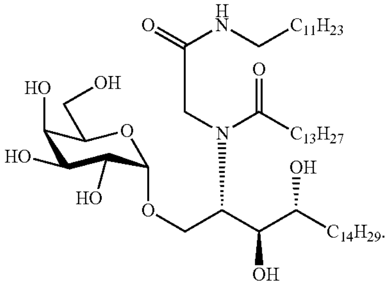

11. The compound according to claim 1, wherein A is an amino acid or a polypeptide, wherein A is a residue with the following formula:

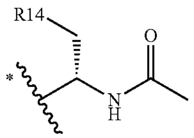

wherein R14 is a side chain of a naturally occurring amino acid.

12. The compound according to claim 1, wherein R2 is absent when D is a cycloalkyl group.

13. The compound according to claim 1, wherein D is an amino acid or a polypeptide, wherein D is a residue with the following formula:

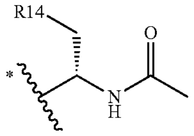

wherein R14 is a side chain of a naturally occurring amino acid.

14. The compound according to claim 1, wherein E is H.

15. A pharmaceutical composition comprising a compound according to claim 1 and a pharmaceutically acceptable carrier.

16. A method for immune stimulation in a subject that produces a therapeutic benefit, comprising administering an effective amount of a compound according to claim 1 to a subject in need thereof.

17. The method according to claim 16, wherein the compound is administered as an adjuvant in a method of vaccinating a subject.

18. The method according to claim 16, for stimulating dendritic cell (DC), natural killer (NK) cell, B cell, T cell or macrophage activity, stimulating antibody production, stimulating an immune response against infection, treating septic shock.

19. The method according to claim 18, wherein the method stimulates an immune response against a cancer.

20. A method for the manufacture of a compound according to claim 1, comprising an Ugi-4-component reaction (Ugi-4CR) followed by deprotection, said reaction comprising:

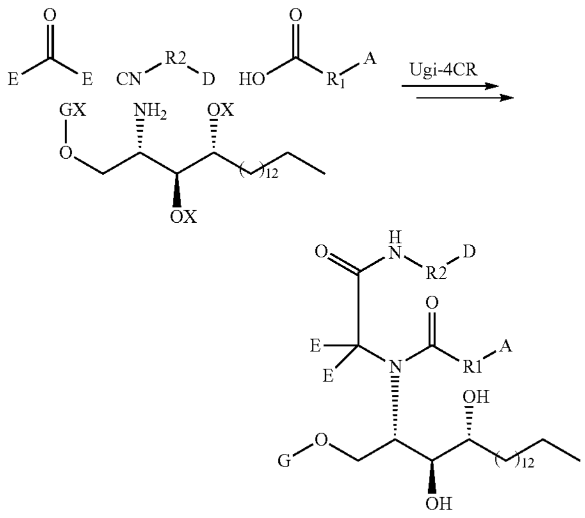

wherein A, D, G, R1, R2, E are as defined in claim 1 for formula (I), and reactive groups of A, D, G, R1, R2 are protected prior to and during the Ugi-4CR, and X is a protecting group.

* * * * *